United States Patent
Kluge et al.

(10) Patent No.: US 12,076,384 B2
(45) Date of Patent: *Sep. 3, 2024

(54) BISPECIFIC EGFR/CD16 ANTIGEN-BINDING PROTEIN

(71) Applicant: Affimed GmbH, Heidelberg (DE)

(72) Inventors: Michael Kluge, Heidelberg (DE); Michael Tesar, Heidelberg (DE); Ivica Fucek, Heidelberg (DE); Kristina Ellwanger, Heidelberg (DE); Uwe Reusch, Heidelberg (DE); Michael Damrat, Heidelberg (DE); Erich Rajkovic, Heidelberg (DE); Martin Treder, Heidelberg (DE)

(73) Assignee: AFFIMED GMBH, Heidelberg (DE)

( * ) Notice: Subject to any disclaimer, the term of this patent is extended or adjusted under 35 U.S.C. 154(b) by 24 days.

This patent is subject to a terminal disclaimer.

(21) Appl. No.: 18/047,917

(22) Filed: Oct. 19, 2022

(65) Prior Publication Data

US 2023/0190900 A1 Jun. 22, 2023

Related U.S. Application Data

(63) Continuation of application No. 17/010,622, filed on Sep. 2, 2020, now Pat. No. 11,510,972, which is a continuation of application No. PCT/EP2019/056516, filed on Mar. 14, 2019.

(30) Foreign Application Priority Data

Mar. 14, 2018 (EP) ..................... 18161871

(51) Int. Cl.
- *A61K 39/00* (2006.01)
- *A61K 47/65* (2017.01)
- *A61P 35/00* (2006.01)

(52) U.S. Cl.
CPC .............. *A61K 39/001104* (2018.08); *A61K 39/001129* (2018.08); *A61K 47/65* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 8,289,183 B1 | 10/2012 | Foss | |
| 11,510,972 B2* | 11/2022 | Kluge | ............ A61K 47/65 |
| 2013/0039913 A1 | 2/2013 | Labrijn et al. | |
| 2015/0119555 A1 | 4/2015 | Jung et al. | |
| 2015/0175707 A1 | 6/2015 | De Jong et al. | |
| 2016/0009824 A1 | 1/2016 | Lo et al. | |

FOREIGN PATENT DOCUMENTS

| | | |
|---|---|---|
| WO | 2011140254 A1 | 11/2011 |
| WO | 2014144357 A1 | 9/2014 |
| WO | 2016177846 A1 | 11/2016 |

OTHER PUBLICATIONS

European Patent Office (Epo), International Search Report and Written Opinion, PCT/EP2019/056516, Jul. 15, 2019.

Ryutaro Asano et al., Construction and humanization of a functional bispecific EGFR X CD16 diabody using a refolding system, FEBS Journal, vol. 279, No. 2, Jan. 1, 2012, pp. 223-233.

Anne Kerber, et al., EGFR/CD16A tetravalent bispecific antibody AFM24 to engage NK-cells to kill EGFR expressing tumor cells and safety results in cynomolgus monkey studies, Journal of Clinical Oncology: vol. 35, No. 15, May 17, 2017.

Michael Kluge et al., High affinity bispecific EGFR/CD16A antibodies specifically recruit NK-cells to target EGFR- expressing tumors, Jun. 6, 2016.

Tomohiro Osaki et al., Development of a bispecific antibody tetramerized through hetero-associating peptides, FEBS Journal, vo. 282, No. 22, Nov. 1, 2015, pp. 4389-4401.

Ryutaro Asano et al., Functionalization of Bispecific Therapeutic Antibodies Based on Protein Engineering, Yakugaku Zasshi, vol. 135, No. 7, The Pharmaceutical Society of Japane, Jan. 18, 2015, pp. 851-856.

* cited by examiner

*Primary Examiner* — Laura B Goddard
*Assistant Examiner* — Sarah A Alsomairy
(74) *Attorney, Agent, or Firm* — Perkins Coie LLP; Viola Kung

(57) ABSTRACT

Described are tetravalent, bispecific EGFR/CD16A antigen-binding proteins for engaging NK-cells towards EGFR-positive cells. EGFR/CD16A antigen-binding proteins with different pharmacokinetic (PK) properties are described. Further described is the use of bispecific EGFR/CD16A antigen-binding proteins for the treatment of an EGFR-positive malignancy, such as EGFR-positive tumors.

17 Claims, 26 Drawing Sheets

Specification includes a Sequence Listing.

A

B

A

B

A

B

A

B

SEQUENCE LISTING

```
Sequence total quantity: 45
SEQ ID NO: 1              moltype = AA   length = 120
FEATURE                   Location/Qualifiers
REGION                    1..120
                          note = vh domain
source                    1..120
                          mol_type = protein
                          organism = synthetic construct
SEQUENCE: 1
QVQLQESGPG LVKPSETLSL TCTVSGGSVS SGSYYWSWIR QPPGKGLEWI GYIYYSGSTN    60
YNPSLKSRVT ISVDTSKNQF SLKLSSVTAA DTAVYYCARN PISIPAFDIW GQGTMVTVSS   120

SEQ ID NO: 2              moltype = AA   length = 108
FEATURE                   Location/Qualifiers
REGION                    1..108
                          note = vl domain
source                    1..108
                          mol_type = protein
                          organism = synthetic construct
SEQUENCE: 2
QPVLTQPPSV SVAPGKTARI TCGGNNIGSK SVHWYQQKPG QAPVLVIYYD SDRPSGIPER    60
FSGSNSGNTA TLTISRVEAG DEADYYCQVW DTSSDHVLFG GGTKLTVL               108

SEQ ID NO: 3              moltype = AA   length = 8
FEATURE                   Location/Qualifiers
source                    1..8
                          mol_type = protein
                          organism = Homo sapiens
SEQUENCE: 3
SFFPPGYQ                                                              8

SEQ ID NO: 4              moltype = AA   length = 192
FEATURE                   Location/Qualifiers
source                    1..192
                          mol_type = protein
                          organism = Homo sapiens
SEQUENCE: 4
GMRTEDLPKA VVFLEPQWYR VLEKDSVTLK CQGAYSPEDN STQWFHNESL ISSQASSYFI    60
DAATVDDSGE YRCQTNLSTL SDPVQLEVHI GWLLLQAPRW VFKEEDPIHL RCHSWKNTAL   120
HKVTYLQNGK GRKYFHHNSD FYIPKATLKD SGSYFCRGLF GSKNVSSETV NITITQGLAV   180
STISSFFPPG YQ                                                       192

SEQ ID NO: 5              moltype = AA   length = 8
FEATURE                   Location/Qualifiers
REGION                    1..8
                          note = cdr
source                    1..8
                          mol_type = protein
                          organism = synthetic construct
SEQUENCE: 5
GYTFTSYY                                                              8

SEQ ID NO: 6              moltype = AA   length = 8
FEATURE                   Location/Qualifiers
REGION                    1..8
                          note = cdr
source                    1..8
                          mol_type = protein
                          organism = synthetic construct
SEQUENCE: 6
```

```
INPSGGST                                                                        8

SEQ ID NO: 7            moltype = AA  length = 13
FEATURE                 Location/Qualifiers
REGION                  1..13
                        note = cdr
source                  1..13
                        mol_type = protein
                        organism = synthetic construct
SEQUENCE: 7
ARGSAYYYDF ADY                                                                 13

SEQ ID NO: 8            moltype = AA  length = 6
FEATURE                 Location/Qualifiers
REGION                  1..6
                        note = cdr
source                  1..6
                        mol_type = protein
                        organism = synthetic construct
SEQUENCE: 8
NIGSKN                                                                          6

SEQ ID NO: 9            moltype = AA  length = 5
FEATURE                 Location/Qualifiers
REGION                  1..5
                        note = cdr
source                  1..5
                        mol_type = protein
                        organism = synthetic construct
SEQUENCE: 9
QDNKR                                                                           5

SEQ ID NO: 10           moltype = AA  length = 9
FEATURE                 Location/Qualifiers
REGION                  1..9
                        note = cdr
source                  1..9
                        mol_type = protein
                        organism = synthetic construct
SEQUENCE: 10
QVWDNYSVL                                                                       9

SEQ ID NO: 11           moltype = AA  length = 8
FEATURE                 Location/Qualifiers
REGION                  1..8
                        note = cdr
source                  1..8
                        mol_type = protein
                        organism = synthetic construct
SEQUENCE: 11
IEPMYGST                                                                        8

SEQ ID NO: 12           moltype = AA  length = 120
FEATURE                 Location/Qualifiers
REGION                  1..120
                        note = vh
source                  1..120
                        mol_type = protein
                        organism = synthetic construct
SEQUENCE: 12
QVQLVQSGAE VKKPGESLKV SCKASGYTFT SYYMHWVRQA PGQGLEWMGI INPSGGSTSY              60
AQKFQGRVTM TRDTSTSTVY MELSSLRSED TAVYYCARGS AYYYDFADYW GQGTLVTVSS             120

SEQ ID NO: 13           moltype = AA  length = 106
FEATURE                 Location/Qualifiers
REGION                  1..106
                        note = vl
source                  1..106
                        mol_type = protein
                        organism = synthetic construct
SEQUENCE: 13
SYVLTQPSSV SVAPGQTATI SCGGHNIGSK NVHWYQQRPG QSPVLVIYQD NKRPSGIPER              60
FSGSNSGNTA TLTISGTQAM DEADYYCQVW DNYSVLFGGG TKLTVL                            106

SEQ ID NO: 14           moltype = AA  length = 120
FEATURE                 Location/Qualifiers
REGION                  1..120
                        note = vh
source                  1..120
```

```
                            mol_type = protein
                            organism = synthetic construct
SEQUENCE: 14
QVQLVQSGAE VKKPGESLKV SCKASGYTFT SYYMHWVRQA PGQGLEWMGA IEPMYGSTSY    60
AQKFQGRVTM TRDTSTSTVY MELSSLRSED TAVYYCARGS AYYYDFADYW GQGTLVTVSS   120

SEQ ID NO: 15               moltype = AA   length = 328
FEATURE                     Location/Qualifiers
REGION                      1..328
                            note = silenced Fc
source                      1..328
                            mol_type = protein
                            organism = synthetic construct
SEQUENCE: 15
ASTKGPSVFP LAPSSKSTSG GTAALGCLVK DYFPEPVTVS WNSGALTSGV HTFPAVLQSS    60
GLYSLSSVVV PSSSLGTQTY ICNVNHKPSN TKVDKKVEPK SCDKTHTCPP CPAPEFEGGP   120
SVFLFPPKPK DTLMISRTPE VTCVVVAVSH EDPEVKFNWY VDGVEVHNAK TKPREEQYNS   180
TYRVVSVLTV LHQDWLNGKE YKCKVSNKAL PAPIEKTISK AKGQPREPQV YTLPPSREEM   240
TKNQVSLTCL VKGFYPSDIA VEWESNGQPE NNYKTTPPVL DSDGSFFLYS KLTVDKSRWQ   300
QGNVFSCSVM HEALHNHYTQ KSLSLSPG                                     328

SEQ ID NO: 16               moltype = AA   length = 106
FEATURE                     Location/Qualifiers
source                      1..106
                            mol_type = protein
                            organism = Homo sapiens
SEQUENCE: 16
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 17               moltype = AA   length = 10
FEATURE                     Location/Qualifiers
REGION                      1..10
                            note = linker
source                      1..10
                            mol_type = protein
                            organism = synthetic construct
SEQUENCE: 17
GGGGSGGGGS                                                           10

SEQ ID NO: 18               moltype = AA   length = 18
FEATURE                     Location/Qualifiers
REGION                      1..18
                            note = linker
source                      1..18
                            mol_type = protein
                            organism = synthetic construct
SEQUENCE: 18
GGSGGSGGSG GSGGSGGS                                                  18

SEQ ID NO: 19               moltype = AA   length = 15
FEATURE                     Location/Qualifiers
source                      1..15
                            mol_type = protein
                            organism = Homo sapiens
SEQUENCE: 19
EPKSCDKTHT CPPCP                                                     15

SEQ ID NO: 20               moltype = AA   length = 216
FEATURE                     Location/Qualifiers
REGION                      1..216
                            note = silenced Fc
source                      1..216
                            mol_type = protein
                            organism = synthetic construct
SEQUENCE: 20
APEFEGGPSV FLFPPKPKDT LMISRTPEVT CVVVAVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNHYTQKS LSLSPG                             216

SEQ ID NO: 21               moltype = AA   length = 10
FEATURE                     Location/Qualifiers
REGION                      1..10
                            note = cdr
source                      1..10
                            mol_type = protein
                            organism = synthetic construct
SEQUENCE: 21
```

-continued

```
GGSVSSGSYY                                                              10

SEQ ID NO: 22           moltype = AA  length = 7
FEATURE                 Location/Qualifiers
REGION                  1..7
                        note = cdr
source                  1..7
                        mol_type = protein
                        organism = synthetic construct
SEQUENCE: 22
IYYSGST                                                                 7

SEQ ID NO: 23           moltype = AA  length = 12
FEATURE                 Location/Qualifiers
REGION                  1..12
                        note = cdr
source                  1..12
                        mol_type = protein
                        organism = synthetic construct
SEQUENCE: 23
ARNPISIPAF DI                                                           12

SEQ ID NO: 24           moltype = AA  length = 6
FEATURE                 Location/Qualifiers
REGION                  1..6
                        note = cdr
source                  1..6
                        mol_type = protein
                        organism = synthetic construct
SEQUENCE: 24
NIGSKS                                                                  6

SEQ ID NO: 25           moltype = AA  length = 4
FEATURE                 Location/Qualifiers
REGION                  1..4
                        note = cdr
source                  1..4
                        mol_type = protein
                        organism = synthetic construct
SEQUENCE: 25
YDSD                                                                    4

SEQ ID NO: 26           moltype = AA  length = 11
FEATURE                 Location/Qualifiers
REGION                  1..11
                        note = cdr
source                  1..11
                        mol_type = protein
                        organism = synthetic construct
SEQUENCE: 26
QVWDTSSDHV L                                                            11

SEQ ID NO: 27           moltype = AA  length = 489
FEATURE                 Location/Qualifiers
REGION                  1..489
                        note = tandem diabody
source                  1..489
                        mol_type = protein
                        organism = synthetic construct
SEQUENCE: 27
QVQLQESGPG LVKPSETLSL TCTVSGGSVS SGSYYWSWIR QPPGKGLEWI GYIYYSGSTN        60
YNPSLKSRVT ISVDTSKNQF SLKLSSVTAA DTAVYYCARN PISIPAFDIW GQGTMVTVSS        120
GGSGGSGGSS YVLTQPSSVS VAPGQTATIS CGGHNIGSKN VHWYQQRPGQ SPVLVIYQDN        180
KRPSGIPERF SGSNSGNTAT LTISGTQAMD EADYYCQVWD NYSVLFGGGT KLTVLGGSGG        240
SQVQLVQSGA EVKKPGESLK VSCKASGYTF TSYYMHWVRQ APGQGLEWMG IINPSGGSTS        300
YAQKFQGRVT MTRDTSTSTV YMELSSLRSE DTAVYYCARG SAYYYDFADY WGQGTLVTVS        360
SGGSGGSGGS QPVLTQPPSV SVAPGKTARI TCGGNNIGSK SVHWYQQKPG QAPVLVIYYD        420
SDRPSGIPER FSGSNSGNTA TLTISRVEAG DEADYYCQVW DTSSDHVLFG GGTKLTVLAA        480
AGSHHHHHH                                                               489

SEQ ID NO: 28           moltype = AA  length = 705
FEATURE                 Location/Qualifiers
REGION                  1..705
                        note = heavy chain
source                  1..705
                        mol_type = protein
                        organism = synthetic construct
SEQUENCE: 28
QVQLVQSGAE VKKPGESLKV SCKASGYTFT SYYMHWVRQA PGQGLEWMGI INPSGGSTSY        60
```

```
AQKFQGRVTM TRDTSTSTVY MELSSLRSED TAVYYCARGS AYYYDFADYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEFEGG    240
PSVFLFPPKP KDTLMISRTP EVTCVVVAVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGG GGGSGGGGSQ VQLQESGPGL VKPSETLSLT    480
CTVSGGSVSS GSYYWSWIRQ PPGKGLEWIG YIYYSGSTNY NPSLKSRVTI SVDTSKNQFS    540
LKLSSVTAAD TAVYYCARNP ISIPAFDIWG QGTMVTVSSG GSGGSGGSGG SGGSGGSQPV    600
LTQPPSVSVA PGKTARITCG GNNIGSKSVH WYQQKPGQAP VLVIYYDSDR PSGIPERFSG    660
SNSGNTATLT ISRVEAGDEA DYYCQVWDTS SDHVLFGGGT KLTVL                   705

SEQ ID NO: 29           moltype = AA   length = 212
FEATURE                 Location/Qualifiers
REGION                  1..212
                        note = light chain
source                  1..212
                        mol_type = protein
                        organism = synthetic construct SEQUENCE: 29
SYVLTQPSSV SVAPGQTATI SCGGHNIGSK NVHWYQQRPG QSPVLVIYQD NKRPSGIPER     60
FSGSNSGNTA TLTISGTQAM DEADYYCQVW DNYSVLFGGG TKLTVLGQPK AAPSVTLFPP    120
SSEELQANKA TLVCLISDFY PGAVTVAWKA DSSPVKAGVE TTTPSKQSNN KYAASSYLSL    180
TPEQWKSHRS YSCQVTHEGS TVEKTVAPTE CS                                  212

SEQ ID NO: 30           moltype = AA   length = 734
FEATURE                 Location/Qualifiers
REGION                  1..734
                        note = Bi-scFv-Fc
source                  1..734
                        mol_type = protein
                        organism = synthetic construct SEQUENCE: 30
SYVLTQPSSV SVAPGQTATI SCGGHNIGSK NVHWYQQRPG QSPVLVIYQD NKRPSGIPER     60
FSGSNSGNTA TLTISGTQAM DEADYYCQVW DNYSVLFGGG TKLTVLGGSG GSGGSGGSGG    120
SGGSGGSQVQ LVQSGAEVKK PGESLKVSCK ASGYTFTSYY MHWVRQAPGQ GLEWMGIINP    180
SGGSTSYAQK FQGRVTMTRD TSTSTVYMEL SSLRSEDTAV YYCARGSAYY YDFADYWGQG    240
TLVTVSSEPK SCDKTHTCPP CPAPEFEGGP SVFLFPPKPK DTLMISRTPE VTCVVVAVSH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREEM TKNQVSLTCL VKGFYPSDIA VEWESNGQPE    420
NNYKTTPPVL DSDGSFFLYS KLTVDKSRWQ QGNVFSCSVM HEALHNHYTQ KSLSLSPGGG    480
GGSGGGGSQV QLQESGPGLV KPSETLSLTC TVSGGSVSSG SYYWSWIRQP PGKGLEWIGY    540
IYYSGSTNYN PSLKSRVTIS VDTSKNQFSL KLSSVTAADT AVYYCARNPI SIPAFDIWGQ    600
GTMVTVSSGG SGGSGGSGGS GGSGGSQPVL TQPPSVSVAP GKTARITCGG NNIGSKSVHW    660
YQQKPGQAPV LVIYYDSDRP SGIPERFSGS NSGNTATLTI SRVEAGDEAD YYCQVWDTSS    720
DHVLFGGGTK LTVL                                                     734

SEQ ID NO: 31           moltype = AA   length = 121
FEATURE                 Location/Qualifiers
REGION                  1..121
                        note = vh
source                  1..121
                        mol_type = protein
                        organism = synthetic construct
SEQUENCE: 31
EVQLLESGGG LVQPGGSLRL SCAVSGIDLS NYAINWVRQA PGKGLEWIGI IWASGTTFYA     60
TWAKGRFTIS RDNSKNTVYL QMNSLRAEDT AVYYCARTVP GYSTAPYFDL WGQGTLVTVS    120
S                                                                   121

SEQ ID NO: 32           moltype = AA   length = 110
FEATURE                 Location/Qualifiers
REGION                  1..110
                        note = vl
source                  1..110
                        mol_type = protein
                        organism = synthetic construct
SEQUENCE: 32
DIQMTQSPSS VSASVGDRVT ITCQSSPSVW SNFLSWYQQK PGKAPKLLIY EASKLTSGVP     60
SRFSGSGSGT DFTLTISSLQ PEDFATYYCG GGYSSISDTT FGGGTKVEIK               110

SEQ ID NO: 33           moltype = DNA  length = 20
FEATURE                 Location/Qualifiers
misc_feature            1..20
                        note = primer
source                  1..20
                        mol_type = other DNA
                        organism = synthetic construct
SEQUENCE: 33
taatacgact cactataggg                                                 20
```

```
SEQ ID NO: 34          moltype = DNA  length = 18
FEATURE                Location/Qualifiers
misc_feature           1..18
                       note = primer
source                 1..18
                       mol_type = other DNA
                       organism = synthetic construct
SEQUENCE: 34
tagaaggcac agtcgagg                                                     18

SEQ ID NO: 35          moltype = AA  length = 6
FEATURE                Location/Qualifiers
REGION                 1..6
                       note = linker
source                 1..6
                       mol_type = protein
                       organism = synthetic construct
SEQUENCE: 35
GGSGGS                                                                   6

SEQ ID NO: 36          moltype = AA  length = 9
FEATURE                Location/Qualifiers
REGION                 1..9
                       note = linker
source                 1..9
                       mol_type = protein
                       organism = synthetic construct
SEQUENCE: 36
GGSGGSGGS                                                                9

SEQ ID NO: 37          moltype = AA  length = 21
FEATURE                Location/Qualifiers
REGION                 1..21
                       note = linker
source                 1..21
                       mol_type = protein
                       organism = synthetic construct
SEQUENCE: 37
GGSGGSGGSG GSGGSGGSGG S                                                 21

SEQ ID NO: 38          moltype = AA  length = 8
FEATURE                Location/Qualifiers
REGION                 1..8
                       note = HCDR1
source                 1..8
                       mol_type = protein
                       organism = synthetic construct
SEQUENCE: 38
GYTFTSYY                                                                 8

SEQ ID NO: 39          moltype = AA  length = 13
FEATURE                Location/Qualifiers
REGION                 1..13
                       note = HCDR3
source                 1..13
                       mol_type = protein
                       organism = synthetic construct
SEQUENCE: 39
ARGSAYYYDF ADY                                                          13

SEQ ID NO: 40          moltype = AA  length = 6
FEATURE                Location/Qualifiers
REGION                 1..6
                       note = LCDR1
source                 1..6
                       mol_type = protein
                       organism = synthetic construct
SEQUENCE: 40
NIGSKN                                                                   6

SEQ ID NO: 41          moltype =     length =
SEQUENCE: 41
000

SEQ ID NO: 42          moltype = AA  length = 9
FEATURE                Location/Qualifiers
REGION                 1..9
                       note = LCDR3
```

```
source                  1..9
                        mol_type = protein
                        organism = synthetic construct
SEQUENCE: 42
QVWDNYSVL                                                               9

SEQ ID NO: 43           moltype = AA  length = 705
FEATURE                 Location/Qualifiers
REGION                  1..705
                        note = heavy chain
source                  1..705
                        mol_type = protein
                        organism = synthetic construct
SEQUENCE: 43
QVQLVQSGAE VKKPGESLKV SCKASGYTFT SYYMHWVRQA PGQGLEWMGA IEPMYGSTSY      60
AQKFQGRVTM TRDTSTSTVY MELSSLRSED TAVYYCARGS AYYYDFADYW GQGTLVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSCDKTHTCP PCPAPEFEGG     240
PSVFLFPPKP KDTLMISRTP EVTCVVVAVS HEDPEVKFNW YVDGVEVHNA KTKPREEQYN     300
STYRVVSVLT VLHQDWLNGK EYKCKVSNKA LPAPIEKTIS KAKGQPREPQ VYTLPPSREE     360
MTKNQVSLTC LVKGFYPSDI AVEWESNGQP ENNYKTTPPV LDSDGSFFLY SKLTVDKSRW     420
QQGNVFSCSV MHEALHNHYT QKSLSLSPGG GGGSGGGGSQ VQLQESGPGL VKPSETLSLT     480
CTVSGGSVSS GSYYWSWIRQ PPGKGLEWIG YIYYSGSTNY NPSLKSRVTI SVDTSKNQFS     540
LKLSSVTAAD TAVYYCARNP ISIPAFDIWG QGTMVTVSSG GSGGSGGSGG SGGSGGSQPV     600
LTQPPSVSVA PGKTARITCG GNNIGSKSVH WYQQKPGQAP VLVIYYDSDR PSGIPERFSG     660
SNSGNTATLT ISRVEAGDEA DYYCQVWDTS SDHVLFGGGT KLTVL                     705

SEQ ID NO: 44           moltype = AA  length = 212
FEATURE                 Location/Qualifiers
REGION                  1..212
                        note = light chain
source                  1..212
                        mol_type = protein
                        organism = synthetic construct
SEQUENCE: 44
SYVLTQPSSV SVAPGQTATI SCGGHNIGSK NVHWYQQRPG QSPVLVIYQD NKRPSGIPER      60
FSGSNSGNTA TLTISGTQAM DEADYYCQVW DNYSVLFGGG TKLTVLGQPK AAPSVTLFPP     120
SSEELQANKA TLVCLISDFY PGAVTVAWKA DSSPVKAGVE TTTPSKQSNN KYAASSYLSL     180
TPEQWKSHRS YSCQVTHEGS TVEKTVAPTE CS                                   212

SEQ ID NO: 45           moltype = AA  length = 734
FEATURE                 Location/Qualifiers
REGION                  1..734
                        note = heavy chain
source                  1..734
                        mol_type = protein
                        organism = synthetic construct
SEQUENCE: 45
SYVLTQPSSV SVAPGQTATI SCGGHNIGSK NVHWYQQRPG QSPVLVIYQD NKRPSGIPER      60
FSGSNSGNTA TLTISGTQAM DEADYYCQVW DNYSVLFGGG TKLTVLGGSG GSGGSGGSGG     120
SGGSGGSQVQ LVQSGAEVKK PGESLKVSCK ASGYTFTSYY MHWVRQAPGQ GLEWMGAIEP     180
MYGSTSYAQK FQGRVTMTRD TSTSTVYMEL SSLRSEDTAV YYCARGSAYY YDFADYWGQG     240
TLVTVSSEPK SCDKTHTCPP CPAPEFEGGP SVFLFPPKPK DTLMISRTPE VTCVVVAVSH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREEM TKNQVSLTCL VKGFYPSDIA VEWESNGQPE     420
NNYKTTPPVL DSDGSFFLYS KLTVDKSRWQ QGNVFSCSVM HEALHNHYTQ KSLSLSPGGG     480
GGSGGGGSQV QLQESGPGLV KPSETLSLTC TVSGGSVSSG SYYWSWIRQP PGKGLEWIGY     540
IYYSGSTNYN PSLKSRVTIS VDTSKNQFSL KLSSVTAADT AVYYCARNPI SIPAFDIWGQ     600
GTMVTVSSGG SGGSGGSGGS GGSGGSQPVL TQPPSVSVAP GKTARITCGG NNIGSKSVHW     660
YQQKPGQAPV LVIYYDSDRP SGIPERFSGS NSGNTATLTI SRVEAGDEAD YYCQVWDTSS     720
DHVLFGGGTK LTVL                                                        734
```

BISPECIFIC EGFR/CD16 ANTIGEN-BINDING PROTEIN

This application is a continuation of U.S. application Ser. No. 17/010,622, filed Sep. 2, 2020, which is a continuation of PCT/EP2019/056516, filed Mar. 14, 2019; which claims priority to EP Application No. 18161871.1, filed Mar. 14, 2018. The contents of the above applications are incorporated herein by reference in their entirety.

REFERENCE TO SEQUENCE LISTING, TABLE OR COMPUTER PROGRAM

This application contains an ST.26 compliant Sequence Listing, which is submitted concurrently in xml format via Patent Center and is hereby incorporated by reference in its entirety. The .xml copy, created on Oct. 19, 2022, is named A 3317 us sequence listing.xml and is 57,700 bytes in size.

FIELD OF THE INVENTION

The invention relates to tetravalent, bispecific EGFR/CD16A antigen-binding proteins for engaging NK-cells towards EGFR-positive cells and their use for the treatment of an EGFR-positive malignancy, such as EGFR-positive tumors.

BACKGROUND OF THE INVENTION

The epidermal growth factor receptor (EGFR) is a validated target for the treatment of several solid tumors. Current EGFR-targeting monoclonal antibodies (mAbs) and tyrosine kinase inhibitors (TKI) function mainly through blocking of signal-transduction. Moreover, treatment efficacy with these agents is either dependent on the receptor's or signaling pathway's mutational status such as the T790M gatekeeper mutation in the tyrosine kinase domain or mutations downstream in the signal transduction cascade (e.g. RAS or RAF), which may cause treatment intrinsic or acquired resistance in a large number of patients. In addition, EGFR-targeting therapies have been associated with side effects considered to impact prescription rates. The epidermal growth factor receptor (EGFR) is a member of the HER family of receptor tyrosine kinases and consists of four members: EGFR (ErbB1/HER1), HER2/neu (ErbB2), HER3 (ErbB3) and HER4 (ErbB4). Stimulation of the receptor through ligand binding (e.g. EGF, TGFa, HB-EGF, neuregulins, betacellulin, amphiregulin) activates the intrinsic receptor tyrosine kinase through tyrosine phosphorylation and promotes receptor homo- or heterodimerization with HER family members. These phospho-tyrosines serve as docking sites for various adaptor proteins or enzymes including MAPK and PI(3)K/Akt, which simultaneously initiate many signaling cascades that influence cell proliferation, angiogenesis, apoptosis resistance, invasion and metastasis.

The epidermal growth factor receptor (EGFR) family of receptor tyrosine kinases has been described as a driving factor in the development and growth of a wide range of pathophysiological states such as malignant tumors and the aberrant expression or activity of EGFR is identified in many human epithelial cancers. Specifically, the EGFR gene has been described to be amplified in many cancers and a number of kinase-activating mutations in EGFR have been described and well characterized. EGFRvIII is an extracellular domain mutant of EGFR resulting from in-frame deletion of base pairs spanning exons 2-7 of the EGFR coding sequence and renders the mutant incapable of binding to a ligand. EGFR signaling in EGFRvIII mutated tumors has been reported to be constitutively active thereby driving tumor progression. Also, the ligands binding to and activating HER family members including EGFR have been documented to be overexpressed or implicated in autocrine stimulation loops. Furthermore, HER2 has been described to be gene-amplified in many cancers resulting in auto-phosphorylated HER2 receptors (homodimerization) or constitutively activated heterodimers (e.g. EGFR/HER2).

TKIs specific to EGFR have been developed and are marketed in a number of cancers but, similar to other cancer drugs, have shown severe side effects. The reason for these side effects is a coincident inhibition of EGFR activity and that of downstream molecules such as MAPK in tissues that depend on EGFR signaling for normal function. The most common tissue affected by these drugs is the skin. The side effects include an acne-like rash, dry skin, itching, nail changes and hair changes. Because of the importance of EGFR signaling in skin, dermatological toxicities have frequently been described with TKIs. The resultant significant physical and psycho-social discomfort might lead to interruption or dose modification of anticancer agents.

In more detail, inhibition of EGFR activity at these sites can result in abnormal proliferation, migration and/or differentiation of normal EGFR-positive cells such as keratinocytes, and disruption of the integrity of the skin with the recruitment of inflammatory cells. A pharmacologically- or therapeutically mediated blockade of EGFR signaling results in growth arrest and apoptosis of normal cells that are dependent on EGFR for survival. The skin is composed of three layers: the epidermis is the most superficial layer, which overlies the dermis (providing support and tensile strength) and the hypodermis (adipose tissue). The epidermis is composed primarily of keratinocytes (approximately 90% of cells), which express the highest numbers of EGFR (epidermal growth factor receptor) in the basal and suprabasal layers. The basal layer and the bulge of the hair follicle contain proliferating stem cells, which give rise to terminally differentiating keratinocytes that migrate outwards and form the stratum corneum, in which anucleate cells form a protective barrier. The outer root sheath of the hair follicle is contiguous with the basal layer, sharing biochemical properties and high EGFR expression.

It is widely accepted that TKIs affect basal keratinocytes, leading to the development of cutaneous side effects. During therapy with an EGFR-targeting inhibitor, the phosphorylation level of EGFR has been shown to be decreased or abolished in epidermal cells and the level of this dephosphorylation correlates with the degree of skin toxicity. Inhibition of EGFR in basal keratinocytes leads to growth arrest and premature differentiation. Subsequently, inhibition of the EGFR signal transduction affects EGFR-expressing cells such as keratinocytes by inducing growth arrest and apoptosis, decreasing cell migration, increasing cell attachment and differentiation, and stimulating inflammation, all of which result in distinctive cutaneous manifestations such as severe skin rash. Although inflammation is responsible for many of the signs and symptoms that are associated with the rash, the primary event seems to be drug-induced, antibody-induced or TKI-induced altered EGFR signaling.

In clinical studies, efficacy has been linked to skin toxicity, mostly in the form of rash. This applies both to EGFR-targeting mAbs, like cetuximab and panitumumab, and to TKIs. Overall, many phase II and III clinical trials using EGFR-targeting agents have shown an association between rash incidence, severity and survival.

Cetuximab was dosed weekly in a pivotal repeat dose toxicity study in monkeys at 7.5, 24 and 75 mg/kg after an initial higher loading dose. The onset of skin toxicity was observed for cetuximab after 15, 22 and 64 days in high, mid and low dose group respectively. Further, skin toxicity was observed after administration of panitumumab within 7-14 days (i.e. after two or three doses).

The clinical experience with the monoclonal antibody nimotuzumab suggests that clinical efficacy may also be accompanied by a low toxicity profile. The typical severe dermatologic toxicities associated with other EGFR-targeting monoclonal antibodies have not been observed with nimotuzumab and may be due to binding that is restricted to cells expressing moderate to high levels of EGFR.

An alternative approach to eliminate EGFR+ tumor cells was the use of bispecific T cell engager such as BiTE constructs described in Lutterbüse et al. (PNAS 2010, 107 (28), p 12605). However, this type of approach showed that the simple change of the mode of action from the receptor blockade toward an elimination of target cells via recruitment of immune cells and thereby killing the target cells was not successful to avoid severe side effects since already after administration of relatively low doses in μg/kg/d range experiments with cynomolgus monkeys had to be terminated because of the observation of severe liver and kidney toxicity.

SUMMARY OF THE INVENTION

Thus, a problem of the invention is to provide an EGFR-targeting therapeutic agent with a tumor-specific killing capability and with reduced or no effect on phosphorylation resulting in minor to no skin toxicity.

The problem is solved by the subject matter defined in the claims.

Provided are EGFR/CD16A antigen-binding proteins for a natural killer (NK) cell-based EGFR-targeting approach showing no or only little inhibitory effect on EGF-induced EGFR phosphorylation (Example 6). This suggests that EGFR/CD16A antigen-binding protein provided herein exhibits reduced toxicity in tissues dependent on EGFR signaling for tissue homeostasis, e.g. the skin.

The effects on EGF-mediated phosphorylation of EGFR should be associated with intrinsic properties of the particular 3D structure of the antigen-binding proteins.

Further, the antigen-binding site for EGFR described herein also binds to EGFRvIII (Example 3). Thus, the EGFR/CD16A antigen-binding protein can be used for the treatment of both, EGFR-expressing and EGFRvIII-expressing cancers. EGFRvIII in contrast to EGFR is expressed exclusively on cancer cells but not on healthy tissue. Hence, a broader variety of EGFR- and/or EGFRvIII-positive tumors and, thus, a broader patient population can be targeted with the EGFR/CD16A antigen binding protein described herein.

The invention provides different multispecific, in particular bispecific, NK-cell engaging antigen-binding proteins with different pharmacokinetic (PK) properties designed to redirect NK-cell-mediated killing to EGFR-positive and/or EGFRvIII-positive tumors. Different bispecific EGFR/CD16A antigen-binding proteins targeting human and cynomolgus EGFR and CD16A were designed using Fv antibody binding domains and various antibody or antibody fragment fusion formats.

Increased serum half-life is favorable for in vivo applications. The EGFR/CD16A antigen-binding proteins have varying serum half-lifes, including antibodies with a pharmacokinetic (PK) profile which allows for dosing comparable to IgG-based antibodies. Despite extending the serum half-life the Fc-fusion antigen-binding proteins described herein are also responsible for an improved safety profile, for example reduced skin toxicity, compared to other EGFR-targeting therapies provided by the particular 3D conformation of the selected Bi-scFv-Fc and scFv-IgAb antigen-binding proteins. Hence, the invention provides antigen-binding proteins having a similar pharmacokinetic profile as a monoclonal antibody, but has in addition an improved safety profile.

When the NK-cell via its CD16A receptor is engaged by the multispecific antigen-binding protein with an EGFR-positive tumor cell (via its EGFR antigen) it forms an immunological synapse, which generates a strong activating signal. Simultaneous engagement of the multispecific antigen-binding protein with the NK-cell via its CD16A receptor and a tumor cell via EGFR induces CD16A-mediated NK-cell activation and the formation of an immunological synapse resulting in polarized exocytosis of lytic granules containing perforin and granzymes, as well as cell surface expression of FasL, TRAIL, and TNF-α, which induces tumor cell death by initiating a succession of further enzyme activities (the caspase cascade) resulting in tumor cell apoptosis (programmed cell death).

Thus, such multispecific antigen-binding protein is able to selectively redirect NK-cell lysis of EGFR positive cancer cells. In contrast, full-length antibodies of the IgG isotype bind through their Fc region activating and inhibitory Fcγ receptors, including CD16A, CD16B (FcγRIIIB), CD32A (FcγRIIA), CD32B (FcγRIIB) and CD64 (FcγRI). However, the antigen-binding protein having specificity for CD16A selectively targets the activating subtype CD16A, which is found on NK-cells and macrophages, but not on neutrophils. Furthermore, the NK-cell engaging antigen-binding protein interacts bivalently with CD16A resulting in approximately 1,000-fold higher affinity compared with regular antibodies.

CD16A is an activating receptor triggering the cytotoxic activity of NK-cells. The affinity of antibodies for CD16A directly correlates with their ability to trigger NK-cell activation. Antigen-binding proteins are provided binding bivalently to CD16A, i.e. with two antigen-binding sites, thereby increasing affinity due to the higher avidity for CD16A. Administration of these antigen-binding proteins will result in no or only minor (skin) toxicity based on the following mode of action:

In an embodiment the multispecific antigen binding protein is a EGFR/CD16A bispecific tandem diabody. In its structure, tandem diabodies, comprise only the variable Fv domains of EGFR and CD16A antigen-binding sites and do not contain an Fc-portion. Due to the lack of an Fc-portion, they are not transported by FcRn from the vascular space to the interstitium in normal tissues and primarily stay in the vascular system. In tumors, appropriate levels of EGFR/CD16A tandem diabodies are reached due to the selective and high permeability of tumor blood vessels for macroproteins like tandem diabodies (enhanced permeability and retention effect [EPR]).

Dosing of EGFR/CD16A tandem diabody every other day in cynomolgus monkeys did not induce any skin toxicity. The absence of an Fc portion in the tandem diabody could be responsible for no, or an at least significantly reduced transfer into normal tissues by FcRn, compared to an IgG or other Fc-containing antibody fragments.

In another embodiment the multispecific antigen binding protein is a bispecific EGFR/CD16A antigen-binding protein comprising an Fc-portion. Due to the presence of an Fc-portion, it may be transported to normal tissues by FcRn. However normal tissues are not infiltrated by NK-cells within the interstitial space making NK cell-mediated killing of normal EGFR-positive cells unlikely. In tumors NK-cells are present in much higher numbers and the antigen-binding protein comprising an Fc-portion will reach appropriate levels due to the EPR effect as explained above for tandem diabodies.

Furthermore, as described in detail, inhibition of EGFR signal transduction by the Fc-portion comprising EGFR/CD16A antigen-binding protein is significantly reduced compared to cetuximab in vitro.

Furthermore, the EGFR/CD16A antigen-binding proteins described herein showed superior potency and efficacy compared to previously known monoclonal antibodies (mAb) or other Fc-enhanced antibodies when tested in cytotoxicity assays. In vivo efficacy of selected antibodies was demonstrated in an A-431 tumor model in humanized mice.

Therefore, the EGFR/CD16A antigen-binding proteins are drug candidates suitable for the treatment of EGFR-expressing cancers and offer a potentially improved safety profile.

INCORPORATION BY REFERENCE

All publications, patents, and patent applications mentioned in this specification are herein incorporated by reference to the same extent as if each individual publication, patent, or patent application is specifically and individually indicated to be incorporated by reference.

DETAILED DESCRIPTION OF THE INVENTION

Figure 1:
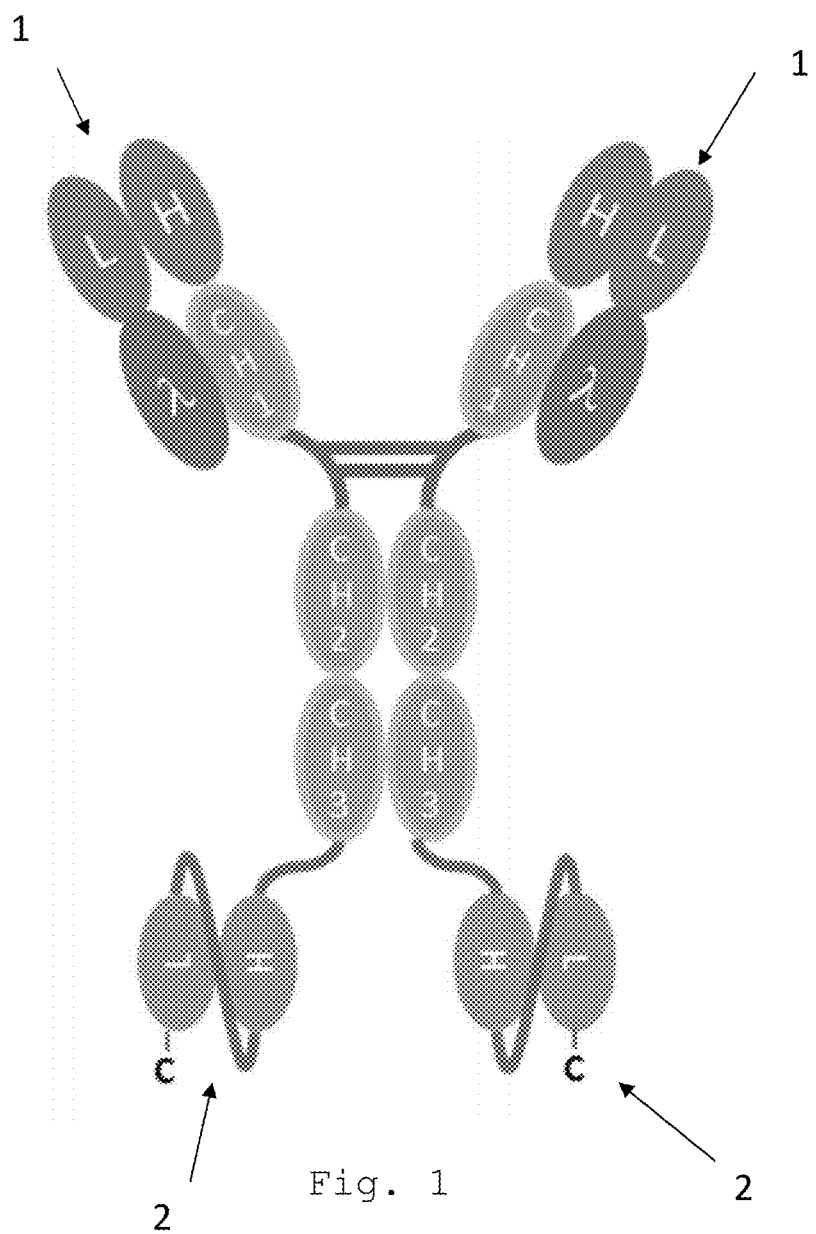
FIG. 1 shows an IgG-like antigen-binding protein with human IgG1 CH1, CH2 and CH3 heavy chain constant domains. The anti-CD16A variable domains are incorporated as antigen-binding sites into the N-terminal Fab-part of the IgG and an anti-EGFR scFv is fused to each polypeptide of the CH2-CH3 homodimer C-terminally (H: variable heavy chain domain; L: variable light chain domain, C: C-terminus, λ: $C_{lambda}$ light chain constant domain, 1: CD16A antigen binding site, 2: EGFR antigen binding site).

The invention relates to a multispecific, e.g., bispecific, antigen-binding protein comprising antigen-binding sites for EGFR and CD16A.

The term "multispecific" refers to an antigen-binding protein, comprising antigen-binding sites that bind to at least two distinct targets, i.e. distinct antigens. "Multispecific" includes, but is not limited to, bispecific, trispecific and tetraspecific. The antigen-binding protein binds at least specifically to the antigens EGFR and CD16A and, thus, is at least bispecific. In certain embodiments the antigen-binding molecule may comprise a third specificity to a third antigen. For example, the third specificity may be an antigen-binding side specifically for serum albumin, in particular human serum albumin (HSA). An example of a trispecific antigen binding protein is tetravalent aTriFlex described below which comprises an antigen binding site specific for EGFR, two antigen binding sites specific for CD16A and one antigen binding site specific for HSA. In other embodiments the third specificity may be a second tumor antigen for making a dual tumor-targeting antigen-binding protein, e.g. the antigen-binding protein may comprise at least one further antigen-binding site for a second tumor antigen, for example HER2, HER3, HER4, c-MET, AXL, FGFR4, VEGF-A, HGF.

The term "antigen-binding protein" refers to an immunoglobulin (Ig) derivative with antigen-binding properties. Preferably, the antigen-binding protein is a human or humanized protein. I.e., the antigen binding protein consists mostly of human sequences from the germline Ig. If the antigen-binding protein is human or humanized, it may comprise single non-human residues or non-human portions, for example in CDRs, linkers or incorporated by mutations. An Ig is a multimeric protein composed of two identical light chain (L) polypeptides and two identical heavy chain (H) polypeptides that are joined into a complex by covalent interchain disulfide bonds. At the N-terminal portion the light chain variable domain (VL) associates with the variable domain (VH) of a heavy chain (H) to form the antigen-binding site of the Ig, the Fv. In addition, each of the light (L) and heavy (H) chains has a constant region. Thus, light (L) chains have one variable (VL) and one constant (CL) domains, e.g. lambda or kappa, and heavy chains (H) have three constant domains designated as CH1, CH2 and CH3. Thus, heavy (H) chains have one variable (VH) and three constant domains (CH1, CH2, CH3). The heavy (H) chain can also be divided in three functional units, the Fd region comprising VH and CH1, the hinge region and the Fc-portion comprising a CH2-CH3 polypeptide chain. The Fc-portion is responsible for effector functions, such as antibody-dependent-cell-mediated cytotoxicity (ADCC), complement-dependent-cytotoxicity (CDC), antibody-dependent cell phagocytosis (ADCP) and binding to Fc receptors, and confers prolonged half-life in vivo (via binding to the neonatal Fc (FcRn) receptor) relative to a polypeptide lacking a Fc-portion. Further, in an IgG homdimer of two CH2-CH3 polypeptide chains associated with each other forms the Fc-region of the antibody. The antigen-binding protein comprises an immunologically functional immunoglobulin portion capable of binding to a target antigen. The immunologically functional immunoglobulin portion may comprise-portions of immunoglobulins (e.g. Fv, Fab), fusion peptides derived from immunoglobulin portions or conjugates combining immunoglobulin portions that form an antigen-binding site. In certain embodiments the antigen-binding site is partly or fully human or humanized. The binding protein comprises antigen-binding sites which are the regions, portions or domains of the binding protein that bind to the target antigens. Each antigen-binding site comprises at least the CDRs of the immunoglobulin heavy or light chains from which the antigen-binding site was derived. The term "antigen-binding protein" refers in some embodiments to antibody derivatives or antibody-like binding proteins that retain specificity and affinity for their antigen including, for example, IgG-like or non-IgG-like fusion peptides based on antigen-binding sites fused to a Fc-portion from any Ig class, in particular from an IgG subclass, such as IgG1, comprising at least a CH2, in some embodiments a CH2-CH3 polypeptide chain, particularly a homodimer of two CH2-CH3 polypeptide chains. The constant region may comprise the complete Ig constant region, i.e. CH1-Hinge-CH2-CH3, or only a Fc-portion, i.e. CH2-CH3 domains, e.g. scFv-IgAb, Bi-scFv-Fc or Fc-scFv as described herein. In other embodiments antigen-binding protein refers to antibody derivatives based on Fv domains either without or with additional constant domains, e.g. Fv fragments, single-chain Fv, tandem single-chain Fv ((scFv)$_2$), Bi-specific NK-cell engagers (BiKE), dual affinity retargeting antibodies (DART™), diabody, single-chain diabody and tandem diabody (TandAb®); aTriFlex, triabody, tribody or Tri-specific NK-cell engagers (TriKE). The variety of antigen-binding protein scaffolds is reviewed in Brinkmann and Kontermann, mAbs, 2017, 9(2):182-192 or in Spiess et al., 2015, Molecular Immunology, 67:95-106.

The term "antigen-binding site" refers to an antibody-antigen combining site or paratope of the antigen-binding protein that binds, in particular specifically, to an antigenic determinant (epitope) of an antigen. The antigen-binding site can be human or humanized. The antigen-binding site is the binding portion of the antigen-binding protein which is capable of recognizing the antigen and binds specifically to the antigen. The antigen-binding site comprises the variable domains of both the light (VL) and heavy (VH) chains that combine with the antigen, i.e. bind to the epitope of the antigen. In certain embodiments the antigen-binding site may be a single domain (sdAb), e.g. $V_HH$ fragments from camelids or $V_{NAR}$ fragments from cartilaginous fishes.

Each antigen-binding site is formed by an antibody, i.e. immunoglobulin, variable heavy chain domain (VH) and an antibody variable light chain domain (VL) binding to the same epitope, whereas the variable heavy chain domain (VH) comprises three heavy chain complementarity determining regions (CDR): HCDR1, HCDR2 and HCDR3; and the variable light chain domain (VL) comprises three light chain complementary determining regions (CDR): LCDR1, LCDR2 and LCDR3. The variable heavy and light chain domains of an antigen-binding site may be covalently linked with one another, e.g. by a peptide linker, or non-covalently associate with one another to form a Fv antigen-binding site.

A "single-chain variable antibody fragment" or "scFv" comprises an antigen binding site consisting of a heavy chain variable domain (VH) joined via a peptide linker to a light chain variable domain (VL). The scFv can be a polypeptide chain: VL-Linker-VH or VH-Linker-VL from the N- to the C-terminus of the polypeptide chain, (Huston et al., Proc. Natl. Acad. Sci. USA, 1988, 85:5879-83).

The "antigen-binding (Fab) fragment" or "Fab" comprises one constant (CH1, CL) and one variable domain (VH, VL) of each of the heavy (H) and the light (L) chain, wherein the variable domains VH and VL are associated to an antigen-binding site. Two Fab' fragments are joined as a F(ab')$_2$ fragment N-terminally to the Fc-portion via the Hinge-region.

A "linker" is a peptide which links other peptides. Typically, a peptide linker is from 1 to about 50, preferably to about 30, most preferably to about 20 amino acids. The length of the linkers influences the flexibility of the polypeptide chain. The desired flexibility depends on the target antigen density and the accessibility of the target antigen. Longer linkers provide more agile antigen-binding sites. If the linker connecting a VH and VL domain consists of about 12 or more amino acid residues, the polypeptide can fold head-to-tail and form a scFv. In certain embodiments the linker of a VH and a VL in a scFv consists of about 15 to about 25, preferably about 15 to about 20, for example 18 amino acids. Shortening the linker to about 12 or less amino acid residues generally prevents adjacent domains of the same polypeptide chain from interacting with each other. However, such linkers can be employed for fusing a scFv to the Fc-portion. In a particular embodiment the scFv is directly fused to the Fc-portion by a peptide-bound. Regarding the amino acid composition of the linkers, in some embodiments, peptides are selected that do not interfere with the assembly of an antigen-binding site. For example, linkers comprising glycine and serine residues generally provide flexibility and protease resistance. In some embodiments the linker comprises the amino acid sequence $(G_aS_b)_c$, wherein a=1-5, b=1-3 and c=1-8. In particular embodiments the linker may comprise the amino acid sequence $(GGS)_x$, wherein x=1-8 or $(GGGGS)_y$, wherein y=1-5.

The term "polypeptide" or "polypeptide chain" refers to a polymer of amino acid residues linked by amide bonds. The polypeptide chain is, preferably, a single chain fusion protein which is not branched. The antigen-binding protein comprises at least two polypeptide chains. Such an antigen-binding protein is a multimer, e.g. dimer, trimer or tetramer. In certain embodiments such as a tandem diabody or a Bi-scFv-Fc the antigen-binding protein is a homodimer and consists of two identical polypeptide chains. In other embodiments the antigen-binding protein is a heterodimer such as a aTriFlex or a hetero-tetramer such as a scFv-IgAb.

The antigen-binding site specifically binds to EGFR or CD16A.

"EGFR" refers to the epidermal growth factor receptor (EGFR; ErbB-1; HER1 in humans, including all isoforms or variants described with activation mutations and implicated in pathophysiological processes. The EGFR antigen-binding site recognizes an epitope in the extracellular domain of EGFR. In certain embodiments the antigen-binding site specifically binds to human and cynomolgus EGFR. "EGFRvIII" refers to an extracellular domain mutant of EGFR resulting from in-frame deletion of base pairs spanning exons 2-7 of the EGFR coding sequence (Gan H K et al., FEBS 2013, 280:5350-5370).

In a particular embodiment the antigen-binding site for EGFR comprises a heavy and a light chain variable domain specific for EGFR, wherein (i) the heavy chain variable domain (VH) specific for EGFR comprises a heavy chain CDR1 having the amino acid sequence set forth in SEQ ID NO:21; a heavy chain CDR2 having the amino acid sequence set forth in SEQ ID NO:22; a heavy chain CDR3 having the amino acid sequence set forth in SEQ ID NO:23 and the light chain variable domain (VL) specific for EGFR comprises a light chain CDR1 having an amino acid sequence set forth in SEQ ID NO:24; a light chain CDR2 having an amino acid sequence set forth in SEQ ID NO:25; and a light chain CDR3 having an amino acid sequence set forth in SEQ ID NOs:26; or
- (ii) the heavy chain variable domain (VH) specific for EGFR has an amino acid sequence as set forth in SEQ ID NOs:1; and/or
- (iii) the light chain variable domain (VL) specific for EGFR has an amino acid sequence as set forth in SEQ ID NO:2.

This antigen-binding site for EGFR also binds to EGFRvIII (Example 3). The use of this antigen-binding site in therapeutics thereby allows treatment of both, EGFR-expressing and EGFRvIII-expressing cancers. EGFRvIII in contrast to EGFR is expressed exclusively on cancer cells but not on healthy tissue. Other EGFR-targeting therapies might be less effective in EGFRvIII-positive cancers due to the enhanced tumorigenicity and constitutive activation of the EGFR signaling pathway by EGFRvIII.

"CD16A" refers to the activating receptor CD16A, also known as FcγRIIIA, expressed on the cell surface of NK-cells. CD16A is an activating receptor triggering the cytotoxic activity of NK-cells. The affinity of antibodies for CD16A directly correlates with their ability to trigger NK-cell activation, thus higher affinity towards CD16A reduces the antibody dose required for activation. The antigen-binding site of the antigen-binding protein binds to CD16A, but not to CD16B. For example, an antigen-binding site comprising heavy (VH) and light (VL) chain variable domains binding to CD16A, but not binding to CD16B, may be provided by an antigen-binding site which specifically binds to an epitope of CD16A which comprises amino acid residues of the C-terminal sequence SFFPPGYQ (SEQ ID NO:3) and/or residues G130 and/or Y141 of CD16A (SEQ ID NO:4) which are not present in CD16B. In some embodiments the CD16A antigen-binding site comprises a heavy and a light variable chain domain specific for CD16A, wherein (i) the heavy chain variable domain (VH) specific for CD16A comprises a heavy chain CDR1 having the amino acid sequence set forth in SEQ ID NO:5; a heavy chain CDR2 having the amino acid sequence set forth in SEQ ID NO:6 or 11; a heavy chain CDR3 having the amino acid sequence set forth in SEQ ID NO:7 and the light chain variable domain (VL) specific for CD16A comprises a light chain CDR1 having an amino acid sequence set forth in SEQ ID NO:8; a light chain CDR2 having an amino acid sequence set forth in SEQ ID NO:9; and a light chain CDR3 having an amino acid sequence set forth in SEQ ID NOs:10; or
- (ii) the heavy chain variable domain (VH) specific for CD16A has an amino acid sequence set forth in SEQ ID NOs:12 or 14; and/or
- (iii) the light chain variable domain (VL) specific for CD16A has the amino acid sequence set forth in SEQ ID NO:13.

This antigen-binding site for CD16A does not bind to CD16B and binds to the known CD16A allotypes F158 and V158 with similar affinity. Two allelic single nucleotide polymorphisms have been identified in human CD16A altering the amino acid in position 158, which is important for interaction with the hinge region of IgG. The allelic frequencies of the homozygous 158 F/F and the heterozygous 158 V/F alleles are similar within the Caucasian population, ranging between 35 and 52% or 38 and 50%, respectively, whereas the homozygous 158 V/V allele is only found in 10-15% (Lopez-Escamez J A et al.; BMC Med Genet 2011; 12:2). Activation of NK-cells by this anti-CD16A domain in all patients due to the similar affinity is therefore advantageous. Further CD16A antigen-binding sites comprising heavy and light variable chain domains that bind to CD16A, but not to CD16B are described in WO 2006/125668.

In alternative embodiments, the heavy and light chain domains incorporate immunologically active homologues or variants of the CDR or framework sequences described herein. Accordingly, in some embodiments, a CDR sequence in a heavy or light chain domain that binds to CD16A or EGFR is similar to, but not identical to, the amino acid sequence depicted in SEQ ID NOs:5-11 or 21-26. In certain instances, a CDR variant sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of 5-11 or 21-26 and which is immunologically active.

In other instances, a CDR variant sequence is modified to change non-critical residues or residues in non-critical regions. Amino acids that are not critical can be identified by known methods, such as affinity maturation, CDR walking mutagenesis, site-directed mutagenesis, crystallization, nuclear magnetic resonance, photoaffinity labeling, or alanine-scanning mutagenesis.

The antigen-binding protein is multivalent. "Multivalent" refers to two or more antigen-binding sites present, e.g. 2, 3, 4, 5, 6, or more. A natural IgG antibody has two binding sites and is bivalent. The multispecific antigen-binding protein has at least four antigen-binding sites and is at least tetravalent. In certain embodiments the antigen-binding protein has two antigen-binding sites for EGFR and two antigen-binding sites for CD16A, i.e. the antigen-binding protein binds bivalently to EGFR and bivalently to CD16A.

Figure 3:
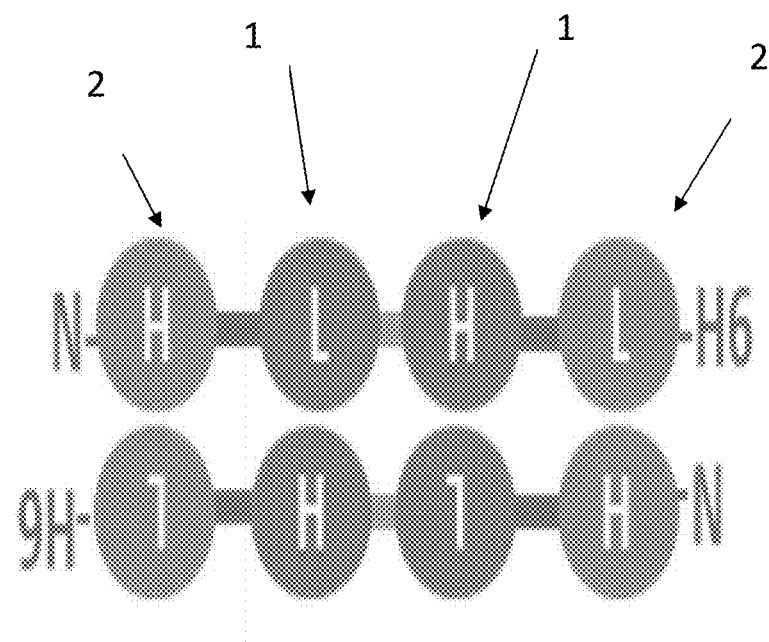
FIG. 3 shows a bispecific EGFR/CD16A tandem diabody consisting of two polypeptide chains, wherein in each polypeptide chain the light chain (L) and heavy chain (H) variable domains are linked one after another by peptide linkers and two of these polypeptides are non-covalently associated with each other, thereby forming a tetravalent antigen-binding protein (N: N-terminus; H6: hexahistidine tag, 1: CD16A antigen binding site, 2: EGFR antigen binding site).

In one embodiment the scaffold of the EGFR/CD16A antigen-binding protein is provided by a tandem diabody (FIG. 3). The term "tandem diabody" refers to an antigen-binding protein constructed by linking at least four variable domains (two heavy chain variable domains (VH) and two light chain variable domains (VL)) in a single polypeptide associated with another identical polypeptide to an antigen-binding homodimer. In such tandem diabodies the linker length is such that it prevents intramolecular pairing of the variable domains so that the polypeptide chain cannot fold back upon itself to form a monomeric single-chain protein, but rather is forced to pair with the complementary domains of another chain. The variable domains are also arranged such that the corresponding variable domains pair during this dimerization (Weichel et al., 2015, European Pharmaceutical Review, 20(1):27-32). Hence, a tandem diabody is an antigen-binding protein, wherein in each polypeptide chain the variable domains are linked one after another by peptide linkers L1, L2 and L3 and positioned within each of the two polypeptide chains from the N-terminus to the C-terminus in the order:
- (i) VH-L1-VL-L2-VH-L3-VL, or
- (ii)VL vl-L1-VH-L2-VL-L3-VH, In a particular embodiment the variable domains in the center of the polypeptide chain linked by linker L2 are specific for CD16A and the peripheral domains at the N- and C-terminus, respectively, are specific for EGFR. In such embodiment the variable domains are positioned within each polypeptide chain from the N-terminus to the C-terminus in the order:
- (i) VH(EGFR)-L1-VL(CD16A)-L2-VH(CD16A)-L3-VL (EGFR), or
- (ii)VL(EGFR)-L1-VH(CD16A)-L2-VL(CD16A)-L3-VH (EGFR), In a preferred embodiment the variable domains are positioned in the order: (i) VH(EGFR)-L1-VL(CD16A)-L2-VH(CD16A)-L3-VL(EGFR).

The length of the linkers influences the flexibility of such multispecific antigen-binding protein according to reported studies. The length of the peptide linkers L1, L2 and L3 in a tandem diabody are "short", i.e. consist of 0, 1, 2, 3, 4, 5, 6, 7, 8, 9, 10, 11 or 12 amino acid residues that the variable domains of a polypeptide chain associate intermolecularly with the domains of another polypeptide to form a tandem diabody. Thus, in certain instances, the linkers consist of about 12 or less amino acid residues, for example 3-12, 3-10, or 3-9 amino acid residues.

Following expression from the single gene construct, two identical polypeptide chains fold head-to-tail to form a functional non-covalent homodimer of approximately 105 kDa. Despite the absence of intermolecular covalent bonds, the homodimer is highly stable once formed, remains intact and does not revert back to the monomeric form. Tandem diabodies contain only antibody variable domains and lack constant domains. Tandem diabodies allow for bivalent binding to CD16A and bivalent binding to EGFR. The size of a tandem diabody, at approximately 105 kDa, is smaller than that of an IgG, but is well above the threshold for first-pass renal clearance, offering a pharmacokinetic advantage compared with smaller bispecific formats based on antibody-binding domains or non-antibody scaffolds. Moreover, tandem diabodies are advantageous over other bispecific binding proteins such as BiTE® or DART™ molecules based on these pharmacokinetic and avidity properties resulting in longer intrinsic half-lives and enhanced cytotoxicity. Tandem diabodies are well expressed in host cells, for example, mammalian CHO cells. It is contemplated that robust upstream and downstream manufacturing process is available for tandem diabodies.

Figure 4:
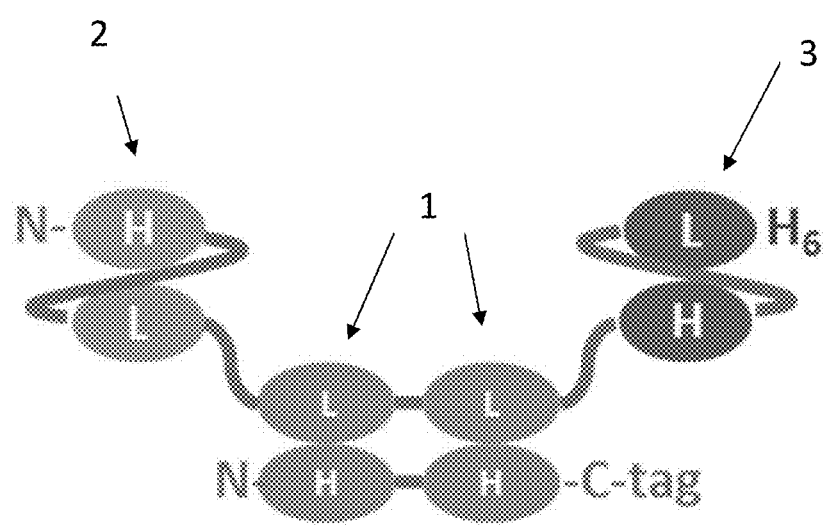
FIG. 4 shows a trispecific EGFR/CD16A/HSA aTriFlex antigen-binding protein consisting of a first polypeptide comprising N-terminally an anti-EGFR scFv-unit fused to an anti-CD16A diabody-unit and C-terminally an anti-HSA scFv-unit fused to the CD16A diabody-unit (H: variable heavy chain domain; L: variable light chain domain; N: N-terminus; H6: hexahistidine tag, 1: CD16A antigen binding site, 2: EGFR antigen binding site, 3: HSA antigen binding site).

In another embodiment the antigen-binding protein is an asymmetric, trispecific flexibody (aTriFlex) as disclosed in WO 2017/064221. Such aTriFlex is a dimer of a first polypeptide comprising at least six variable domains and a second polypeptide comprising at least two variable domains (FIG. 4). In such embodiment the second polypeptide is part of a diabody unit and is, preferably non-covalently, associated with the other pair of two juxtaposed variable domains integrated into the first polypeptide. In embodiments where the first polypeptide chain consists of six variable domains and the second polypeptide consists of two variable domains the variable domains may be arranged from the N-terminus to the C-terminus of the polypeptides, for example, in the following orientations: $V_H$-$V_L$-$V_H$-$V_H$-$V_L$-$V_H$ (first polypeptide) and $V_L$-$V_L$ (second polypeptide); $V_L$-$V_H$-$V_H$-$V_H$-$V_H$-VL (first polypeptide) and $V_L$-$V_L$ (second polypeptide); $V_H$-$V_L$-$V_L$-$V_L$-$V_H$-VL (first polypeptide) and $V_H$-$V_H$ (second polypeptide); $V_L$-$V_H$-$V_L$-$V_L$-$V_H$-$V_L$ (first polypeptide) and $V_H$-$V_H$ (second polypeptide) or $V_H$-$V_L$-$V_L$-$V_L$-$V_L$-$V_H$ (first polypeptide) and $V_H$-$V_H$ (second polypeptide). Diabody units having one pair of the two variable domains in the orientation $V_H$-$V_H$ and the other pair of the two variable domains in the orientation $V_L$-$V_L$ favor the correct folding, in particular of multispecific, e.g. trispecific, antibody molecules. In preferred embodiments the variable domains specific for CD16A are positioned in the center of the first polypeptide chain consisting of six variable domains and the second polypeptide consists of the complementary variable domains specific for CD16A. Such aTriFlex is tetravalent and bispecific or trispecific. In an embodiment the aTriFlex is trispecific and comprises one antigen-binding site for EGFR, two antigen-binding sites for CD16A and one antigen-binding site for HSA (human serum albumin). In a particular embodiment the aTriFlex consists of a first polypeptide chain having the variable domains positioned in the order (i) VH(EGFR)-VL(EGFR)-VL(CD16A)-VL(CD16A)-VH(HSA)-VL(HSA) and a second polypeptide chain having the variable domains positioned in the order VH(CD16A)-VH(CD16A) or (ii) VH(EGFR)-VL(EGFR)-VH(CD16A)-VH(CD16A)-VH(HSA)-VL(HSA) and a second polypeptide chain having the variable domains positioned in the order VL(CD16A)-VL(CD16A). The generation and production of such aTriFlex antigen-binding protein is described in WO 2017/064221.

In further embodiments the antigen-binding protein is an Fc-fusion protein comprising immunoglobulin constant domains of an immunoglobulin selected from the classes of IgG, IgM, IgA, IgD and IgE and scFvs comprising antigen-binding sites attached thereto. Preferred are constant domains of IgG, in particular IgG1. Hence, in some embodiments the Fc-fusion antigen-binding protein comprises an Fc-portion. Due to binding of the Fc-portion to FcRn the serum half-life of the Fc-fusion antigen-binding protein is significantly increased relative to Fv-domain based antigen-binding proteins, such as, for example, tandem diabody or aTriFlex.

"Fc-fusion antigen-binding protein" refers to antigen-binding proteins comprising a combination of an Fc-portion of an immunoglobulin and at least one antigen-binding site fused N-terminally and/or C-terminally to the Fc-portion. The invention provides a multispecific and at least tetravalent Fc-fusion antigen-binding protein having two antigen-binding sites attached to the N-termini and two antigen-binding sites attached to the C-termini of the Fc-portion. The two antigen-binding sites attached to the N-termini may be antigen-binding Fab's or scFv's joined via a Hinge domain to the N-terminus of CH2 of the Fc-portion. Each of the two antigen-binding sites placed upon the C-termini is a scFv fused by a peptide linker to the C-terminus of CH3 of the Fc-portion. In some embodiments the two antigen-binding sites placed upon the N-termini of the Fc portion are specific for a first antigen and the two antigen-binding sites placed upon the C-termini are specific for a second antigen. Hence, the tetravalent antigen-binding molecule binds bivalently to the first antigen and bivalently to the second antigen, whereas this bivalent binding increases the avidity and, thereby, the binding affinity to each of the two antigens. In a particular embodiment the antigen-binding sites placed upon the N-termini of the Fc-portion are specific for CD16A and the antigen-binding sites placed upon the C-termini of the Fc-portion are specific for EGFR.

"Fc-portion" refers to a polypeptide retaining at least one functionality of an Fc-region of the constant Ig region, in particular the function of binding to FcRn, and comprises at least a CH2 domain, preferably a CH2-CH3 polypeptide chain. The CH2-CH3 polypeptide chain assembles with another CH2-CH3 polypeptide chain to a homodimer of two CH2-CH3 polypeptides combined with one another, wherein the dimerization is promoted by the Hinge region C-terminal to the CH2 domain. Hence, in some embodiments the Fc-portion comprises a homodimer of two CH2-CH3 polypeptide chains and a Hinge region. Preferably, the Fc-portion comprises constant domains of the IgG class, in particular IgG1 constant domains.

Further, a "Hinge domain" may be joined N-terminally to a Fc-portion. The Hinge domain may be of the same or different IgG class as the Fc-portion or an engineered, not naturally occurring Hinge domain.

Such Fc-fusion antigen-binding proteins can be generated by a modular combining of antigen-binding sites for CD16A and EGFR with a preferably IgG1 Fc-portion such that two antigen-binding sites are fused either as Fab-fragment or as scFv via a Hinge domain N-terminally to the Fc-portion and two scFv antigen-binding sites are fused C-terminally to the Fc-portion, thereby providing bispecific and tetravalent antigen-binding proteins.

Figure 2:
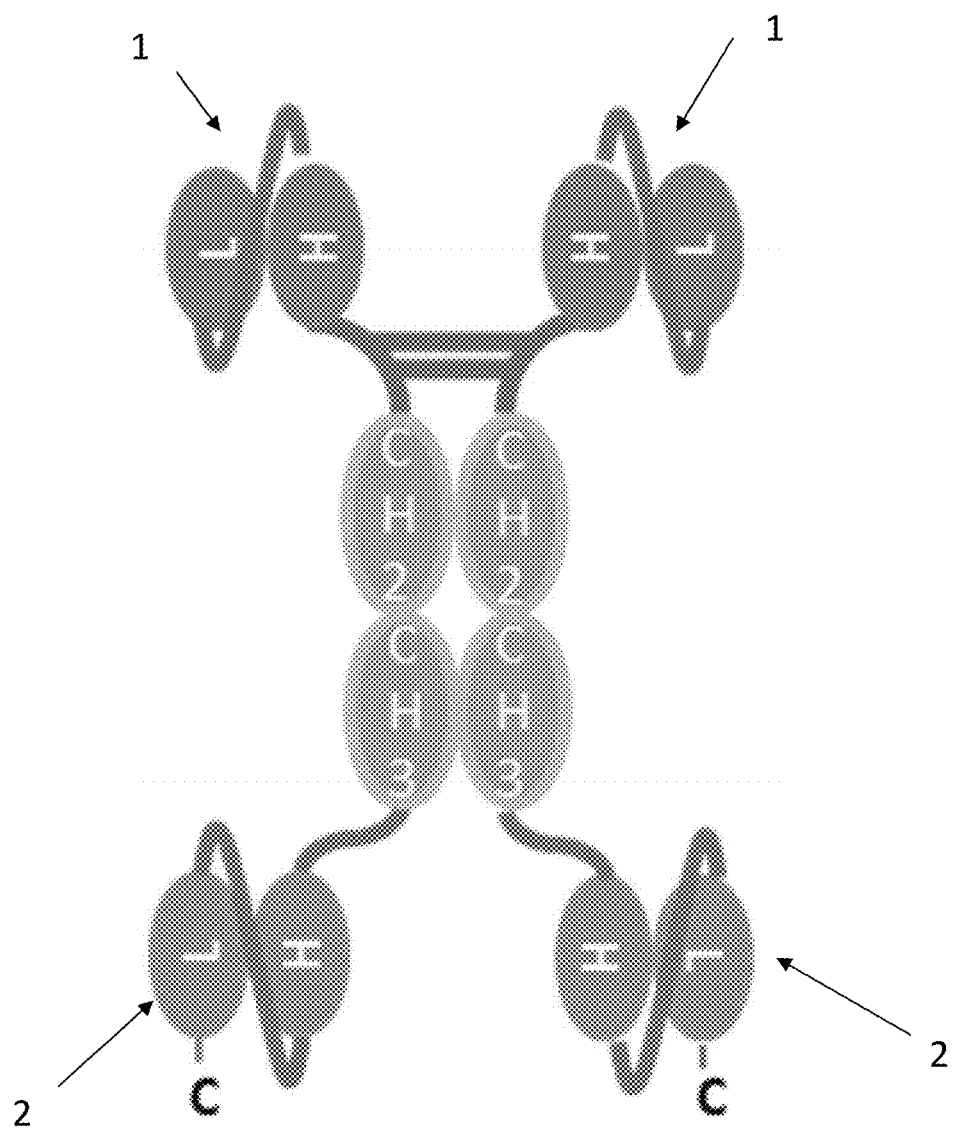
FIG. 2 shows a scFv-Fc fusion antigen-binding protein with a homodimer of two CH2-CH3 polypeptides. In each polypeptide a CD16A scFv unit is fused by the hinge region N-terminally to the CH2 and an anti-EGFR scFv is fused to the CH2-CH3 homodimer C-terminally (H: variable heavy chain domain; L: variable light chain domain, C: C-terminus, 1: CD16A antigen binding site, 2: EGFR antigen binding site).

In some embodiments the Fc-fusion antigen-binding protein is a scFv-IgAb (FIG. 1) or a Bi-scFv-Fc (FIG. 2).

Hence, in a further embodiment the multispecific antigen-binding protein is a tetravalent and bispecific Fc-fusion protein (Bi-scFv-Fc) (FIG. 2) comprising an homodimer of two CH2-CH3 polypeptides and each of the two CH2-CH3 polypeptides is N-terminally and C-terminally fused to a scFv comprising the variable heavy chain (VH) domain and variable light chain (VL) domain covalently joined by a flexible linker for forming an antigen-binding site of the scFv. Hence, such Bi-scFv-Fc antigen-binding protein consists of two polypeptide chains and each polypeptide comprises a first single-chain Fv (scFv(1)) consisting of a VL linked by a peptide linker to a VH of a first antigen-binding site, that scFv(1) is fused by a hinge region N-terminally to a CH2 domain of a CH2-CH3 polypeptide chain and a second single-chain Fv (scFv(2))consisting of a VL linked by a peptide linker to a VH of a second antigen-binding site that is fused by a peptide linker C-terminally to the CH3 domain of the CH2-CH3 polypeptide chain. Thus, such Bi-scFv-Fc antigen-binding protein consists of two polypeptide chains having the structure from the N- to the C-terminus: scFv(1)-Hinge-CH2-CH3-scFv(2). In particular, (i) scFv(1) is an antigen-binding site for CD16A and scFv(2) is an antigen-binding site for EGFR or (ii) scFv(1) is an antigen-binding site for EGFR and scFv(2) is an antigen-binding site for CD16A. Preferably, the Fc-portion consisting of the CH2-CH3 homodimer is silenced, i.e. does essentially not bind to Fc-gamma receptor but retains binding to FcRn. In a particular embodiment the antigen-binding protein comprises CH2-CH3 heavy chain constant domains having the amino acid sequence as depicted in SEQ ID NO:20.

In a further embodiment the multispecific Fc-fusion antigen-binding molecule is a tetravalent and bispecific scFv-Ig antigen-binding protein (scFv-IgAb; FIG. 1). Such scFv-IgAb consists of an IgG, preferably IgG1, scaffold and two scFvs fused thereto C-terminally. Hence, such scFv-IgAb is assembled from two heavy (H) and two light (L) chains. The heavy (H) chain consists of a variable heavy chain (VH) domain joined C-terminally to a CH1 domain which is linked by a Hinge region C-terminally to a CH2-CH3 polypeptide chain and the CH3 domain is fused to a scFv comprising an antigen-binding site having a variable light chain (VL) domain linked by a flexible linker to a variable heavy (VH) domain. The light (L) chain consists of a variable light chain (VL) domain joined to a light chain constant domain (CL), such as lambda or kappa light chain constant domain. The scFv-IgAb antigen-binding protein is assembled from two heavy (H) and two (L) chains, wherein the variable domains of the heavy (VH) and the light (VL) chain associate to form N-terminally two Fv antigen-binding sites of Fab's. In one embodiment the N-terminal Fv antigen-binding sites of the Fab's are specific for CD16A and the C-terminal scFv antigen-binding sites are specific for EGFR. In another embodiment the N-terminal Fv antigen-binding sites of the Fab's are specific for EGFR and the C-terminal scFv antigen-binding sites are specific for CD16A. Particularly, the multispecific antigen-binding protein comprises a heavy (H) chain and a light (L) chain, wherein (i) the heavy (H) chain has the structure VH(CD16A)-CH1-Hinge-CH2-CH3-VH(EGFR)-VL (EGFR) and the light chain has the structure VL(CD16A)-CL or (ii) the heavy chain has the structure VH(EGFR)-CH1-Hinge-CH2-CH3-VH(CD16A)-VL(CD16A) and the light chain has the structure VL(EGFR)-CL or (iii) VH(EGFR)-CH1-CH2-CH3-VL(CD16A)-VH(CD16A) and the light chain has the structure VL(EGFR)-CL. In some embodiments the Fc-portion consisting of the CH2-CH3 homodimer is silenced, i.e. does essentially not bind to FcγR but retains binding to FcRn.

In some embodiments the antigen-binding protein comprises a silenced Fc-portion. Such Fc-portion is silenced in binding to FcγR compared to an IgG. In a particular embodiment the antigen-binding protein comprises a heavy chain constant domain having the amino acid sequence as depicted in SEQ ID NO:15 and/or a lambda light chain domain having the amino acid sequence as depicted in SEQ ID NO:16.

"Silenced Fc-portion" refers to a modified Fc-portion which does not bind to Fc-gamma receptor (FcγR), but retains binding to the neonatal Fc receptor (FcRn) for extended half-life and long serum persistence. The antigen-binding protein is designed to engage NK-cells specifically via the CD16A antigen and, thus, in preferred embodiments Fc binding to Fc-gamma receptor should be prevented. In addition, FcRn has been reported to protect IgG from degradation and being responsible for transport of IgG across epithelial barriers. Hence, modifications in the Fc-portion of Fc-fusion antigen-binding proteins which retain or enhance FcRn binding are preferred.

Several sets of mutations or changes to generate an IgG1 with reduced or no binding to Fc-gamma receptor have been described which are selected from the mutations of the group consisting of: C220S, C229S, E233P, L234A, L234V, L234F, L235A, L235E, P238S, D265A, N297A, N297Q, P331S; or mutations for generating an IgG2 with reduced binding to Fc-gamma receptor which can be selected from the group consisting of: H268Q, V309L, A330S, A331S or mutations for generating an IgG4 with reduced binding to Fc-gamma receptor which can be selected from the group consisting of: L235A, G237A, E318A (Strohl W., Current Opinion in Biotechnology 2009, 20:1-7; Kaneko E and Niwa R, Biodrugs 2011, 25(1):1-11; Baudino L., J. Immunology 2008, 181:6664-6669).

Further, the Fc-portion may be engineered to extend serum half-life. The following mutations in the IgG1 Fc-portion that increase serum half-life of the antigen-binding protein have been described: T250Q, M252Y, S254T, T256E, T307A, E380A, M428L, H433K, N434A, N434Y (Srohl W., Current Opinion in Biotechnology 2009, 20:1-7; Borrok M J, et al., J. Pharmaceutical Sciences 2017, 106 (4):1008-1017).

In some embodiments the IgG1 Fc-portion comprises a set of mutations at positions 234, 235 and 265 according to the Kabat numbering, in particular the set of mutations is selected from L234F/V/A, L235A/E and D265A. Particularly preferred is an IgG1 Fc-portion comprising the set of mutations L234F, L235E and D265A (SEQ ID NO:20). Accordingly, in some embodiments the Fc-fusion antigen binding molecule, such as Bi-scFv-Fc or scFv-IgAb, comprises a silenced IgG1 Fc-portion with the set of mutations L234F, L235E and D265A. All recited mutations correspond to the Kabat numbering system (Kabat, E. A. et al., Sequences of proteins of immunological interest. 5th Edition—US Department of Health and Human Services, NIH publication n° 91-3242, pp 662,680,689 (1991).

In alternative embodiments serum half-life of the EGFR/CD16A antigen-binding protein may be extended by (i) fusing at least one antigen-binding site for human serum albumin (HSA) to the antigen-binding protein or (ii) fusing or joining human serum albumin (HSA) to the antigen-binding protein.

The antigen-binding protein according to any one of the embodiments described herein may be produced by expressing polynucleotides encoding the individual polypeptide chains which form the antigen-binding protein. Therefore, further embodiments of the invention are polynucleotides, e.g. DNA or RNA, encoding the polypeptides of the antigen-binding protein as described herein above. The polynucleotides may be constructed by methods known to the skilled person, e.g. by combining the genes encoding the variable domains and the constant domains separated by peptide linkers or directly linked by a peptide bond of the polypeptide chains, into a genetic construct operably linked to a suitable promoter, and optionally a suitable transcription terminator, and expressing it in bacteria or other appropriate expression system such as, for example CHO cells (Example 1).

The invention further provides the multispecific antigen-binding protein, in particular, a composition comprising a multispecific antigen-binding molecule as described herein above and at least one further component.

In a further embodiment the multispecific antigen-binding protein of the invention is for use as a therapeutic compound. Preferably, the multispecific antigen-binding protein according to the invention is for use in the treatment of a cancer characterized by EGFR-positive or EGFRvIII-positive cells.

In another embodiment of the invention a method for the treatment or amelioration of a proliferative disease or a tumorous disease is provided, wherein the method comprises a step of administering to a subject in need thereof the multispecific antigen-binding protein according to the invention. The subject to be treated can be human. In a particular embodiment of the invention the proliferative disease or tumorous disease is characterized by EGFR-positive or EGFRvIII-positive cells.

For use as a therapeutic compound or for treating an EGFR-positive disease or EGFR-positive and/or EGFRvIII-positive cancer the composition comprising the multispecific antigen binding protein is preferably combined with a suitable pharmaceutically acceptable carrier. The term "pharmaceutically acceptable carrier" is meant to encompass any carrier, which does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservatives, emulsifying agents and dispersing agents. Prevention of the action of microorganisms may be ensured by the inclusion of various antibacterial and antifungal agents. Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors.

The EGFR-positive and/or EGFRvIII positive cancers that can be treated using the antigen-binding protein of the present invention include but are not limited to for example colorectal cancer, head and neck cancer, lung cancer and glioblastoma The following examples should further illustrate the described embodiments without limiting the scope of the invention. It is demonstrated that the antigen-binding protein according to the invention is capable of inducing NK-cell-mediated cytotoxicity, while having no or little inhibitory effect on EGF-induced EGFR phosphorylation:

Example 1: Generation and Production of EGFR/CD16A Antigen-Binding Proteins

Material

| Product | Supplier | Cat. |
|---|---|---|
| 0.25% Trypsin-EDTA | Life Technologies | 25200 |
| ActiCHO Feed-A CD | GE Healthcare | U15-072 |
| ActiCHO Feed-B CD | GE Healthcare | U05-054 |
| CHO-S-SFMII | Life Technologies | 12052-114 |
| DMSO | Sigma | D2650 |
| DPBS | Life Technologies | 14190 |
| FCS | Life Technologies | 10270-106 |
| Flp-In ™-CHO Cell Line | Life Technologies | R75807 |
| Ham's F-12 Nutrient Mix | Life Technologies | 21765-029 |
| HT-Supplement | Life Technologies | 41065 |
| HyClone CDM4 CHO medium | GE Healthcare | SH30557 |
| Puromycin Dihydrochloride 10 mg/ml in 20 mM HEPES-Puffer | Fisher Scientific | A1113803 |
| L-Glutamine (200 mM) | Life Technologies | 25030 |
| MycoAlert Assay control Set | Lonza | LT07-518 |
| MycoAlert Mycoplasma detection Kit | Lonza | LT07-318 |
| Opti-MEMI | Life Technologies | 31985-047 |
| Penicillin/Streptomycin | Life Technologies | 15140 |
| Phenolred (0.5% solution) | Sigma | P0290 |
| pOG44 | Life Technologies | V600520 |
| Polyethylenimine (PEI), 25 kDa, linear | Polysciences | 23966 |
| Sucrose | Roth | 4621 |
| Zeocin | Life Technologies | R250-01 |

Generation of the EGFR/CD16A Antigen-Binding Proteins
Tandem Diabody

The tandem diabodies (FIG. 3) are constructed as described in Reusch et al., 2014, mAbs 6:3, 728-739. For constructing the tandem diabody the anti-EGFR Fv domains (SEQ ID NOs:1,2) are combined with the anti-CD16A Fv domains (SEQ ID NOs:12,13). The expression cassette for the tandem diabody is cloned such that the anti-EGFR domains and the anti-CD16A domains are positioned in the order VH_EGFR-L1-VL_CD16A-L2-VH_CD16A-L3-VL_EGFR. A 9 amino acid linker $(G_2S)_3$ (SEQ ID NO:36) is used for linkers L1 and L3 and a 6 amino acid linker $(G_2S)_2$ (SEQ ID NO:35) is used for linker L2 Obtained EGFR/CD16A tandem diabody consists of two polypeptides having the amino acid sequence as depicted in SEQ ID NO:27.

aTriFlex

The aTriFlex (FIG. 4) is constructed as described in WO 2017/064221. For constructing the aTriFlex the anti-EGFR Fv domains (SEQ ID NOs:1,2) are combined with the anti-CD16A Fv domains (SEQ ID NOs:12,13) and anti-HSA Fv domains (SEQ ID NOs:31,32). The expression cassette for the aTriFlex is cloned such that the anti-EGFR domains and the anti-CD16A domains are positioned in the first polypeptide: VH_EGFR-L1-VL_EGFR-L2-VL_CD16A-L2-VL_CD16A-L2-VH HSA-L1-VL HSA and in the second polypeptide in the order VH(CD16A)-L2-VH(CD16A) order and a 18 amino acid linker ($G_2S)_6$ (SEQ ID NO:18) is used for linker L1 and a 9 amino acid linker ($G_2S)_3$ (SEQ ID NO:36) is used for linker L2.

Bi-scFv-Fc

For expression of the Bi-scFv-Fc antigen-binding protein (FIG. 2) in CHO cells, coding sequence of the molecule was cloned into the mammalian expression vector system. In brief, gene sequences encoding the anti-EGFR Fv domains (SEQ ID NOs:1,2) and the anti-CD16A Fv domains (SEQ ID NOs:12,13) connected by peptide linkers were synthesized by Thermo Fisher Scientific GeneArt (Regensburg, Germany). PCR-amplicons of the different variable domains and of the Fc portion containing the silencing point-mutations (SEQ ID NO:20) were generated with corresponding primers. Afterwards the different overlapping DNA-fragments and the linearized backbone vector are combined together in one isothermal reaction. The Bi-scFv-Fc expression construct was designed to contain coding sequences for an N-terminal signal peptide and an Fc-portion to facilitate antibody secretion and purification, respectively. The sequence of the construct was confirmed by DNA sequencing at GATC (Koln, Germany) using the primer pair 5'-TAATACGACTCACTATAGGG-3' (SEQ ID NO:33) and 5'-TAGAAGGCACAGTCGAGG-3'(SEQ ID NO:34). The expression cassette for the Bi-scFv-Fc is cloned such that the anti-EGFR domains and the anti-CD16A domains are positioned in the order VL_CD16A-L1-VH_CD16A-Hinge-CH2-CH3-L2-VH_EGFR-L3-VL_EGFR and ($G_2S)_7$ is used for linker L1, ($G_4S)_2$ is used for linker L2 and ($G_2S)_6$ is used for linker L3. Obtained Bi-scFv-Fc-_02 consists of two polypeptides having the amino acid sequence as depicted in SEQ ID NO:30.

scFv-IgAb (FIG. 1):

The DNA expression construct encoding the scFv-IgAb is generated by cloning the encoding sequences of the anti-CD16A Fv domains (SEQ ID NOs:12,13) into a modified mammalian expression vector containing CMV-controlled expression cassettes including heavy and light chain constant domains with Fc silenced point-mutations (SEQ ID NOs:15,16) for co-expression from the same vector. Afterwards PCR amplicons are generated from the gene sequences encoding the anti-EGFR Fv domains (SEQ ID NOs:1,2) separated by a peptide linker having the amino acid sequence as depicted in SEQ ID NO:18 (VH-($G_2S)_6$-VL) with corresponding primers. The resulting overlapping DNA-fragment is inserted into the co-expression vector at the relevant position. All needed gene sequences encoding variable domains and constant domains containing Fc-silenced point-mutations were synthesized by Thermo Fisher Scientific GeneArt (Regensburg, Germany). The scFv-IgAb expression construct was designed to contain coding sequences for N-terminal signal peptides and an Fc portion to facilitate antibody secretion and purification, respectively. Sequences of all constructs were confirmed by DNA sequencing at GATC (Koln, Germany) using custom made primers. The expression cassette for the scFv-IgAb is cloned such that the anti-EGFR domains, the anti-CD16A domains and the constant domains are positioned in the first polypeptide: VH_CD16A-CH1-Hinge-CH2-CH3-L1-VH_EGFR-L2-VL_EGFR and in the second polypeptide in the order VL_CD16A-CLambda. ($G_4S)_2$ (SEQ ID NO:35) is used for linker L1 and($G_2S)_6$ (SEQ ID NO:18) is used for linker L2. Obtained scFv-IgAb_02 consists of the heavy chain having the amino acid sequence as depicted in SEQ ID NO:28 assembled with the light chain having the amino acid sequence as depicted in SEQ ID NO:29.

Host Cell Culture

Flp-In CHO cells (Life Technologies), a derivative of CHO-K1 Chinese Hamster ovary cells (ATCC, CCL-61) (Kao and Puck, 1968), were cultured in Ham's F-12 Nutrient Mix supplemented with L-Glutamine, 10% FCS and 100 µg/ml Zeocin. Adherent cells were detached with 0.25% Trypsin-EDTA and subcultured according to standard cell culture protocols provided by Life Technologies.

For adaptation to growth in suspension, cells were detached from tissue culture flasks and placed in serum-free HyClone CDM4 CHO medium for subsequent incubation in shake flasks at 37° C., 5% $CO_2$ and 120 rpm. The standard medium for the culture of suspension-adapted Flp-In CHO Host cells was HyClone CDM4 CHO supplemented with L-Glutamine, HT Supplement, Penicillin/Streptomycin and 100 µg/mL Zeocin. Suspension-adapted cells were cryopreserved in medium with 10% DMSO and tested negative for *Mycoplasma* using MycoAlert *Mycoplasma* Detection Kit (Lonza).

Generation of Stably Transfected Cell Pools

Recombinant Flp-In CHO cell lines stably expressing secreted recombinant antibodies, Fc fusion constructs or comparator antibodies as well as membrane-anchored antigens were generated by transfection of suspension-adapted host cells. For this, cells were placed in standard medium without Zeocin one day prior to co-transfection with expression plasmids (2.5 µg) encoding the protein of interest (pcDNA5-FRT) and the Flp recombinase (pOG44, Life Technologies) using Polyethylenimine (PEI). In brief, vector DNA and transfection reagent were mixed at a DNA: PEI ratio of 1:3 (µg/µg) in a total of 100 µL OptiMEM I medium and incubated for 10 minutes before addition to 2E+6 Flp-In CHO cells suspended in 1 ml of CHO—S-SFMII medium (Life Technologies). Following 24-48 h incubation, selection for stably transfected cells was started by addition of 6-7 µg/mL Puromycin Dihydrochloride subsequent to diluting cultures to a density of 0.1E+6 viable cells/mL in CHO—S-SFMII medium. Flp recombinase mediates the insertion of the Flp-In expression construct into the genome at the integrated FRT site through site-specific DNA recombination (O'Gorman et al 1991). During selection viable cell densities were measured twice a week, and cells were centrifuged and resuspended in fresh selection medium at a maximal density of 0.1E+6 viable cells/mL. Cell pools stably expressing recombinant protein products were recovered after 2-3 weeks of selection at which point cells were transferred to standard culture medium in shake flasks. Expression of recombinant secreted or membrane-anchored proteins was confirmed by protein gel electrophoresis of cell culture supernatants using Criterion Stain-Free (Bio-Rad) technology (see below) or Flow Cytometry, respectively. Stable cell pools were cryopreserved in medium containing 7.5% DMSO.

Production of Recombinant Protein in Fed-Batch CHO Cell Suspension Cultures

Recombinant proteins were produced in 10- or 11-day fed-batch cultures of stably transfected CHO cells by secretion into the cell culture supernatant. For this, cells stably expressing recombinant antibodies, Fc fusion antigens or comparator antibodies were seeded at starting densities of 6E+5 cells/mL in standard culture medium in polycarbonate Erlenmeyer flasks with gas permeable caps (Corning) and incubated at 37° C. and 5% $CO_2$ with agitation at 140 rpm.

During fed-batch culture, media were supplemented with 40 mL/L ActiCHO Feed A (GE Healthcare) and 4 mL/L ActiCHO Feed B (GE Healthcare) on day 0 (starting day), and with double amounts on day 3, 5, and 7. Cell culture supernatants were harvested after 10 or 11 days at culture viabilities of typically >75%. Samples were collected from the production cultures every other day prior to feeding and cell density and viability was assessed. On the day of harvest, cell culture supernatants were cleared by centrifugation and vacuum filtration (0.22 μm) using Millipore Express PLUS Membrane Filters (Millipore) before further use.

Expression Titer Quantification:

Protein expression titers and product integrity in cell culture supernatants (CSS) are analysed by SDS-PAGE on days 5, 7 and 10 or 11 of production cultures. Samples are mixed with SDS PAGE sample buffer prior to loading on 4-20% Criterion TGX Precast SDS PAGE Gels (Biorad). Total protein is visualized in the gel using the Criterion Stain-free Molecular Imaging System (Biorad). Product titers are determined semi-quantitatively by comparison with reference antibodies of known concentration.

Purification of Anti-EGFR Antibodies

Figure 5:
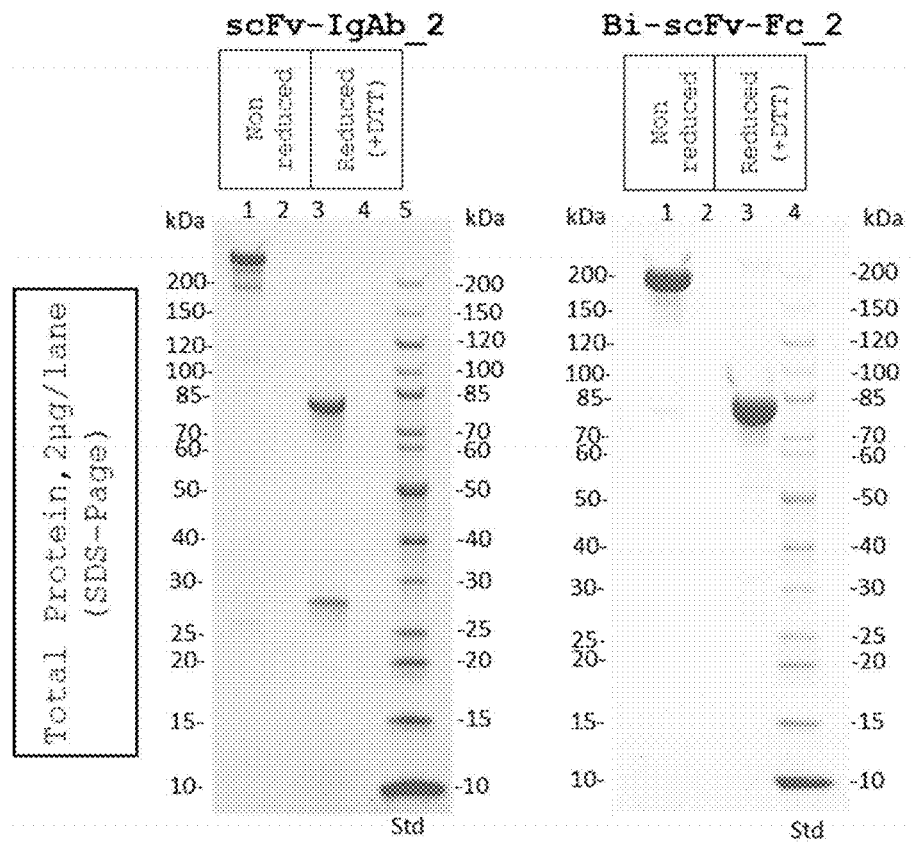
FIG. 5 shows a SDS PAGE gel image, visualized with Stain-free Imaging technology (Bio-Rad)) of scFv-IgAb_02 and Bi-scFv-Fc_02 after purification.
Figure 6:
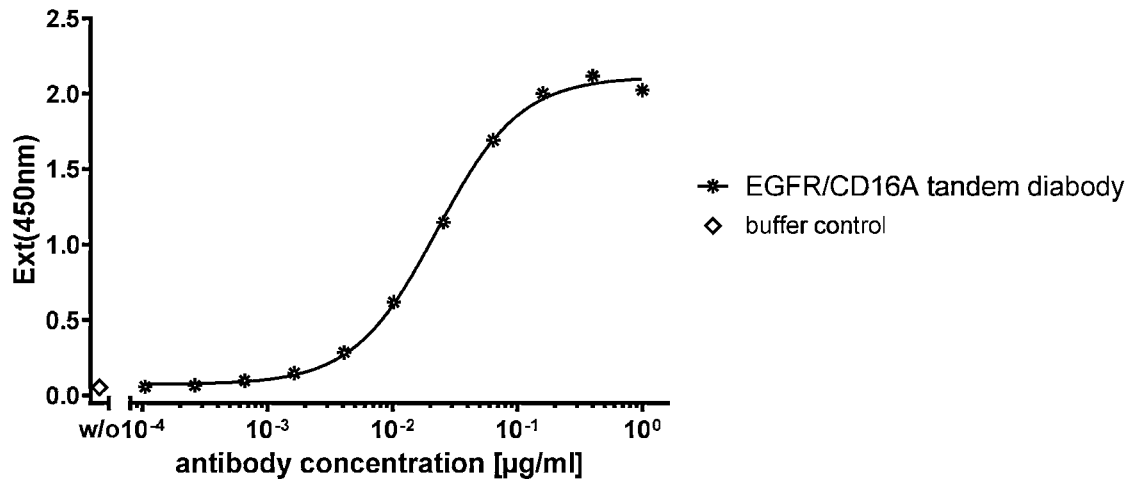
FIG. 6 shows concentration-dependent binding of EGFR/CD16A tandem diabody to (A) EGFR- or (B) CD16A-antigen.
Figure 6:
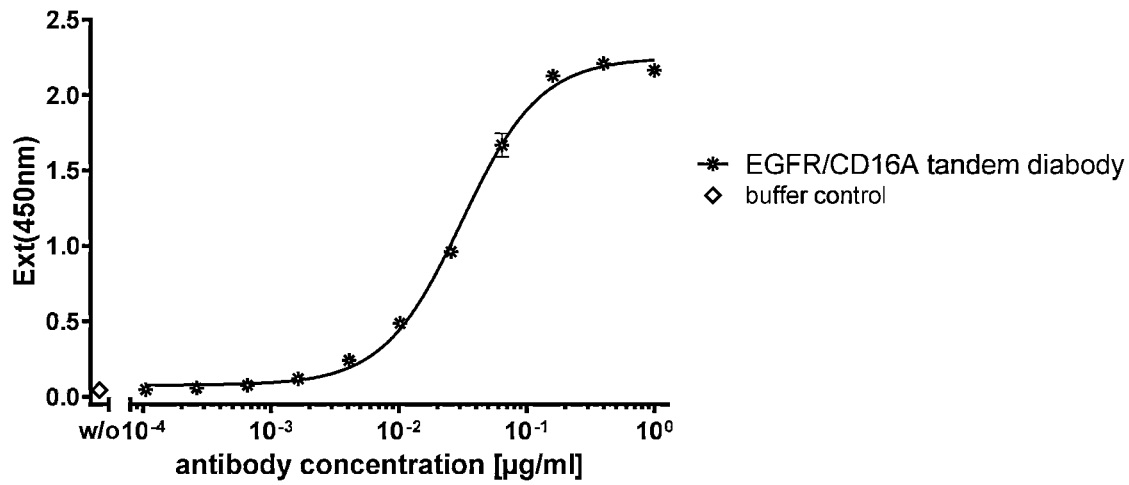
Figure 7:
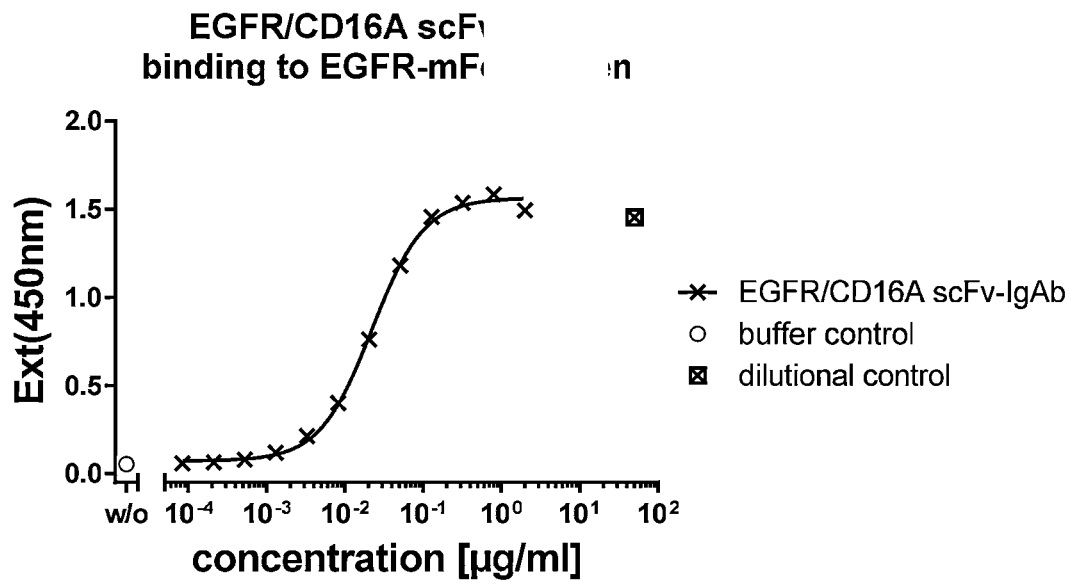
FIG. 7 shows concentration-dependent binding of (A) EGFR/CD16A scFv to monomeric EGFR-mFc, or (B) CD16A- or CD16B-antigen to EGFR/CD16A scFv-IgAb.
Figure 7:
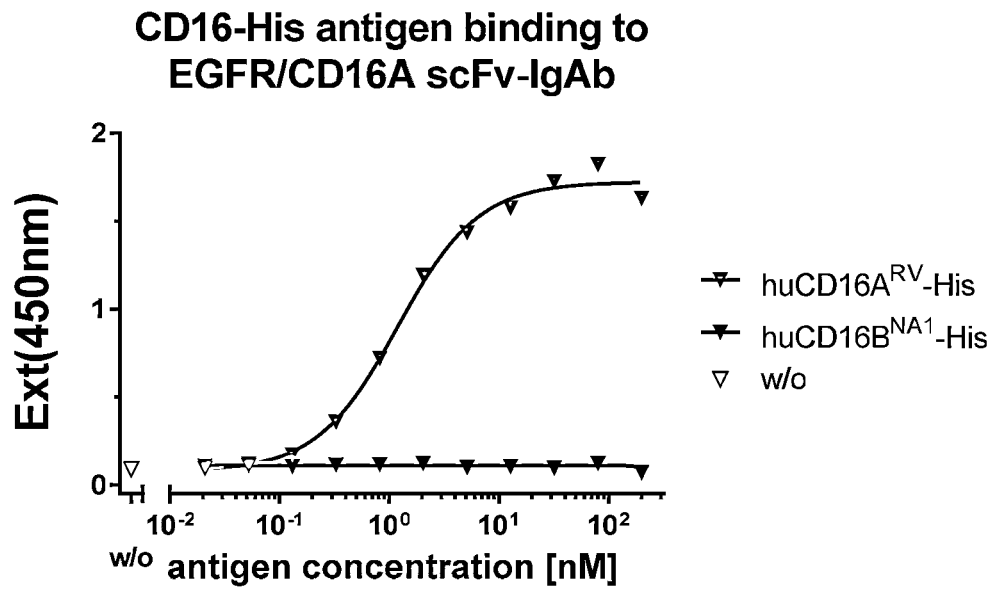
Figure 8:
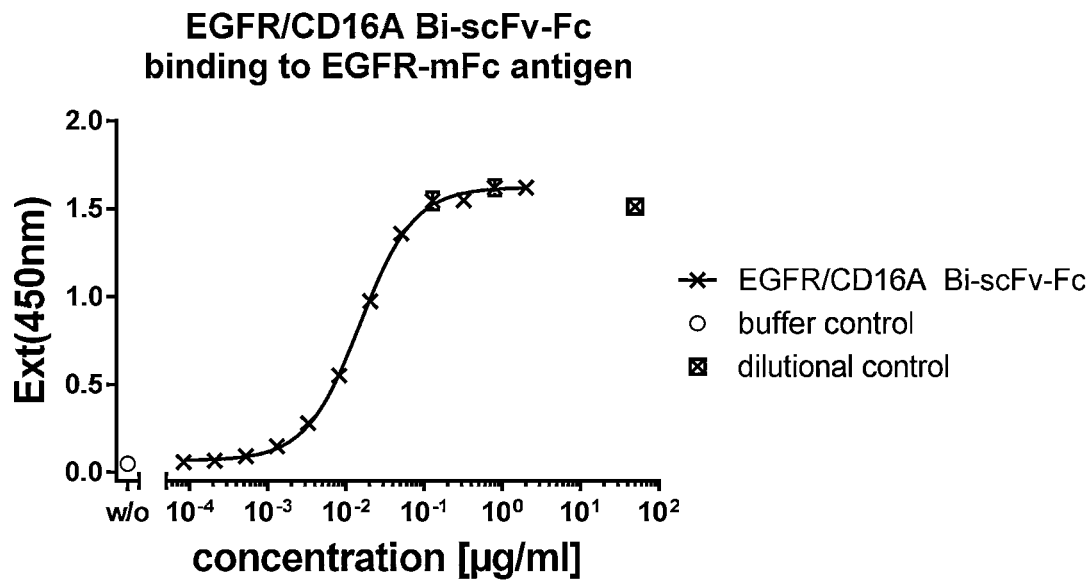
FIG. 8 shows concentration dependent binding of (A) EGFR/CD16A Bi-scFv-Fc to monomeric EGFR-mFc, or (B) CD16A- or CD16B-antigen to EGFR/CD16A Bi-scFv-Fc
Figure 8:
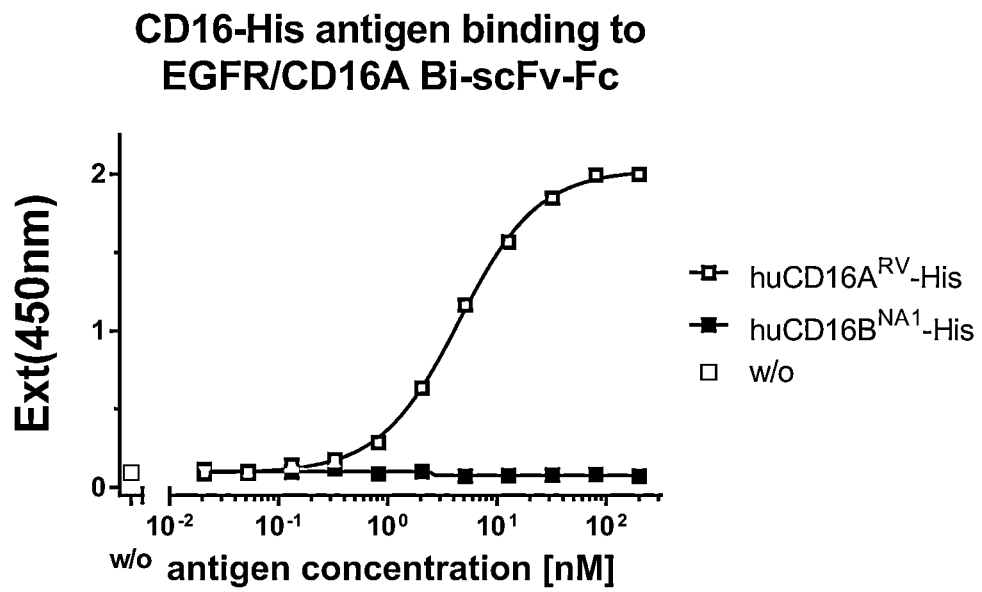
Figure 9:
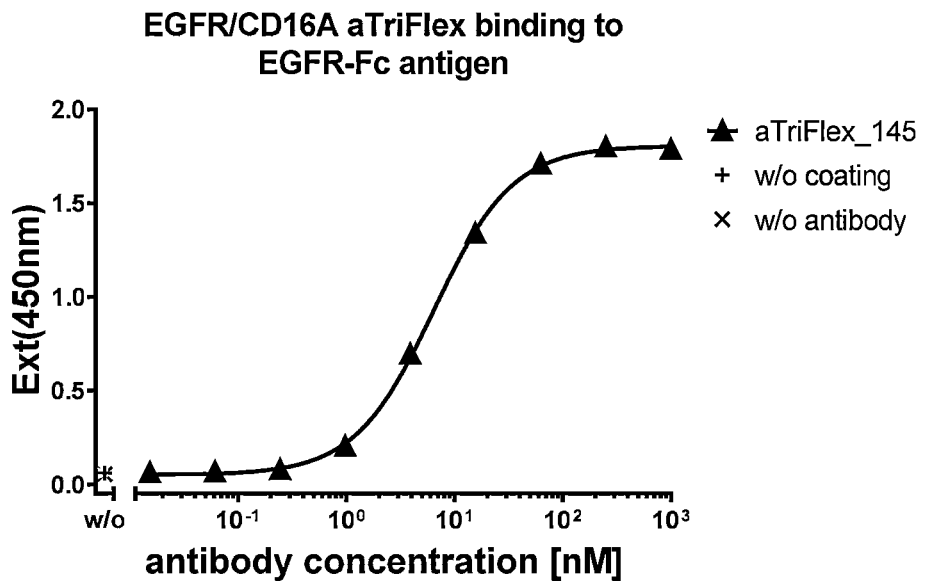
FIG. 9 shows concentration dependent binding of EGFR/CD16A aTriFlex to (A) EGFR- or (B) CD16A-antigen.
Figure 9:
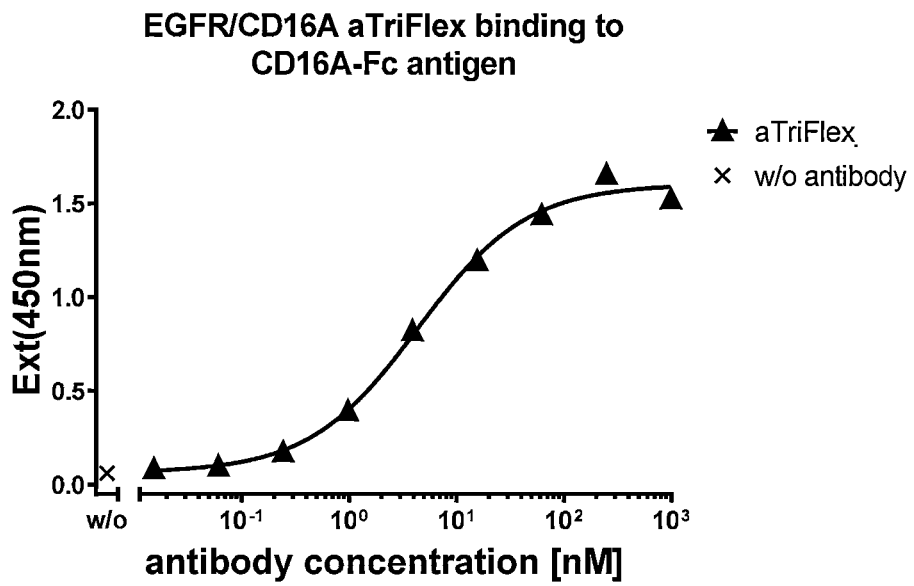

Anti-EGFR antigen-binding proteins were purified from clarified CHO cell culture supernatants in a two-step procedure comprising Protein A and preparative SEC. For Protein A, the clarified supernatant was loaded on a HiTrap MabSelectSuRe column. After washing with phosphate-buffered saline pH 7.4 and 10 mM sodium phosphate pH 7.0 protein was eluted in a two-step gradient with 50 mM sodium acetate pH 3.5 and 10 mM glycine/HCL pH 2.0. The purity of fractions was analyzed using SE-HPLC and SDS-PAGE. Fractions exhibiting acceptable purity were pooled and subjected to preparative gel filtration using a Superdex 200 prep grade column. Eluate fractions containing purified anti-EGFR antigen-binding proteins were pooled and subjected to buffer exchange using Sephadex G-25 column against 10 mM sodium acetate, 4.5% sorbitol pH 5.0, and concentrated by ultrafiltration to a typical concentration of approx. 1 mg/mL. Homogeneity of the final samples (scFv-IgAb_2 approx. 79% and Bi-scFv-Fc 2 approx. 85%) were assessed by SDS-PAGE under reducing and non-reducing conditions (see FIG. 5). The samples were mixed with nonreducing 2×SDS-PAGE sample buffer or reducing 2× SDS-PAGE sample buffer containing dithiothreitol (DTT) as reducing agent. All samples were heated at 95° C. for 5 min prior to loading on 4-20% Criterion TGX Precast SDS Page Gel. 2 μg of purified protein sample per lane were used. To separate the proteins in the gel, SDS-PAGE were run in 1× Tris/Glycine/SDS buffer at 300 V for approx. 22 min. Total protein were visualized in the gel using the Criterion Stain-free Molecular Imaging System (BioradBio-Rad). Page Ruler Unstained Protein ladder was used as molecular weight marker. The purity (scFv-IgAb_2 approx. 99% and Bi-scFv-Fc 2 approx. 97%) were evaluated by analytical SE-HPLC using Superdex200 Increase 10/300GL column. Purified proteins were stored as aliquots at −80° C. until further use.

Analysis of Binding of EGFR/CD16A Antigen-Binding Proteins in ELISA

Analysis of Binding in ELISA 96-well ELISA plates (Immuno MaxiSorp; Nunc) were coated overnight at 4° C. with recombinant antigen or antibodies in 100 mM Carbonate-bicarbonate buffer. EGFR-mFc antigen was coated at a concentration of 2.5 μg/mL, EGFR-Fc at 3 μg/mL, CD16A-Fc at 1.5 μg/ml, EGFR/CD16A scFv-IgAb at 3.8 μg/ml, or EGFR/CD16A Bi-scFv-Fc at 3 μg/mL. After a blocking step with 3% (w/v) skim milk powder (Merck) dissolved in PBS, serial dilutions of the different antibodies or soluble antigens in PBS containing 0.3% (w/v) skim milk powder were incubated on the plates for 1.5 h at room temperature. After washing three times with 300 μL per well of PBS containing 0.1% (v/v) Tween 20, plates were incubated with detection antibodies for 1 h at room temperature. For the detection of His-tagged analytes, Penta-HIS-HRP (Qiagen) was used at 1:3000 dilution. For the detection of EGFR/CD16A scFv-IgAb or EGFR/CD16A Bi-scFv-Fc bound on EGFR-mFc antigen, biotinylated CD16-Fc was incubated on the plates at 1 μg/mL for 1 hour at room temperature followed by washing and incubation with Streptavidin-HRP conjugate (Roche) at 1:10000 dilution for 1 hour at room temperature. After washing three times with 300 μL per well of PBS containing 0.1% (v/v) Tween 20, plates were incubated with Tetramethylbenzidine (TMB) substrate (Seramun) until colour development was clearly visible. The reaction was stopped through the addition of 100 μL per well of 0.5 M $H_2SO_4$. The absorbance was measured at 450 nm using a multilabel plate reader (Victor, Perkin Elmer). Absorbance values were plotted and analyzed using nonlinear regression, sigmoidal dose-response (variable slope), least squares (ordinary) fit with GraphPad Prism version 6.07 (GraphPad Software, La Jolla California USA).

Binding to FcRn and Various Fcγ-Receptors

For characterization of silenced Fc in EGFR/CD16A antigen-binding proteins, binding to various Fcγ-receptors and FcRn (pH 6.0) was measured using Surface Plasmon Resonance Spectroscopy (SPR).

Material & Methods:

Ligand Molecules

Various Fcγ-receptors (human, canis, cynomolgus, murine) fused to mono Fc (mFc) and Avi-Tag were expressed in CHO and purified via Protein A and Size Exclusion Chromatography (SEC). Molecules were biotinylated at Avi-Tag using Biotin-Protein Ligase/BirA Kit (GeneCopoeia).

| | | |
|---|---|---|
| CD64 | human | FcγRI-mFc-Avi |
| CD32A | human | FcγRIIa-mFc-Avi |
| CD32B | human | FcγRIIb-mFc-Avi |
| CD32C | human | FcγRIIc-mFc-Avi |
| CD16A | human | FcγRIIIa (48R-158V)-mFc-Avi |
| CD16B | human | FcγRIIIb (NA1)-mFc-Avi |
| CD64 | murine | FcγRI-mFc-Avi |
| CD32 | murine | FcγRIIb-mFc-Avi |
| CD16 | murine | FcγRIII-mFc-Avi |
| CD16-2 | murine | FcγRIV-mFc-Avi |
| CD16 | canis | FcγRIII-mFc-Avi |
| CD32A | cynomolgus | FcγRIIa-mFc-Avi |
| CD32B/C | cynomolgus | FcγRIIb/c-mFc-Avi |
| CD16 | cynomolgus | FcγRIII-mFc-Avi |

Biotinylated FcRn molecules (human, mouse, cynomolgus) were purchased:
  FcRn (FCGRT/B2M), His-Tag, Biotin-Labeled, (Human) HiP™ Cat #71283
  FcRn (FCGRT/B2M), His-Avi-Tag, Biotin-Labeled, (mouse) HiP™ Cat #71286
  FcRn (FCGRT/B2M), Avi-Tag, Biotin-Labeled, (Cynomolgus) Acrom™ Cat #FCM-C82W5

SPR Methods

A) Binding to Various Fcγ-Receptors

Binding of EGFR/CD16A antigen-binding protein to various Fcγ-receptors was measured on a Biacore T200 Instrument at 25° C. using HBS-P+.

b) Binding to FcRn

Binding of EGFR/CD16A antigen-binding proteins to FcRn (human, cynomolgus, murine) was measured on a Biacore T200 Instrument at 25° C. using PBS-T buffer pH 6.0 as running buffer and for dilution (1× Gibco PBS, 0.005% Tween20, titrated to pH 6.0 using 4 M HCl). For this purpose, a Multi Cycle Kinetic experiments was performed using Biotin CAPture Kit (GE Healthcare). For activation of the sensor surface, Biotin CAPture reagent (GE Healthcare) was injected to Flow Cells Fc 1-4 (100 sec, 5 µL/min) resulting in a response of 2100 RU-2800 RU. Biotinylated FcRn of different species were injected to Flow Cell Fc 2 (5 µL/min) resulting in a response of about 8-15 RU. A dilution series of EGFR/CD16A antigen-binding proteins was in(pH 7.4) as running buffer and for dilution. For this purpose, a Single Cycle Kinetic Experiment was performed using Biotin CAPture Kit (GE Healthcare). For activation of the sensor surface, Biotin CAPture reagent (GE Healthcare) was injected to Flow Cells Fc 1-4 (100 sec, 5 µL/min) resulting in a response of 2100 RU-2800 RU. Biotinylated Fcγ-Receptors were captured (35 RU-55 RU) in Flow Cells Fc 2, Fc 3, Fc 4). A dilution series of anti-EGFR antibody constructs was injected to Flow cells Fc 1-4 in Single Cycle Kinetic mode (30 µL/min, association 180 sec, dissociation 240 sec, 6000 nM-1.47 nM dilution 1:4). Chip was regenerated using Regeneration solution (GE Healthcare) (10 µL/min, Flow cells 1-4, 120 sec). Sensorgrams are referenced by subtraction of zero concentration cycle and subtraction of signals in reference channel Fc 1 (Fc 2-1, Fc 3-1, Fc 4-1). Binding kinetics were evaluated by fitting data to 1:1 Binding Model (RI constant to zero) using Biacore T200 Evaluation Software jected to Flow cells Fc 1, 2 (30 µL/min, association 240 sec, dissociation 100 sec, 3000 nM-12.5 nM dilution 1:3). Chip was regenerated using Regeneration solution (GE Healthcare) (10 µL/min, Flow cells 1-4, 120 sec). Sensorgrams are referenced by subtraction of zero concentration cycle and subtraction of signals in reference channel Fc 1 (Fc 2-1). Binding kinetics were evaluated by fitting data to 1:1 Binding Model (Rmax and RI locally fitted) using Biacore T200 Evaluation Software.

Results

In Fcγ-receptor binding assays, scFv-IgAb_02 showed binding to human CD16A FcγRIIIa (48R-158V)-mFc-Avi ($K_D$ 12.5 nM) and cynomolgus CD16 FcγRIII-mFc-Avi ($K_D$ 19.9 nM), whereas no binding interaction was detected for all other tested Fcγ-Receptors (Table 1). Bi-scFv-Fc 02 showed binding to CD16A FcγRIIIa (48R-158V)-mFc-Avi ($K_D$ 12.2 nM) and cynomolgus CD16 FcγRIII-mFc-Avi ($K_D$ 25.2 nM) only. Control molecule EGFR/CD16A tandem diabody showed binding to human CD16A FcγRIIIa (48R-158V)-mFc-Avi ($K_D$ 4.4 nM) and cynomolgus CD16 FcγRIII-mFc-Avi ($K_D$ 8.9 nM). Functionality of all tested Fcγ-Receptors was shown by different IgG1 control molecules (Data not shown).

Silencing of Fc in scFv-IgAb_02 and Bi-scFv-Fc 02 can be verified by absence of binding interaction to tested Fcγ-receptors (except from specific binding to human CD16A and cynomolgus CD16 via anti-CD16A domain).

FcRn binding of scFv-IgAb_02 and Bi-scFv-Fc-02 at pH 6.0 was shown for human FcRn (scFv-IgAb_2 $K_D$ 430 nM, Bi-scFv-Fc 02 $K_D$ 410 nM), murine FcRn (scFv-IgAb_02 $K_D$ 180 nM, Bi-scFv-Fc 02 $K_D$ 121 nM) and cynomolgus FcRn (scFv-IgAb_02 $K_D$ 842 nM, Bi-scFv-Fc 02 $K_D$ 268 nM). No binding interaction was measured for control molecule EGFR/CD16A tandem diabody. Preservation of FcRn binding ability in silenced Fc of scFv-IgAb_02 and Bi-scFv-Fc 02 can be verified.

TABLE 1

Tabulated summary of Fcγ-Receptor binding assays with EGFR/CD16A antigen-binding proteins.

| Fcγ-Receptor | scFv-IgAb_02 | Bi-scFv-Fc-_02 | Tandem diabody |
|---|---|---|---|
| CD64 Human FcγRI-mFc-Avi | No binding | No binding | No binding |
| CD32A Human FcγRIIa-mFc-Avi | No binding | No binding | No binding |
| CD32B Human FcγRIIb-mFc-Avi | No binding | No binding | No binding |
| CD32C Human FcγRIIc-mFc-Avi | No binding | No binding | No binding |
| CD16A Human FcγRIIIa (48R-158V)-mFc-Avi | $K_D$ 12.5 nM | $K_D$ 12.2 nM | $K_D$ 4.4 nM |
| CD16B human FcγRIIIb (NA1)-mFc-Avi | No binding | No binding | No binding |
| CD64 murine FcγRI-mFc-Avi | No binding | No binding | No binding |
| CD32 murine FcγRIIb-mFc-Avi | No binding | No binding | No binding |
| CD16 murine FcγRIII-mFc-Avi | No binding | No binding | No binding |
| CD16-2 murine FcγRIV-mFc-Avi | No binding | No binding | No binding |
| CD16 canis FcγRIII-mFc-Avi | No binding | No binding | No binding |
| CD32A cynomolgus FcγRIIa-mFc-Avi | No binding | No binding | No binding |
| CD32B/C cynomolgus FcγRIIb/c-mFc-Avi | No binding | No binding | No binding |
| CD16 cynomolgus FcγRIII-mFc-Avi | $K_D$ 19.9 nM | $K_D$ 25.2 nM | $K_D$ 8.9 nM |

TABLE 2

Tabulated summary of FcRn binding at pH 6.0 with EGFR/CD16A antigen-binding proteins.

| FcRn | scFv-IgAb_02 | Bi-scFv-Fc_02 | Tandem diabody |
|---|---|---|---|
| Human FcRn (FCGRT/B2M) | Binding $K_D$ 430 nM | Binding $K_D$ 410 nM | No binding |
| Cynomolgus FcRn (FCGRT/B2M) | Binding | Binding | No binding |
| Mouse FcRn (FCGRT/B2M) | Binding $K_D$ 180 nM | Binding $K_D$ 121 nM | No binding |

Example 2

Binding of Bispecific EGFR/CD16A Antigen-Binding Protein to Primary Human NK-Cells in the Presence or Absence of 10 mg/mL Polyclonal Human IgG Methods:

Isolation of PBMC from Buffy Coats and Enrichment of Human NK-Cells

PBMCs were isolated from buffy coats (German Red Cross, Mannheim, Germany) by density gradient centrifugation. The buffy coat samples were diluted with a two-to-threefold volume of PBS (Invitrogen, cat.: 14190-169), layered on a cushion of Lymphoprep (Stem Cell Technologies, cat.: 07861) and centrifuged at 800×g for 25 min at room temperature w/o brake. PBMC located in the interface were collected and washed 3 times with PBS before they were cultured in complete RPMI 1640 medium supplemented with 10% FCS overnight without stimulation. For the enrichment of NK-cells, PBMCs were harvested from overnight cultures and used for one round of negative selection using the EasySep™ Human NK-Cell Enrichment Kit (Stem Cell Technologies, cat.: 19955) for the immunomagnetic isolation of untouched human NK-cells and the Big Easy EasySep™ Magnet (Stem Cell Technologies, cat.: 18001) according to the manufacturer's instructions.

Cell Binding Assays and Flow Cytometric Analyses

Aliquots of the indicated cell types were incubated with 100 µL of serial dilutions of various bispecific EGFR/CD16A antigen-binding proteins with or without 10 mg/mL polyclonal human IgG (Gammanorm, Octapharma) in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) for 45 min at 37° C. After repeated washing with FACS buffer, cell-bound antibodies were detected with 10 mg/mL anti-EGFR mAb (clone 62-1-1 Biogenes) followed by 15 µg/mL FITC-conjugated goat anti-mouse IgG (Dianova, cat.: 115-095-062). Biotinylated cetuximab as well as biotinylated anti-EGFR IgG antibodies (IgAb_wtFc, IgAb_enhFc) were detected by AlexaFluor 488-conjugated Streptavidin (Dianova 016-540-084). After the last staining step, the cells were washed again and resuspended in 0.2 mL of FACS buffer containing 2 µg/mL propidium iodide (PI) (Sigma, cat.: P4170) in order to exclude dead cells. The fluorescence of $2-5 \times 10^3$ living cells was measured using a Millipore Guava EasyCyte flow cytometer (Merck Millipore, Schwalbach, Germany). Mean fluorescence intensities of the cell samples were calculated using Incyte software (Merck Millipore, Schwalbach, Germany). After subtracting the fluorescence intensity values of the cells stained with the secondary and tertiary reagents alone, the values were used for non-linear regression analysis using the GraphPad Prism software (GraphPad Prism version 6.00 for Windows, GraphPad Software, La Jolla California USA). For the calculation of $K_D$, the equation for one-site-binding (hyperbola) was used.

Results

Figure 10:
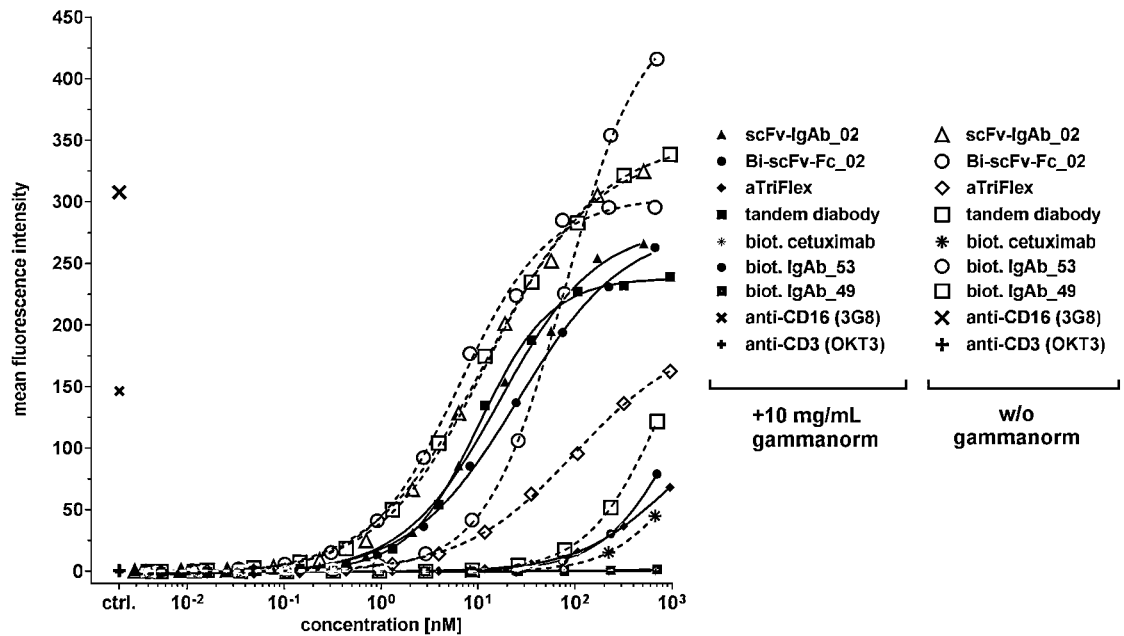
FIG. 10 shows the assessment of the binding affinities of several bispecific EGFR/CD16A antigen-binding proteins in presence and absence of 10 mg/mL human polyclonal IgG (Gammanorm) on primary human NK-cells. Mean fluorescence intensity at increasing concentrations.
Figure 11:
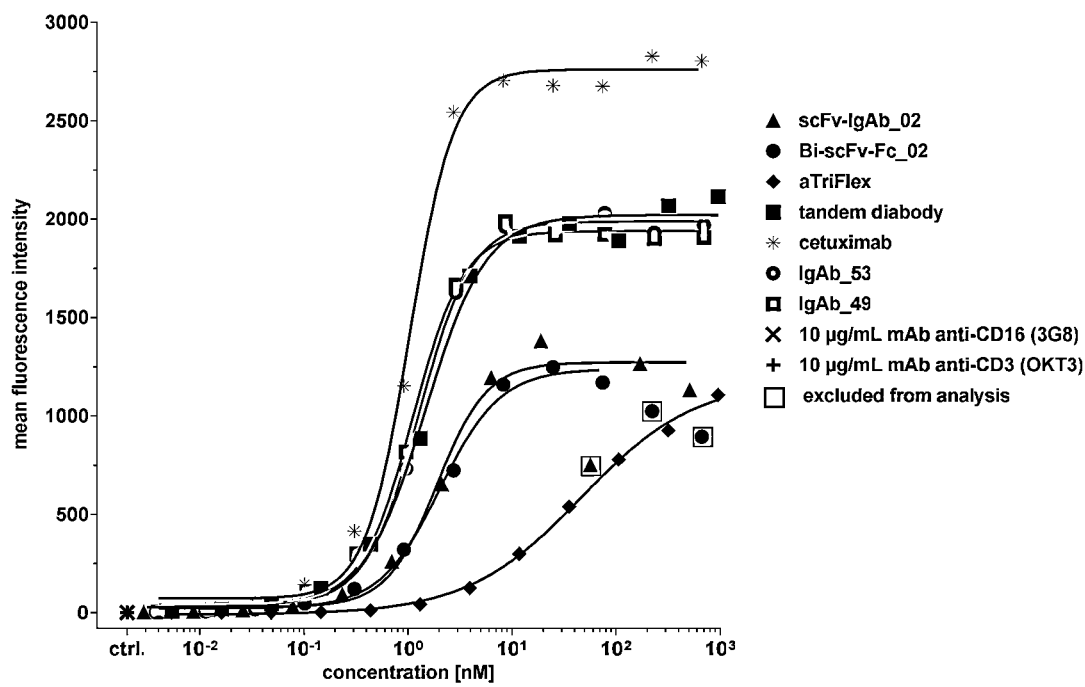
FIG. 11 shows the assessment of the binding affinities of several bispecific EGFR/CD16A antigen-binding proteins on EGFR-expressing tumor A-431 cells.

To assess the impact of physiological concentrations of human IgG on the binding capacity of bispecific EGFR/CD16A antigen-binding proteins, binding assays with several bispecific EGFR/CD16A antigen-binding proteins on primary human NK-cells were performed in presence or absence of 10 mg/mL polyclonal human IgG as exemplarily shown in FIG. 10. Table 3 summarizes the binding affinities of the indicated bispecific antigen-binding proteins under both conditions. The apparent affinity of EGFR/CD16A tandem diabody on primary human NK-cells is not substantially changed in the presence of 10 mg/mL polyclonal human IgG. However, the addition of IgG lowers the affinity of Bi-scFv-Fc 02 by roughly factor 4 from 5 nM to 20 nM.

TABLE 3

Apparent affinities of bispecific EGFR/CD16A antigen-binding proteins on primary human NK-cells in presence or absence of 10 mg/mL polyclonal human IgG determined in two independent binding assays.

| construct | description | without IgG $K_D$ [nM] mean | SD | n | with 10 mg/mL Gammanorm $K_D$ [nM] mean | SD | n | fold loss on KD induced by IgG mean | SD |
|---|---|---|---|---|---|---|---|---|---|
| scFv-IgAb_02 | EGFR/CD16A antibody construct with anti-EGFR scFv domain and anti-CD16A Fab domain | 8.0 | 3.12 | 2 | 13.1 | 3.01 | 2 | 1.7 | 0.29 |
| Bi-scFv-Fc_02 | EGFR/CD16A antibody construct with anti-EGFR scFv domain and anti-CD16A scFv domain | 5.0 | 1.74 | 2 | 20.0 | 0.59 | 2 | 4.2 | 1.35 |
| aTriFlex_ | aTriFlex construct with anti-CD16A diabody and with anti-EGFR scFv domain and anti-HSA scFv domain | 50.8 | 21.26 | 2 | 456 | n.a. | 2 | n.a. | n.a. |
| Tandem diabody | EGFR/CD16A tandem diabody with anti-EGFR Fv domain and anti-CD16A Fv domain | 7.7 | 3.34 | 2 | 8.8 | 3.12 | 2 | 1.2 | 0.10 |
| cetuximab | Chimeric IgG1 with wt Fc and anti-EGFR Fab domain derived from clone C225 | no | n.a. | 2 | no | n.a. | 2 | n.a. | n.a. |
| IgAb_enhFc | Human IgG1 with enhanced Fc and anti-EGFR Fab domain | 74.3 | 14.88 | 2 | 3886 | n.a. | 2 | n.a. | n.a. |
| IgAb_wtFc | Human IgG1 with wt Fc and anti-EGFR Fab domain | 1366 | n.a. | 2 | no | n.a. | 2 | n.a. | n.a. |

Mean $K_D$ and SD values of independent experiments are presented.
SD, standard deviation;
n, number of independent experiments;
no, no binding;
n.a., not applicable.

Example 3

Binding of EGFR/CD16A Tandem Diabody on CHO Cells Expressing Recombinant Human EGFR or EGFRvIII Cell Binding Assays and Flow Cytometric Analysis Aliquots of the indicated cells were incubated with 100 µL of serial dilutions of His-tagged tandem diabodies in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) for 45 min at 37° C. After repeated washing with FACS buffer, cell-bound antibodies were detected with 10 µg/mL anti-His mAb 13/45/31-2 (Dianova, Hamburg, Germany, cat.: DIA910-1MG) followed by 15 μg/mL FITC-conjugated goat anti-mouse IgG (Dianova, cat.: 115-095-062). After last staining step, the cells were washed again and resuspended in 0.2 mL of FACS buffer containing 2 μg/mL propidium iodide (PI) (Sigma, cat.: P4170) in order to exclude dead cells. The fluorescence of $2-5 \times 10^3$ living cells was measured using a Beckman-Coulter FC500 MPL flow cytometer using the MXP software (Beckman-Coulter, Krefeld, Germany) or a Millipore Guava EasyCyte flow cytometer (Merck Millipore, Schwalbach, Germany). Mean fluorescence intensities of the cell samples were calculated using CXP software (Beckman-Coulter) or Incyte software (Merck Millipore, Schwalbach, Germany). After subtracting the fluorescence intensity values of the cells stained with the secondary and tertiary reagents alone, the values were used for non-linear regression analysis using the GraphPad Prism software (GraphPad Prism version 6.00 for Windows, GraphPad Software, La Jolla California USA). For the calculation of $K_D$, the equation for one-site-binding (hyperbola) was used.

Results

EGFR/CD16A tandem diabody possesses similar apparent affinity to cells expressing human EGFR or EGFRvIII at 37° C. (Table 4).

Thus, the EGFR/CD16A antigen-binding protein can be used for the treatment of both, EGFR-expressing and EGFRvIII-expressing cancers. EGFRvIII in contrast to EGFR is expressed exclusively on cancer cells but not on healthy tissue.

TABLE 4

Apparent affinity of EGFR/CD16A tandem diabody on CHO cells expressing recombinant human EGFR or EGFRvIII at 37° C.

| construct | apparent affinity KD [nM] | |
|---|---|---|
| | EGFR+ CHO cells | EGFRvIII+ CHO cells |
| tandem diabody | 0.7 | 0.5 |

Example 4

Binding of EGFR/CD16A Constructs to EGFR+ A-431 and HCT-116 Cells
Methods:
Culture of Cell Lines A-431 (ATCC, cat.: CRL-1555, RAS wt) were cultured under standard conditions in DMEM medium supplemented with 10% heat-inactivated FCS, 2 mM L-glutamine and 100 IU/mL penicillin G sodium and 100 μg/mL streptomycin sulfate (all components from Invitrogen). HCT-116 (ATCC, cat.: CCL-247, RAS mut) were cultured under standard conditions in RPMI 1640 medium supplemented with 10% heat-inactivated FCS, 2 mM L-glutamine and 100 IU/mL penicillin G sodium and 100 μg/mL streptomycin sulfate (all components from Invitrogen, herein referred to as complete RPMI 1640 medium). All cell lines were cultured at 37° C. in a humidified atmosphere with 5% $CO_2$.
Cell Binding Assays and Flow Cytometric Analyses Aliquots of the indicated cell types were incubated with 100 μL of serial dilutions of the indicated bispecific EGFR/CD16A antigen-binding protein in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) for 45 min at 37° C. After repeated washing with FACS buffer, cell-bound antibodies were detected with 10 μg/mL of an anti-EGFR mAb (clone 4-1-1 (Biogenes)) followed by FITC conjugated goat anti-mouse IgG min X (Dianova; cat. 115-095-062). Cell surface bound cetuximab, anti-EGFR with wtFc (IgAb_wtFc; IgAb_49) anti-EGFR with enhanced Fc (IgAb_enhFc, IgAb_53) were detected by FITC conjugated goat anti-human IgG (Dianova; cat. 109-095-08). After the last staining step, the cells were washed again and resuspended in 0.2 mL of FACS buffer containing 2 μg/mL propidium iodide (PI) (Sigma, cat.: P4170) in order to exclude dead cells. The fluorescence of $2-5 \times 10^3$ living cells was measured using a Millipore Guava EasyCyte flow cytometer (Merck Millipore, Schwalbach, Germany). Mean fluorescence intensities of the cell samples were calculated using the Incyte software (Merck Millipore, Schwalbach, Germany). After subtracting the fluorescence intensity values of the cells stained with the secondary and tertiary reagents alone, the values were used for non-linear regression analysis using the GraphPad Prism software (GraphPad Prism version 6.00 for Windows, GraphPad Software, La Jolla California USA). For the calculation of $K_D$, the equation for one-site-binding (hyperbola) was used.

Results

Apparent affinities of bispecific EGFR/CD16A antigen-binding proteins on EGFR+ tumor cell lines were determined in independent binding experiments and summarized in Table 5.

TABLE 5

Apparent affinities of EGFR/CD16A antigen-binding proteins determined in independent binding assays on EGFR+ tumor cell lines.

| | Cell line | | | | | |
|---|---|---|---|---|---|---|
| | A-431 | | | HCT-116 | | |
| $K_D$ [nM] | mean | SD | n | mean | SD | n |
| scFv-IgAb_02 | 1.8 | 0.02 | 2 | 50.4 | n.a. | 2 |
| Bi-scFv-Fc_02 | 1.8 | 0.55 | 2 | 37.9 | 15.68 | 2 |
| aTriFlex | 39.7 | 4.79 | 2 | n.a. | n.a. | 2 |
| Tandem diabody | 1.1 | 0.52 | 2 | 0.3 | 0.16 | 2 |
| cetuximab | 0.9 | 0.17 | 2 | 0.1 | 0.04 | 2 |
| IgAb_enhFc | 1.1 | 0.21 | 2 | 0.8 | 0.03 | 2 |
| IgAb_wtFc | 1.0 | 0.20 | 2 | 0.7 | 0.01 | 2 |

Mean $K_D$ and SD values of independent experiments are presented.
SD, standard deviation;
n, number of independent experiments;
n.a., not applicable.

Example 5

Cytotoxic Activity of Bispecific EGFR/CD16A Antigen-Binding Proteins on EGFR+ Tumor Cell Lines
Methods:
Culture of Cell Lines A-431 (ATCC, cat.: CRL-1555) were cultured under standard conditions in DMEM medium supplemented with 10% heat-inactivated FCS, 2 mM L-glutamine and 100 IU/mL penicillin G sodium and 100 μg/mL streptomycin sulfate (all components from Invitrogen). HCT-116 (ATCC, cat.: CCL-247) were cultured under standard conditions in RPMI 1640 medium supplemented with 10% heat-inactivated FCS, 2 mM L-glutamine and 100 IU/mL penicillin G sodium and 100 μg/mL streptomycin sulfate (all components from Invitrogen, herein referred to as complete RPMI 1640 medium). All cell lines were cultured at 37° C. in a humidified atmosphere with 5% $CO_2$.

Isolation of PBMC from Buffy Coats and Enrichment of Human NK-Cells

PBMCs were isolated from buffy coats (German Red Cross, Mannheim, Germany) by density gradient centrifugation. The buffy coat samples were diluted with a two-to-threefold volume of PBS (Invitrogen, cat.: 14190-169), layered on a cushion of Lymphoprep (Stem Cell Technologies, cat.: 07861) and centrifuged at 800×g for 25 min at room temperature w/o brake. PBMC located in the interface were collected and washed 3 times with PBS before they were cultured in complete RPMI 1640 medium supplemented with 10% human pool serum (Sigma, cat.: H4522) instead 10% FCS overnight without stimulation. For the enrichment of NK-cells PBMC were harvested from overnight cultures and used for one round of negative selection using the EasySep™ Human NK-Cell Enrichment Kit (Stem Cell Technologies, cat.: 19055) for the immunomagnetic isolation of untouched human NK-cells and the Big Easy EasySep™ Magnet (Stem Cell Technologies, cat.: 18001) according to the manufacturer's instructions.

4 h Calcein-Release Cytotoxicity Assays

For calcein-release cytotoxicity assays the indicated target cells were harvested from cultures, washed with RPMI 1640 medium without FCS, and labeled with 10 µM calcein AM (Invitrogen/Molecular Probes, cat.: C3100MP) for 30 min in RPMI medium without FCS at 37° C. After gently washing the labeled cells were resuspended in complete RPMI medium (RPMI 1640 medium supplemented with 10% heat-inactivated FCS, 4 mM L-glutamine, 100 U/mL penicillin G sodium, 100 µg/mL streptomycin sulfate) to a density of $1 \times 10^5$/mL. $1 \times 10^4$ target cells were then seeded together with enriched primary human NK-cells at an E:T ratio of 5:1 and the indicated antibodies at 12 serial dilutions in individual wells of a round-bottom 96-well micro plate in a total volume of 200 µL/well in duplicates. Spontaneous release, maximal release and killing of targets by effectors in the absence of antibodies were determined in quadruplicate on each plate.

After centrifugation for 2 min at 200 g the assay was incubated for 4 h at 37° C. in a humidified atmosphere with 5% $CO_2$. 15 min prior to the end of incubation 20 µL of 10% Triton X-100 in RPMI medium were added to wells containing target cells. 20 µL RPMI medium was added to all other wells. 100 µL cell culture supernatant were harvested from each well after an additional centrifugation for 5 min at 500 g, and the fluorescence of the released calcein was measured at 520 nm using a fluorescence plate reader (EnSight Multimode Plate Reader, Perkin Elmer). On the basis of the measured counts, the specific cell lysis was calculated according to the following formula: [fluorescence (sample)−fluorescence (spontaneous)]/[fluorescence (maximum)−fluorescence (spontaneous)]×100%. Fluorescence (spontaneous) represents the fluorescent counts from target cells in the absence of effector cells and antibodies and fluorescence (maximum) represents the total cell lysis induced by the addition of Triton X-100. Sigmoidal dose response curves and $EC_{50}$ values were calculated by non-linear regression/4-parameter logistic fit using the GraphPad Prism software (GraphPad Prism version 6.00 for Windows, GraphPad Software, La Jolla California USA).

Results

Figure 12:
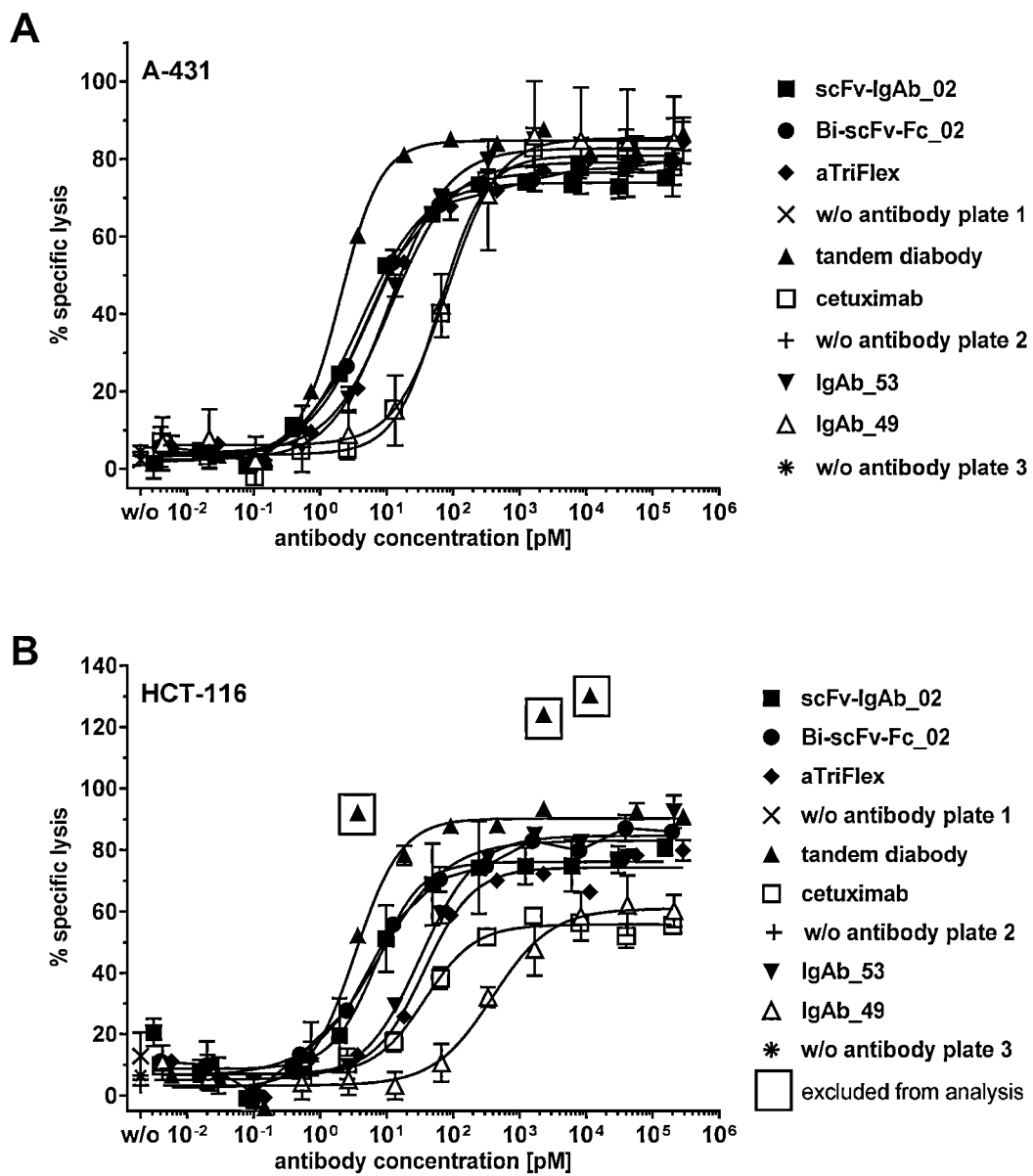
FIG. 12 shows cytotoxic activity of bispecific EGFR/CD16A antigen-binding proteins in 4 h calcein-release assays on A-431 (A) and HCT-116 (B) target cells with enriched human NK-cells as effector cells at an E:T ratio of 5:1.

Various bispecific EGFR/CD16A antigen-binding proteins were tested together with control constructs in 4 h calcein-release cytotoxicity assays on $EGFR^+$ A-431 and HCT-116 target cells. The antigen-binding proteins did not show off-target cytotoxicity. FIG. 12 shows the results of one exemplary experiment. The results from 3 independent experiments are summarized in Table 6 (A-431 target cells) and Table 7 (HCT-116 target cells).

TABLE 6

Cytotoxicity of bispecific EGFR/CD16A antigen-binding proteins on A-431 target cells Mean and SD of $EC_{50}$ values [pM] for EGFR/CD16A antigen-binding proteins determined in three independent 4 h calcein-release cytotoxicity assays on $EGFR^+$ A-431 tumor target cells with enriched human NK-cells as effector cells at an E:T ratio of 5:1. SD, standard deviation; no, no lysis; n.a., not applicable.

| construct | description | $EC_{50}$ [pM] mean | SD |
|---|---|---|---|
| scFv-IgAb_02 | antigen-binding protein with anti-EGFR scFv domain and anti-CD16A Fab domain (FIG. 1) | 2.1 | 1.87 |
| Bi-scFv-Fc_02 | Antigen-binding protein with anti-EGFR scFv domain and anti-CD16A scFv domain (FIG. 2) | 2.7 | 2.76 |
| aTriFlex | aTriFlex construct with anti-CD16A diabody and with anti-EGFR scFv domain and anti-HSA scFv domain (FIG. 4) | 5.1 | 5.69 |
| Tandem diabody | EGFR/CD16A tandem diabody with anti-EGFR Fv domain and anti-CD16A Fv domain (FIG. 3) | 1.1 | 0.91 |
| cetuximab | Chimeric IgG1 with wt Fc and anti-EGFR Fab domain derived from clone C225 | 24.5 | 33.90 |
| IgAb_enhFc | Human IgG1 with enhanced Fc and anti-EGFR Fab domain | 4.8 | 5.59 |
| IgAb_wtFc | Human IgG1 with wt Fc and anti-EGFR Fab domain | 32.6 | 41.98 |

TABLE 7

Cytotoxicity of bispecific EGFR/CD16A antigen-binding proteins on HCT-116 target cells
Mean and SD of $EC_{50}$ values [pM] for EGFR/CD16A antigen-binding proteins determined in
three independent 4 h calcein-release cytotoxicity assays on $EGFR^+$ HCT-116
tumor target cells with enriched human NK-cells as effector cells at an E:T ratio
of 5:1. SD, standard deviation; no, no lysis; n.a., not applicable

| construct | description | $EC_{50}$ [pM] mean | SD |
|---|---|---|---|
| scFv-IgAb_02 | EGFR/CD16A antibody construct with anti-EGFR scFv domain and anti-CD16A Fab domain (FIG. 1) | 4.3 | 2.42 |
| Bi-scFv-Fc_02 | EGFR/CD16A antibody construct with anti-EGFR scFv domain and anti-CD16A scFv domain (FIG. 2) | 3.8 | 3.27 |
| aTriFlex | aTriFlex construct with anti-CD16A diabody and with anti-EGFR scFv domain and anti-HSA scFv domain (FIG. 4) | 17.6 | 17.33 |
| Tandem diabody | EGFR/CD16A tandem diabody with anti-EGFR Fv domain and anti-CD16A Fv domain (FIG. 3) | 1.5 | 1.69 |
| cetuximab | Chimeric IgG1 with wt Fc and anti-EGFR Fab domain derived from clone C225 | 18.6 | 17.59 |
| IgAb_enhFc | Human IgG1 with enhanced Fc and anti-EGFR Fab domain | 14.1 | 15.94 |
| IgAb_wtFc | Human IgG1 with wt Fc and anti-EGFR Fab domain | 149.1 | 211.25 |

Example 6

Inhibition of EGFR Phosphorylation

To compare the inhibitory effect of different EGFR/CD16A antigen-binding proteins on EGF-induced EGFR signaling, phosphorylation assays with A-431 cells were performed.

Material & Methods:
Culture of Cell Lines

A-431 (ATCC, cat.: CRL-1555) were cultured under standard conditions in DMEM medium supplemented with 10% heat-inactivated FCS, 2 mM L-glutamine and 100 IU/mL penicillin G sodium and 100 µg/mL streptomycin sulfate (all components from Invitrogen) at 37° C. in a humidified atmosphere with 5% $CO_2$.

Phosphorylation Assay

In brief, aliquots of $5\times10^4$ A-431 cells (ATCC, cat.: CRL-1555) were seeded in individual wells of a 96 well plate in DMEM medium supplemented with 10% heat-inactivated FCS, 2 mM L-glutamine and 100 IU/mL penicillin G sodium and 100 µg/mL streptomycin sulfate (all components from Invitrogen) for 20 h at 37° C. in a humidified atmosphere with 5% $CO_2$. Cells were then starved for 4 h in medium without serum before serial dilutions of the indicated antibody constructs were added. After 30 min incubation at 37° C., EGF (Sigma, cat.: 10605-HNAE-250) was added to a final concentration of 100 ng/mL and cultures were further incubated for 10 min at 37° C. before cells were washed with ice-cold PBS (Invitrogen, cat.: 14190-169) and lysed and used for relative quantification of phosphorylated EGFR using an Phospho-EGFR ELISA Kit (RayBiotech, cat.: PEL-EGFR-Y) according to the instructions of the manufacturer. The absorbance was measured at 450 nm with a multiplate reader (Victor 3, Perkin Elmer). Absorbance values were analyzed and plotted using GraphPad Prism software (GraphPad Prism version 6.00 for Windows, GraphPad Software, La Jolla California USA).

Cell Binding Assays and Flow Cytometric Analysis

Aliquots of the indicated cell were incubated with 100 µL of serial dilutions of the indicated antibodies in FACS buffer (PBS, Invitrogen, cat.: 14190-169) containing 2% heat-inactivated FCS (Invitrogen, cat.: 10270-106), 0.1% sodium azide (Roth, Karlsruhe, Germany, cat.: A1430.0100) for 45 min at 37° C. After repeated washing with FACS buffer, cell-bound tandem diabodies were detected with 10 µg/mL anti-His mAb 13/45/31-2 (Dianova, Hamburg, Germany, cat.: DIA910-1MG) followed by 15 µg/mL FITC-conjugated goat anti-mouse IgG (Dianova, cat.: 115-095-062) or with mAb 4-1-1, generated against the anti-CD16A Fv domain ((SEQ ID NOs:12,13) followed by 15 µg/mL FITC-conjugated goat anti-mouse IgG. Cell surface bound Bi-scFv-Fc_02 (SEQ ID NO:30), scFv-IgAb_01 and scFv-IgAb_02 (SEQ ID NOs:28,29) were detected by FITC-conjugated goat anti-human IgG (Dianova, cat.: 109-095-088) or with mAb 4-1-1 followed by 15 µg/mL FITC-conjugated goat anti-mouse IgG. Cell surface bound cetuximab and IgAb_wtFc (IgAb_049) were detected by FITC-conjugated goat anti-human IgG (Dianova, cat.: 109-095-088). After last staining step, the cells were washed again and resuspended in 0.2 mL of FACS buffer containing 2 µg/mL propidium iodide (PI) (Sigma, cat.: P4170) in order to exclude dead cells. The fluorescence of $2-5\times10^3$ living cells was measured using a Beckman-Coulter FC500 MPL flow cytometer using the MXP software (Beckman-Coulter, Krefeld, Germany) or a Millipore Guava EasyCyte flow cytometer (Merck Millipore, Schwalbach, Germany). Mean fluorescence intensities of the cell samples were calculated using CXP software (Beckman-Coulter) or Incyte software (Merck Millipore, Schwalbach, Germany). After subtracting the fluorescence intensity values of the cells stained with the secondary and tertiary reagents alone, the values were used for non-linear regression analysis using the GraphPad Prism software (GraphPad Prism version 6.00 for Windows, GraphPad Software, La Jolla California USA). For the calculation of $K_D$, the equation for one-site-binding (hyperbola) was used.

Results

The anti-EGFR IgG cetuximab, used as a positive control, and the human IgG1 with the anti-EGFR Fab-domains from imgatuzumab (IgAb_065) inhibited EGF-induced EGFR phosphorylation in a dose-dependent manner with $EC_{50}$ values in the range of 7 µg/mL-9 µg/mL.

EGFR/CD16A tandem diabody, EGFR/CD16A scFv-IgAb_01, Fc-silenced IgG1 (IgAb_047), and wt IgG1 (IgAb_049), all containing the anti-EGFR Fab domain comprising the variable domains as depicted in SEQ ID NOs:1 and 2, inhibited EGFR phosphorylation with substantial lower potency with $EC_{50}$ values higher than 100 µg/mL.

Notably, scFv-IgAb_02 containing the anti-EGFR domains as depicted in SEQ ID NOs:1 and 2 as scFv fused to the C-terminus of Fc showed no or only very little inhibitory effect on EGF-induced EGFR phosphorylation.

These data suggest that scFv-IgAb_02 exhibits reduced receptor antagonism compared with cetuximab and imgatuzumab and, hence, exhibits reduced toxicity in tissues dependent on EGFR signaling for tissue homeostasis, e.g. the skin.

Figure 13:
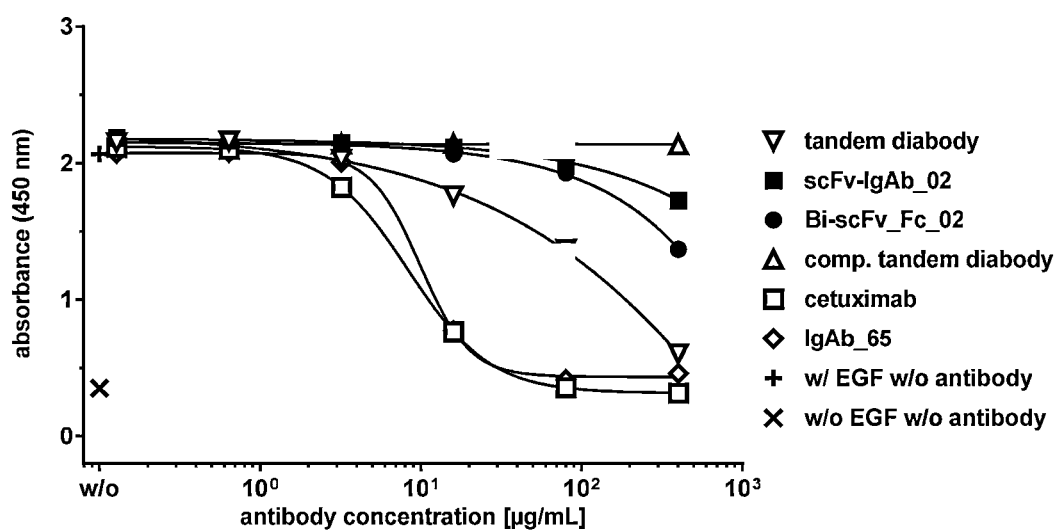
FIG. 13 shows inhibition of EGF-induced EGFR phosphorylation by various anti-EGFR antibody constructs and control antibodies on A-431 cells. Phosphorylated EGFR was measured in phosphorylation ELISA and plotted as absorbance at 450 nm.
Figure 14:
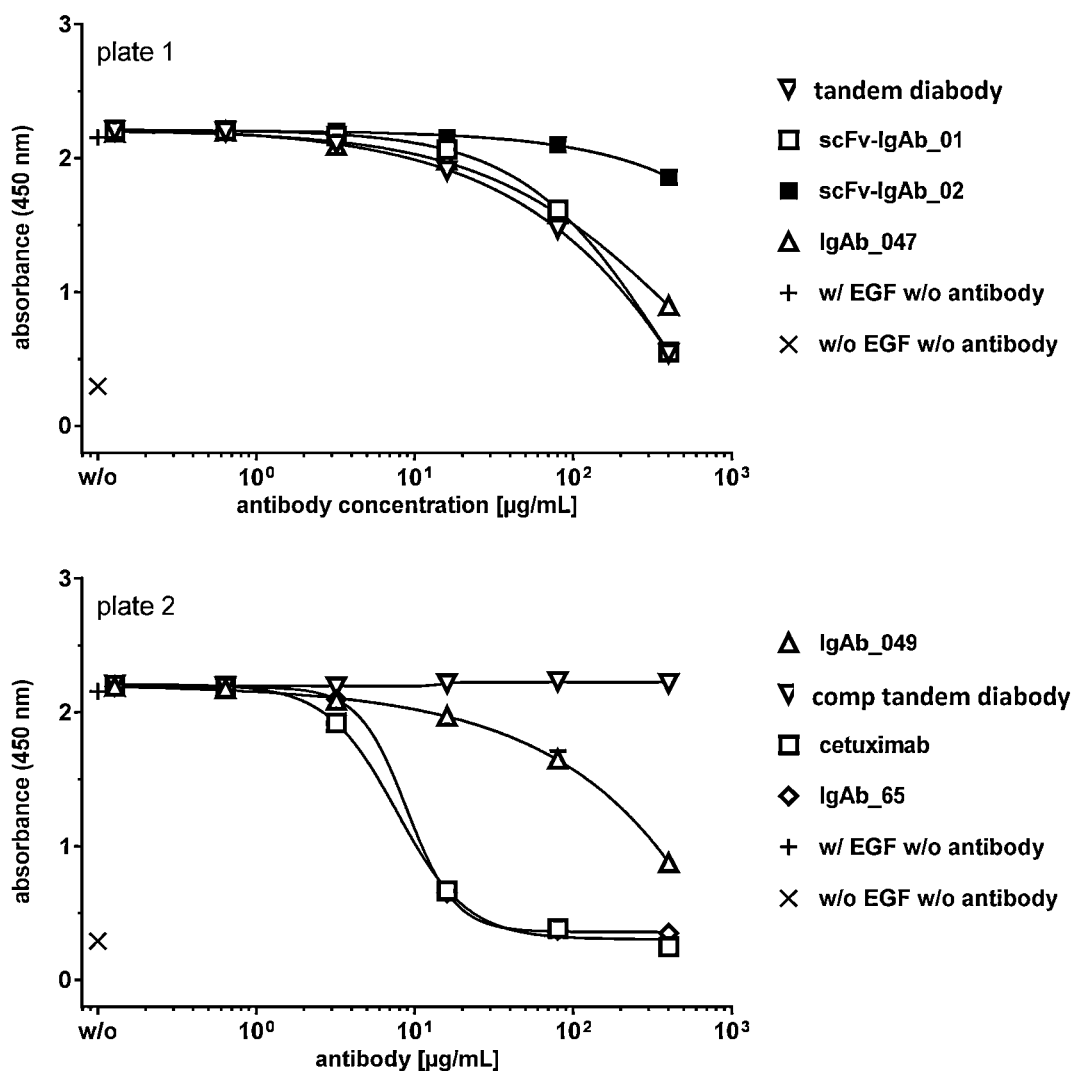
FIG. 14 shows inhibition of EGF-induced EGFR phosphorylation by various anti-EGFR antibody constructs and control antibodies on A-431 cells. Phosphorylated EGFR was measured in phosphorylation ELISA and plotted as absorbance at 450 nm.

CD19/CD16A tandem diabody, used as a negative control, showed no inhibition of EGFR phosphorylation. Results from the experiment depicted in FIG. 13 and FIG. 14 are summarized in Table 8.

TABLE 8

Tabulated summary of EGFR phosphorylation assays using A-431 cells.

| construct | description | results from Exp. 1 | results from Exp. 2 |
|---|---|---|---|
| Tandem diabody | EGFR/CD16A tandem diabody with anti-EGFR Fv domain and anti-CD16A Fv domain | $EC_{50}$: >100 µg/mL | $EC_{50}$: >100 µg/mL |
| Comp. Tandem diabody | CD19/CD16A tandem diabody with anti-CD19 Fv domain and anti-CD16A Fv domain | no inhibition | no inhibition |
| scFv-IgAb_01 | EGFR/CD16A antibody construct with anti-EGFR Fab domain and anti-CD16A scFv domain | n.t. | $EC_{50}$: >100 µg/mL |
| scFv-IgAb_02 | EGFR/CD16A antibody construct with anti-EGFR scFv domain and anti-CD16A Fab domain | No or only low inhibitory effect | No or only low inhibitory effect |
| Bi-scFv-Fc_02 | EGFR/CD16A antibody construct with anti-EGFR scFv domain and anti-CD16A scFv domain | No or only low inhibitory effect | n.t. |
| IgAb_slFc | Human IgG1 with silenced Fc and anti-EGFR Fab domain | n.t. | $EC_{50}$: >100 µg/mL |
| IgAb_wtFc | Human IgG1 with wt Fc and anti-EGFR Fab domain | n.t. | $EC_{50}$: >100 µg/mL |
| IgAb_wtFc | Human IgG1 with wt Fc and anti-EGFR Fab domain derived from imgatuzumab | $EC_{50}$: 9.9 µg/mL | $EC_{50}$: 8.9 µg/mL |
| cetuximab | Chimeric IgG1 with wt Fc and anti-EGFR Fab domain derived from clone C225 | $EC_{50}$: 8.3 µg/mL | $EC_{50}$: 7.7 µg/mL | n.t., not tested

The differences among the tested antibody constructs and formats in their inhibitory effect on EGF-induced EGFR phosphorylation cannot be attributed to differences in their affinity to EGFR, since the apparent binding affinity to A-431 cells ($K_D$ value) does not correlate with the potency in inhibition of EGF-induced EGFR phosphorylation (Table 9; FIG. 14).

For instance: EGFR/CD16A tandem diabody exhibits a slightly lower/or similar binding affinity to A-431 cells when compared with scFv-IgAb_02 or Bi-scFv-Fc_02, but possesses a substantial stronger phosphorylation inhibitory effect than scFv-IgAb_02 or Bi-scFv-Fc_02. Or: the apparent affinity to EGFR on A-431 of scFv-IgAb_01 or Bi-scFv-Fc_02 is in the same range as for cetuximab, but the inhibitory effect on EGFR phosphorylation of scFv-IgAb_01 or Bi-scFv-Fc_02 is substantially lower relative to cetuximab.

Since all tested EGFR/CD16A antigen-binding proteins contain the same binding domains to EGFR and to CD16A, the effects on EGF-mediated phosphorylation of EGFR should be associated with intrinsic properties of the 3D structure of the antigen-binding proteins. Only scFv-IgAb_02 and Bi-scFv-Fc_02, which contain the EGFR-binding domains in the C-terminal position show this specific property (no or only minor inhibitory effect on phosphorylation).

It is therefore expected, that this unique property translates in an improved side effect profile versus e.g. cetuximab. The reason behind this assumption is, that the skin toxicity seen with EGFR inhibitors is due to an unwanted inhibitory effect on EGFR signaling of keratinocytes of the skin, as described previously.

TABLE 9

Apparent affinities of various anti-EGFR antigen-binding proteins determined in cell binding experiments on A-431 cells at 37° C.

| construct | description | results from phosphorylation assay $EC_{50}$ if applicable | apparent affinity ($K_D$ [nM]) to A-431 cells at 37° C. n | mean | SD |
|---|---|---|---|---|---|
| Tandem diabody | EGFR/CD16A tandem diabody with anti-EGFR Fv domain and anti-CD16A Fv domain | >100 µg/mL | 14 | 2.9 | 0.84 |
| Comp. Tandem diabody | CD19/CD16A tandem diabody with anti-CD19 Fv domain and anti-CD16A Fv domain | No inhibition of EGFR phosphorylation | 0 | n.t. | n.a. |
| scFv-IgAb_01 | EGFR/CD16A antibody construct with anti-EGFR Fab domain and anti-CD16A scFv domain | >100 µg/mL | 4 | 2.0 | 0.46 |
| scFv-IgAb_02 | EGFR/CD16A antibody construct with anti-EGFR scFv domain and anti-CD16A Fab domain | No or only low inhibitory effect on EGFR phosphorylation | 6 | 2.6 | 0.48 |

TABLE 9-continued

Apparent affinities of various anti-EGFR antigen-binding proteins
determined in cell binding experiments on A-431 cells at 37° C.

| construct | description | results from phosphorylation assay EC$_{50}$ if applicable | apparent affinity (K$_D$ [nM]) to A-431 cells at 37° C. | | |
|---|---|---|---|---|---|
| | | | n | mean | SD |
| Bi-scFv-Fc_02 | EGFR/CD16A antibody construct with anti-EGFR scFv domain and anti-CD16A scFv domain | No or only low inhibitory effect on EGFR phosphorylation | 6 | 2.2 | 0.69 |
| EGFR IgAb_slFc | Human IgG1 with silenced Fc and anti-EGFR Fab domain | >100 µg/mL | 0 | n.t. | n.a. |
| EGFR IgAb_wtFc | Human IgG1 with wt Fc and anti-EGFR Fab domain | >100 µg/mL | 2 | 1.5 | 0.07 |
| EGFR IgAb_wtFc | Human IgG1 with wt Fc and anti-EGFR Fab domain derived from imgatuzumab | 8.9 µg/mL | 0 | n.t. | n.a. |
| cetuximab | Chimeric IgG1 with wt Fc and anti-EGFR Fab domain derived from clone C225 | 7.7 µg/mL | 7 | 2.0 | 2.05 | n, number of independent experiments;
mean K$_D$ value of n experiments;
SD, standard deviation,
n.t., not tested,
n.a., not applicable

Example 7

Evaluation of Pharmacokinetic (PK) Properties:
Determination of Serum Concentrations of scFv-IgAb_02 and of Bi-scFv-Fc_02 in CD1 Mice after a Single Intravenous Injection of the Respective Antibody:

PK assessment of EGFR/CD16A antigen-binding proteins was performed in single dose PK studies in CD1 mice. It has to be noted that there is no binding to the nominal targets in the CD1 mouse and target mediated effects cannot not be investigated in this model. However, the test items ae fully cross reactive to the murine FcRn receptor and FcRn effects on the half-life should be fully reflected. Two test systems were implemented to evaluate the EGFR/CD16A antigen-binding proteins in a PK analysis in mouse serum. The first test system has been set up in an ELISA format, and subsequently this platform was transferred to a MSD reader platform. The two assays revealed consistent serum concentrations and PK data.

scFv-IgAb_02 and Bi-scFv-Fc_02 application solutions for intravenous slow bolus injection of the 300 µg/mouse dose were prepared to obtain a final concentration of 300 µg/250 µL. Two PK studies were performed:

Blood withdrawal (sample collection was performed before treatment (Pre-dose), up to 168 hours post treatment (study 1) and up to 504 hours post treatment (study 2).

Number of bleedings/animal: 3
Number of animals per time point: 4
Blood collection was performed by punction of retrobulbar venous plexus under Isoflurane anesthesia. Blood volume was 100-150 µL (approx. 30 µL serum).

Animals were sacrificed directly after 3rd terminal bleeding. Whole blood was processed to serum and all samples were immediately frozen and stored below −65° C.

In the first study, assessment of serum pharmacokinetics over a time period of 168 hours (7 days) was performed by MSD and ELISA.

The half-lives were:
scFv-IgAb_02: 79 hours
Bi-scFv-Fc_02: 96 hours

A subsequent study was performed, since the blood-collection period was too short and the terminal elimination time could not be calculated, appropriately. Therefore, in the second study, assessment of serum pharmacokinetics was performed over a time period of 504 hours (21 days) for scFv-IgAb_02 only (ELISA determination of serum concentrations). The observation time was sufficient, and clearly reliable half-life calculation in the elimination phase could be performed. The half-life for scFv-IgAb_02 was:
329.2 hours Determination of the Half-Lives in Mice:
Pharmacokinetic parameters were determined by non-compartmental using the program PK Solutions (Version 2.0) from Summit Research Services (68911 Open Field Dr., Montrose, Colorado 81401 USA).

Example 8

Inhibition of EGF-Stimulated EGFR Phosphorylation in A-431 and A-549 Cells

To compare the inhibitory effect of different EGFR/CD16A antigen-binding proteins on EGF-induced EGFR signaling, phosphorylation assays with A-431 and A-549 cells were performed.

Material & Methods:
Culture of Cell Lines

A-431 (ATCC, cat.: CRL-1555) and A-549 (DSMZ, cat.: ACC 107) were cultured under standard conditions in DMEM medium supplemented with 10% heat-inactivated FCS, 2 mM L-glutamine and 100 IU/mL penicillin G sodium and 100 µg/mL streptomycin sulfate (all components from Invitrogen) at 37° C. in a humidified atmosphere with 5% $CO_2$.

Phosphorylation Assay
In brief, aliquots of $5 \times 10^4$ A-431 or A-549 cells were seeded in individual wells of a 96 well plate in DMEM medium supplemented with 10% heat-inactivated FCS, 2 mM L-glutamine and 100 IU/mL penicillin G sodium and 100 µg/mL streptomycin sulfate (all components from Invitrogen) for 20-22 h at 37° C. in a humidified atmosphere with 5% $CO_2$. Cells were then starved for 4 h in medium without serum before serial dilutions of the indicated antibody constructs were added. After 30 min incubation at 37° C., EGF (Sigma, cat.: 10605-HNAE-250) was added to a final concentration of 100 ng/mL and cultures were further incubated for 10 min at 37° C. before cells were washed with ice-cold PBS (Invitrogen, cat.: 14190-169) and lysed and used for relative quantification of phosphorylated EGFR using an Phospho-EGFR ELISA Kit (RayBiotech, cat.: PEL-EGFR-Y) according to the instructions of the manufacturer. The absorbance was measured at 450 nm with a multiplate reader (Victor 3, Perkin Elmer). Absorbance values were analyzed and plotted using GraphPad Prism software (GraphPad Prism version 6.00 for Windows, GraphPad Software, La Jolla California USA).

Results

Figure 15A:
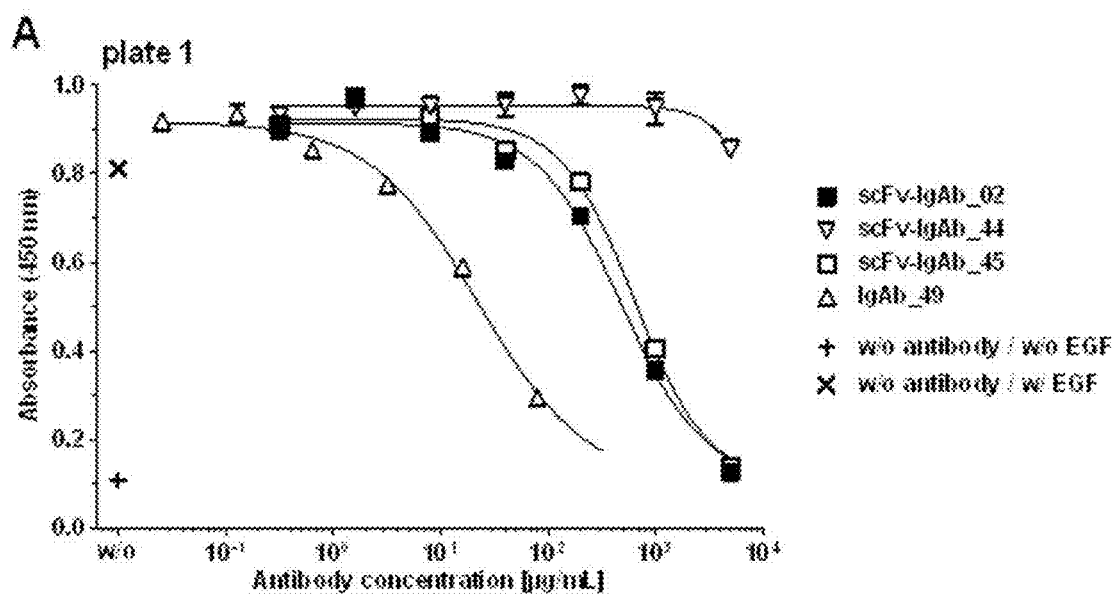
FIGS. 15A and 15B show inhibition of EGF-stimulated EGFR phosphorylation in A-431 cells (FIG. 15A) and A-549 cells (FIG. 15B). Phosphorylated EGFR was measured in phosphorylation ELISA and plotted as absorbance at 450 nm.
Figure 15B:
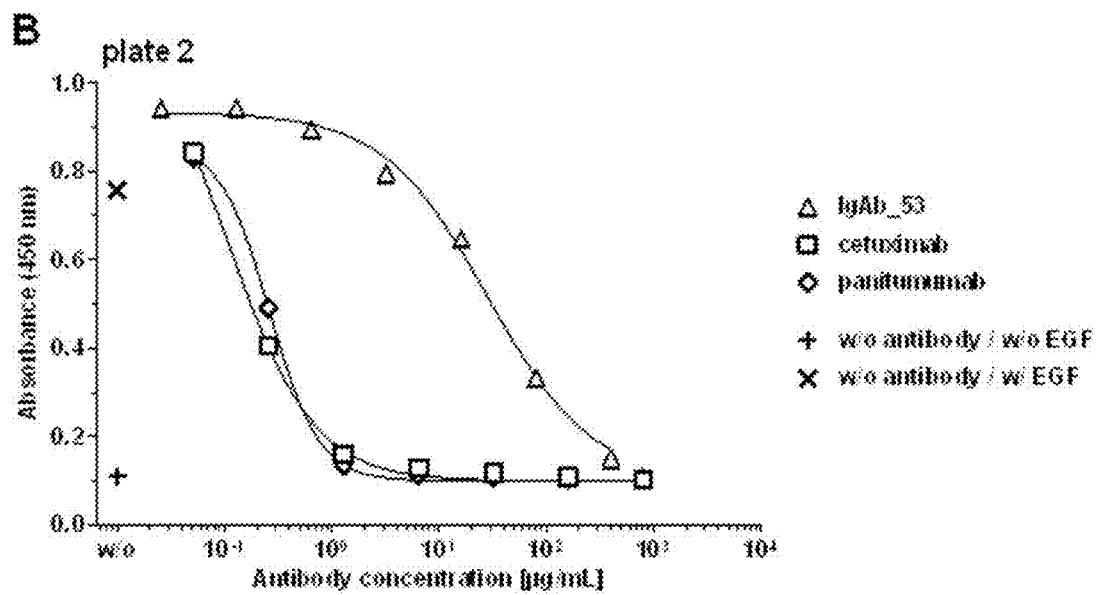

The inhibitory effect of EGFR/CD16A scFv-IgAb (scFv-IgAb_02), reference anti-EGFR IgG cetuximab and panitumumab, and various control antibodies on the phosphorylation of EGFR upon stimulation with EGF was assessed using A-431 cells (FIG. 15a) and A-549 cells (FIG. 15b). A description of the antibodies and a summary of $EC_{50}$ values determined for the dose-dependent inhibition of EGFR phosphorylation are presented in Table 10.

The anti-EGFR IgG cetuximab and panitumumab, used as reference antibodies, inhibited EGF-induced EGFR phosphorylation in a dose-dependent manner with an $EC_{50}$ value of 7.7 µg/mL and 8.2 µg/mL on A-431 and 0.1 µg/mL and 0.3 µg/mL on A-549 cells, respectively. The RSV/CD16A scFv-IgAb (scFv-IgAb_44) was used as a negative control and showed no inhibitory impact on EGF-stimulated EGFR phosphorylation.

Wt IgG1 (IgAb_49) and Fc-enhanced IgG1 (IgAb_53), all containing the anti-EGFR Fab domain comprising the variable domains as depicted in SEQ ID NOs:1 and 2, inhibited EGFR phosphorylation with substantial lower potency than cetuximab or panitumumab with $EC_{50}$ values that were 5-6-fold higher on A-431 cells, and 75-300-fold higher on A-549 cells.

Notably, scFv-IgAb_02 and scFv-IgAb_45 containing the anti-EGFR domains as depicted in SEQ ID NOs:1 and 2 as scFv fused to the C-terminus of Fc, and differing only in the Fab domains, showed only an inhibitory effect on EGF-induced EGFR phosphorylation at high concentrations with $EC_{50}$ values in the range of 1.1 mg/mL to 1.5 mg/mL on A-431 cells and 478 µg/mL to 643 µg/mL on A-549 cells.

These data suggest that scFv-IgAb_02 exhibits reduced receptor antagonism compared with IgG1 antibodies containing the identical anti-EGFR Fv domains (IgAb_49 & IgAb_53). When compared with cetuximab-mediated inhibition the difference was even stronger, and ~200-fold lower potency on A-431 cells, and ~5000-fold lower potency on A-549 cells could be observed for EGFR/CD16A scFv-IgAb_02. From these data it could be concluded that the reduced EGFR signaling inhibition of scFv-IgAb_02 is associated with an improved side effect profile and translates into less skin toxicity that is usually seen with anti-EGFR antibodies with strong receptor antagonistic properties, such as cetuximab and panitumumab.

TABLE 10

Tabulated summary of EGFR phosphorylation assays using A-431 and A-549 cells.

| construct | description | $EC_{50}$ [µg/mL] on A-431 cells[§] | $EC_{50}$ [µg/mL] on A-549 cells[$] |
|---|---|---|---|
| scFv-IgAb_02 | EGFR/CD16A antibody construct with anti-EGFR scFv domain and anti-CD16A Fab domain | 1518 | 477.8 |
| scFv-IgAb_44 | RSV/CD16A antibody construct with anti-RSV scFv domain and anti-CD16A Fab domain | no | no |
| scFv-IgAb_45 | EGFR/RSV antibody construct with anti-EGFR scFv domain and anti-RSV Fab domain | 1139 | 643.1 |
| IgAb_49 | Human IgG1 with wt Fc and anti-EGFR Fab domain | 47.9 | 22.3 |
| IgAb_53 | Human IgG1 with Fc-enhanced (S239D/I332E) Fc and anti-EGFR Fab domain | 41.0 | 28.4 |
| cetuximab | Chimeric IgG1 with wt Fc and anti-EGFR Fab domain derived from clone C225 | 7.7 | 0.1 |
| panitumumab | Human IgG2a anti-EGFR | 8.2 | 0.3 |

[§]bottom constrained to 0.25 for non-linear regression analysis and calculation of $EC_{50}$ values.

[$]bottom constrained to 0.1 for non-linear regression analysis and calculation of $EC_{50}$ values.

Example 9

Assessment of Inhibition of Phosphorylation of EGFR-Signaling Proteins Upon EGF Treatment by scFv-IgAb_02

Methods:

Cultivation of Cell Lines.

A-431 (ATCC, cat.: CRL-1555) were cultured under standard conditions in DMEM medium supplemented with 10% heat-inactivated FCS, 2 mM L-glutamine and 100 IU/mL penicillin G sodium and 100 µg/mL streptomycin sulfate (all components from Invitrogen). Cells were cultivated in starvation medium (RPMI 1640 medium (Invitrogen) with 1% FCS) for 1 h before use in experiments.

Inhibition of EGFR-Signaling with Antibodies.

$3 \times 10^6$ cells were, if indicated, incubated with 20 µg/mL of the respective antibody for 1 h at 37° C. in a humidified atmosphere. Subsequently, cells were stimulated by addition of recombinant human EGF (ThermoFisher, #10605HNAE250) at a concentration of 100 ng/mL for either 5 or 15 min at 37° C. in a humidified atmosphere. Cells were then washed and lysed with Radioimmuneprecipitation-assay buffer (RIPA) containing 150 mM NaCl (AppliChem, #131659.1211), 1% Triton X 100 (Roth, #30512), 0.05% Sodium deoxycholate (Sigma, #D6750), 0.1% SDS (Roth, #CN30.1), 50 mM Tris (Biomol, #08003.1), protease inhibitors (Roche, #11697498001) and phosphatase inhibitors (Roche, #4906845001) for 45 min on ice. After centrifugation for 15 min at 300×g and 4° C., supernatants were mixed 1:1 with reducing sample buffer containing 62.5 mM Tris-HCl pH 6.8, 2% SDS, 5% Glycerin (Applichem, #A2926,055), 200 mM Bromphenolblue (Roth, #A512.1), 0.1M DTT (Roth, #6908.2) and heated to 95° C. for 10 min and subsequently subjected to SDS-PAGE on a 4-20% Criterion TGX Precast SDS-PAGE Gel (Bio-Rad, #5678095) in 1× Tris/Glycine/SDS buffer (Bio-Rad, #1610732) at 300V for 22 min. For immunoblotting, proteins were transferred onto PVDF membranes (BioRad, #1704157) using the Trans-Blot Turbo Transfer System (Bio-Rad) according to manufacturer's instructions. Membranes were then blocked in 5% skim milk (Sigma, #70166) in TBS for 1 h at room temperature, washed three times with TBS and incubated primary antibody diluted as recommended by the supplier in 5% BSA (Sigma, #A3059), 0.05% $NaN_3$ (Roth, #K305.1) in TBS, for 1 h at room temperature or overnight at 4° C. Membranes were subsequently washed three times with TBS and incubated with HRP-conjugated secondary antibody in TBS and 5% skim milk for 1 h at room temperature. Following washing with TBS, chemiluminescence after addition of ECL solution (ThermoFisher, #32209) was measured using the ChemiDoc MP Imaging System (Bio-Rad) and analyzed using Image Lab Software (BioRad). A list of antibodies tested is depicted in table 11, a list of antibodies used for the detection of proteins is depicted in table 12.

TABLE 11

Antibodies tested.

| construct | description |
|---|---|
| scFv-IgAb_02 | Bispecific EGFR/CD16A antibody; |
| cetuximab | chimeric IgG1 anti-EGFR; Erbitux; PZN 11191428 |
| scFv-IgAb_45 | Bispecific EGFR/RSV antibody |

TABLE 12

Antibodies used for the detection of signaling proteins.

| antibody | clone | #cat | supplier |
|---|---|---|---|
| Rabbit, anti-EGFR | D38B1 | 4267 | Cell Signaling |
| Rabbit, anti-pEGFR (Y1068) | D7A5 | 3777 | Cell Signaling |
| Rabbit, anti-Erk1/2 | 137F5 | 4695 | Cell Signaling |
| Rabbit, anti-pErk1/2 T202/Y204 | D13.14.4E | 4370 | Cell Signaling |
| Rabbit, anti-Akt | C67E7 | 4691 | Cell Signaling |
| Rabbit, anti-Akt (S473) | D9E | 4060 | Cell Signaling |
| Rabbit, anti-GAPDH | D16H11 | 5174S | Cell Signaling |
| Goat, anti-Rabbit-HRP conjugated | n/a | 111-035-144 | Dianova |

Results

To assess the effect of EGFR/CD16A scFv IgAb_02 on the inhibition of EGF-induced EGFR-signaling, A-431 cells were incubated with scFv-IgAb_02, and as a control, with EGFR/RSV scFv-IgAb_45, or anti-EGFR IgG1 cetuximab. Stimulation was performed for 5 min and 15 min, respectively, and induction of phosphorylation was assessed via Western Blot.

Figure 16:
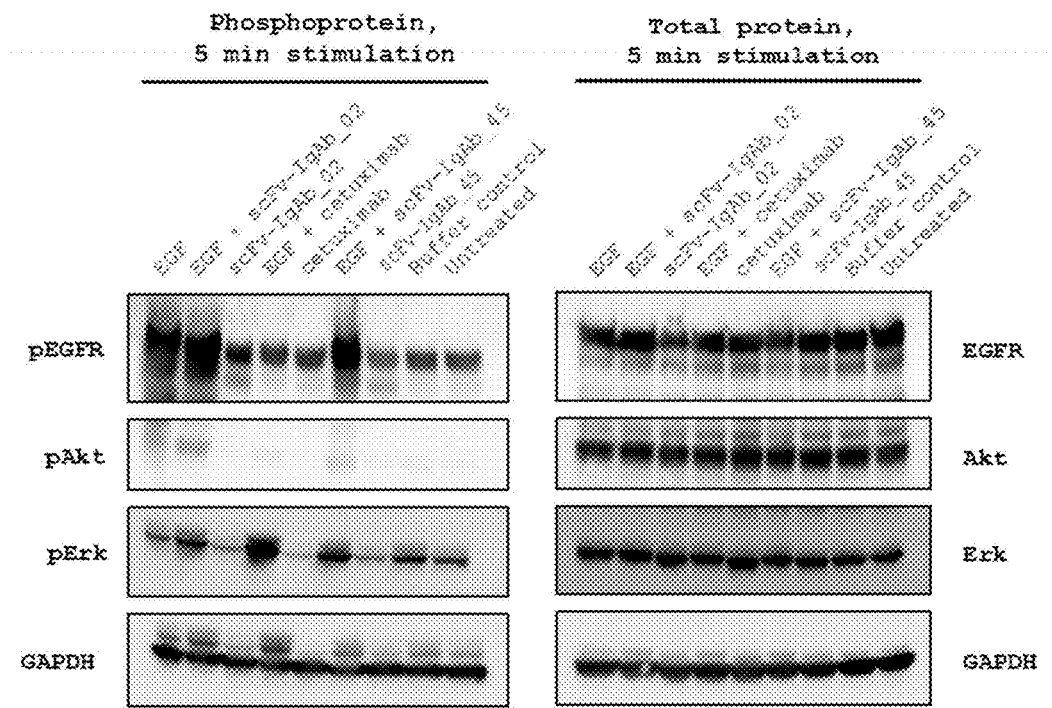
FIG. 16 shows Western Blot membranes of samples stimulated for 5 min with EGF. Phosphoproteins (left panel of blots) and total proteins (right panel of blots) are depicted, respectively.
Figure 17:
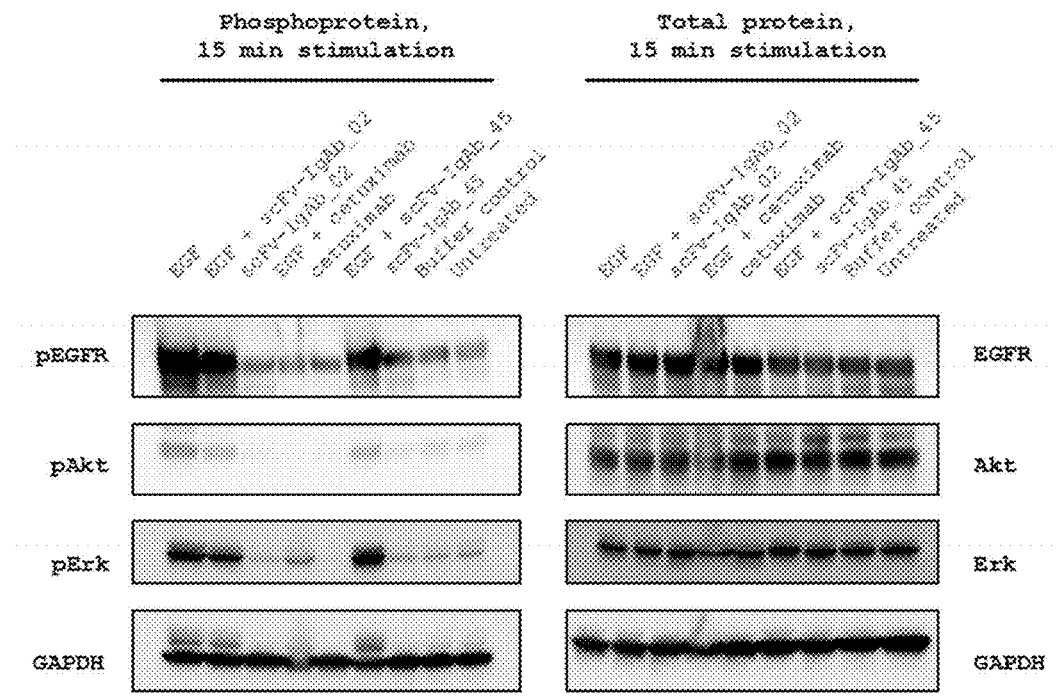
FIG. 17 shows Western Blot membranes of samples stimulated for 15 min with EGF. Phosphoproteins (left panel of blots) and total proteins (right panel of blots) are depicted, respectively.
Figure 18:
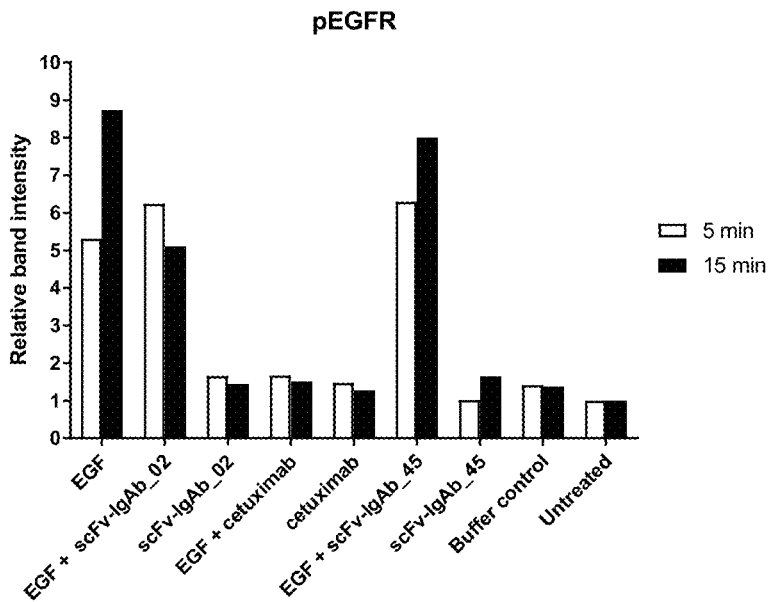
FIG. 18 shows quantification of band intensities of pEGFR. The intensity of the GAPDH-signal of a respective lane was normalized to the GAPDH-signal intensity of the untreated control. The intensity of pEGFR was normalized to the pEGFR of the untreated control. Depicted relative band intensity corresponds to normalized pEGFR-signal, relative to normalized GAPDH-signal. White bars: 5 min stimulation, Black bars: 15 min stimulation.
Figure 19:
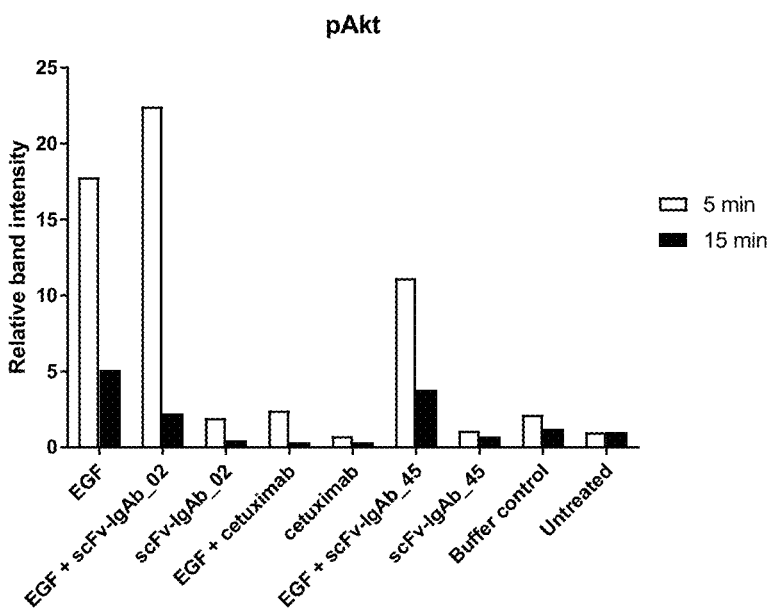
FIG. 19 shows quantification of band intensities of pAkt. The intensity of the GAPDH-signal of a respective lane was normalized to the GAPDH-signal intensity of the untreated control. The intensity of pAkt was normalized to the pAkt of the untreated control. Depicted relative band intensity corresponds to normalized pAkt-signal, relative to normalized GAPDH-signal. White bars: 5 min stimulation, Black bars: 15 min stimulation.
Figure 20:
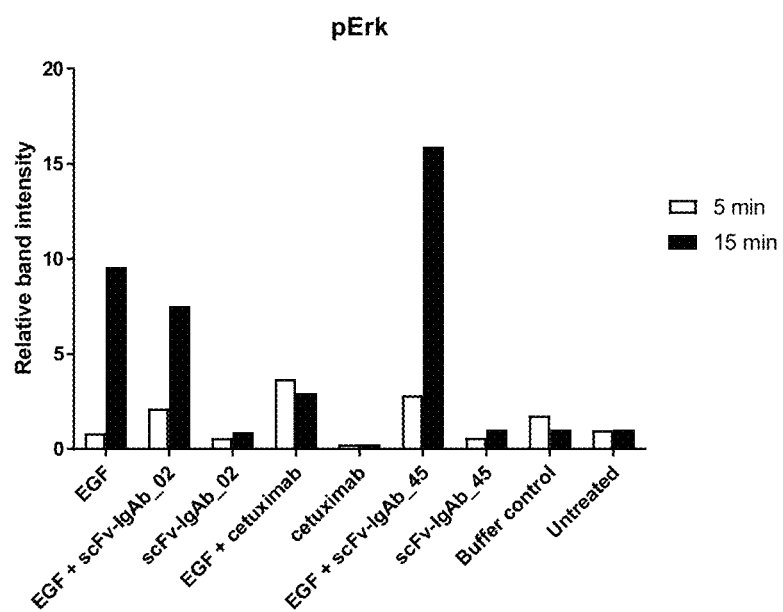
FIG. 20 shows quantification of band intensities of pErk. The intensity of the GAPDH-signal of a respective lane was normalized to the GAPDH-signal intensity of the untreated control. The intensity of pErk was normalized to the pErk of the untreated control. Depicted relative band intensity corresponds to normalized pErk-signal, relative to normalized GAPDH-signal. White bars: 5 min stimulation, Black bars: 15 min stimulation.

Blot images are depicted in FIGS. 16 and 17. Quantification of relative band intensities for the respective phosphoproteins is depicted in FIGS. 18, 19, and 20.

The results presented in this example show phosphorylation of EGFR, Akt, and Erk upon stimulation of A-431 cells with EGF. Phosphorylation of EGFR and its inhibition was measurable after 5 min and 15 min stimulation with EGF (FIG. 18), whereas differences in pAkt and pErk were most pronounced after 5 min (FIG. 19) or 15 min (FIG. 20), respectively.

Pre-incubation of cells with cetuximab blocked EGF-stimulation of EGFR, Akt, and Erk, whereas pre-incubation with EGFR/CD16A scFv-IgAb_02 or EGFR/RSV scFv-IgAb_45 had no or only marginal inhibitory effect on EGF-stimulated phosphorylation of EGFR, Akt, and Erk. EGF-stimulation and antibody treatment had no impact on total protein levels of EGFR, Akt, and Erk.

Example 10

Cytokine Release from PBMC Induced by scFv-IgAb_02

Isolation of PBMC from Buffy Coats

PBMCs were isolated from buffy coats (German Red Cross, Mannheim, Germany) by density gradient centrifugation. The buffy coat samples were diluted with a two-to-threefold volume of PBS (Invitrogen, cat.: 14190-169), layered on a cushion of Lymphoprep (Stem Cell Technologies, cat.: 07861) and centrifuged at 800×g for 25 min at room temperature w/o brake. PBMC located in the interface were collected and washed 3 times with PBS before they were cultured in complete RPMI 1640 medium supplemented with 10% FCS overnight without stimulation.

Culture of Cell Lines

A-431 (ATCC, cat.: CRL-1555) were cultured under standard conditions in DMEM medium supplemented with 10% heat-inactivated FCS, 2 mM L-glutamine and 100 IU/mL penicillin G sodium, and 100 µg/mL streptomycin sulfate (all components from Invitrogen) at 37° C. in a humidified atmosphere with 5% $CO_2$.

Quantification of Cytokines Released from PBMC Stimulated by scFv-IgAb_02 in Presence or Absence of EGFR+ Target Cells $5 \times 10^5$ primary human PBMC were co-cultured with EGFR+ A-431 target cells at an effector to target ratio of 50:1. Co-cultures were incubated in complete RPMI 1640 medium supplemented with 10% FCS in presence or absence of increasing concentrations of scFv-IgAb_02 in a total volume of 200 µL. Background cytokine levels in the cultures were assessed by including cultures of PBMC or A-431 cells only, in presence or absence of scFv-IgAb_02. As positive control, co-cultures were incubated with Dyna-Beads Human T-Activator CD3/CD28 (Gibco, cat. 11132D), stimulating the release of all tested cytokines from T cells within the PBMC population. All cultures were incubated for 4 h, 24 h or 48 h at 37° C. and 5% $CO_2$ in a humidified incubator before centrifugation at 70×g for 2 min at RT. Cell culture supernatants (70 µL) were harvested from each well and transferred to round-bottom 96-well microplates for storage at −80° C. until quantification of cytokines by bead-based multiplex methodology at Bioassay GmbH (Heidelberg, Germany) using BD™ Cytometric Bead Array (CBA) Human Th1/Th2 Cytokine Kit II (BD Bioscience). Results were analyzed and plotted using GraphPad Prism for Windows (V6.00/7.03, GraphPad Software, La Jolla, California, USA).

Determination of the NK Activation Status Upon PBMC Co-Culture in Presence or Absence of Target Cells and scFv-IgAb_02

NK cell activation was assessed by flow cytometry of cell pellets after harvesting the supernatant for cytokine quantification. For this, cells were washed and resuspended in CD56-PC7 (5 µL/test; Beckman Coulter, A21692), CD25-PE (10 µL/test; Beckman Coulter, A07774) and CD69-PC5 (5 µL/test; Beckman Coulter, IM2656) in a total staining volume of 100 µL FACS buffer (PBS containing 2% heat-inactivated FCS and 0.1% sodium azide). After 15 min incubation on ice in the dark, cells were washed, resuspended in FACS buffer and analyzed by flow cytometry.

Results

Release of six cytokines, namely Interleukin-2 (IL-2), Interleukin-4 (IL-4), Interleukin-6 (IL-6), Interleukin-10 (IL-10), Tumor Necrosis Factor (TNF) and Interferon-γ (IFN-γ) was assessed in the cell culture supernatants after 4 h, 24 h and 48 h co-culture of PBMC and A-431 in presence or absence of increasing concentrations of scFv-IgAb_02.

Incubation of PBMC alone and in presence of A-431 did not result in detectable increases in IL-2, IL-4, IL-6, IL-10, TNF-α, or IFN-γ while stimulation with CD3/CD28 activator beads led to a marked release of all tested cytokines (data not shown). Exposure of PBMC to increasing concentrations of scFv-IgAb_02 led to marginal release of all cytokines. Maximal cytokine release from PBMC induced by scFv-IgAb_02 alone was considered as background level of the respective cytokine (Table 13).

Cytokine levels in cell culture supernatants of PBMC and A-431 targets that increased above 5× background levels were considered as positive signals and are summarized in Table 13. These analyses revealed an scFv-IgAb_02-induced, dose-dependent release of IL-6, TNF-α and IFN-γ in co-cultures of PBMC and EGFR+ target cells to the indicated time-points. No scFv-IgAb_02-induced release of all other tested cytokines above background levels could be detected.

TABLE 13

Summary of released cytokines upon co-culture of primary human PBMC and EGFR+ A-431 target cells and increasing concentrations of scFv-IgAb_02. Potency ($EC_{50}$) and maximum response ($E_{max}$) of scFv-IgAb_02 induced cytokine release is shown.

| cytokine | incubation time [h] | $EC_{50}$ [pM] | $E_{max}$ [pg/mL] | background level [pg/mL] |
|---|---|---|---|---|
| IL-6 | 24 | 3.7 | 1569.8 | 19.5 |
| | 48 | 7.1 | 1448.8 | 14.2 |
| TNF-α | 4 | 5.6 | 385.4 | 14.9 |
| | 24 | 17.3 | 105.0 | 4.0 |
| IFN-γ | 4 | 10.5 | 18.1 | 2.5 |

Figure 21:
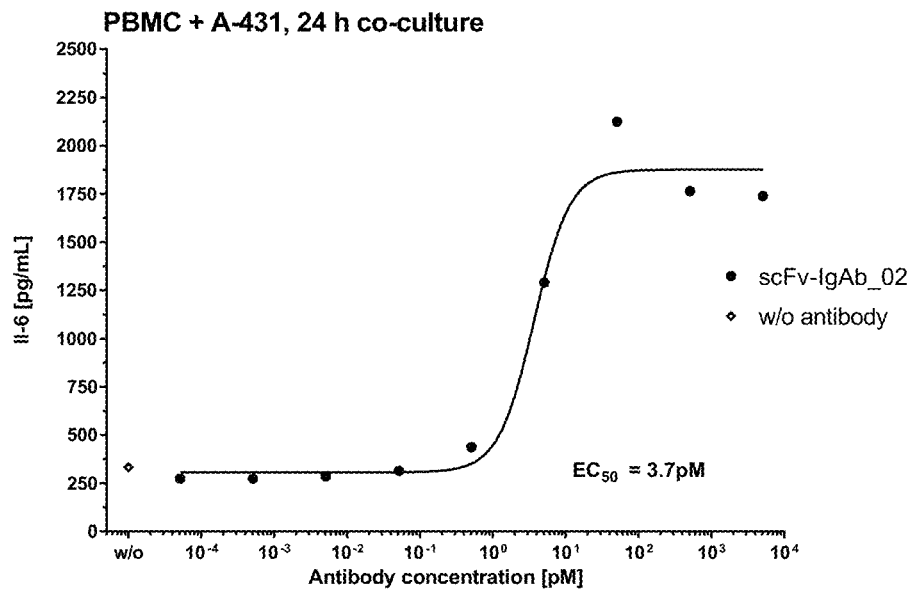
FIG. 21 shows scFv-IgAb_02-induced release of IL-6 by PBMC upon co-culture with EGFR⁺ A-431 cells. Incubation time of the co-culture in presence or absence of increasing concentrations of scFv IgAb_02 is indicated. Background level of IL-6 release in absence of A-431 target cells is indicated below the graph.
Figure 21:
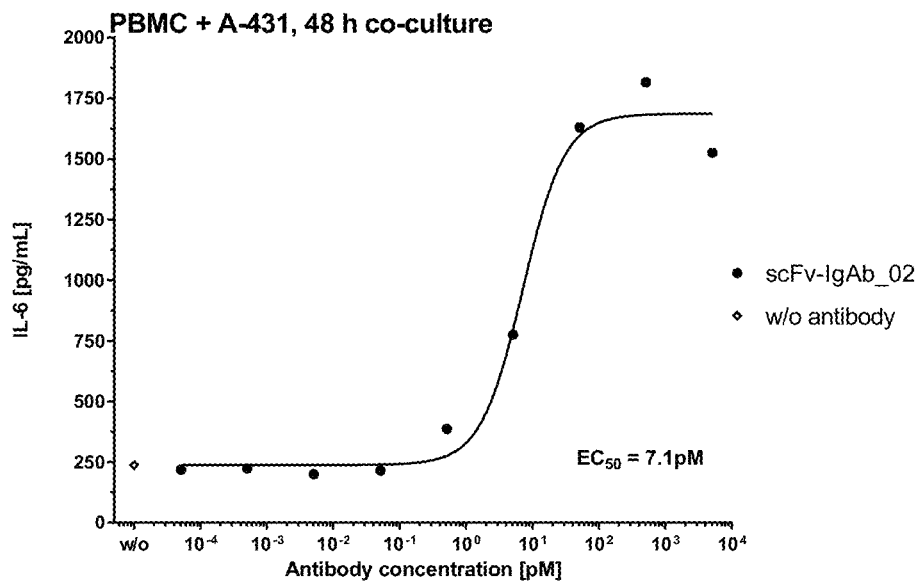

ScFv-IgAb_02-induced, dose-dependent release of IL-6 was detected after 24 h and 48 h co-culture of PBMC and A-431 with potencies ($EC_{50}$) of 3.7 µM and 7.1 µM, respectively (Table 13; FIG. 21).

Figure 22:
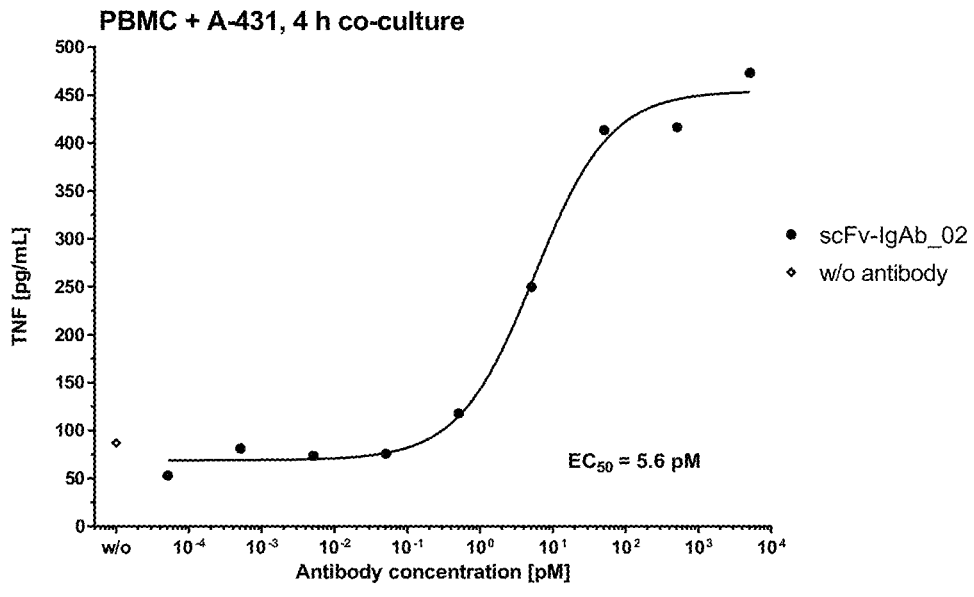
FIG. 22 shows scFv-IgAb_02-induced release of TNF-α by PBMC upon co-culture with EGFR⁺ A-431 cells. Incubation time of the co-culture in presence or absence of increasing concentrations of scFv-IgAb_02 is indicated. Background level of TNF-α release in absence of A-431 target cells is indicated below the graph.
Figure 22:
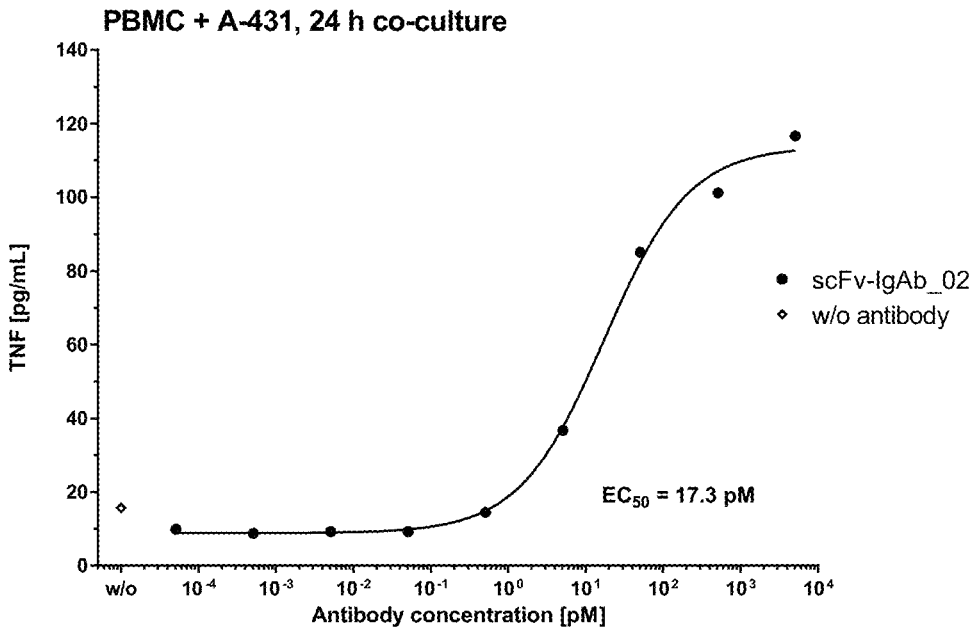
Figure 23:
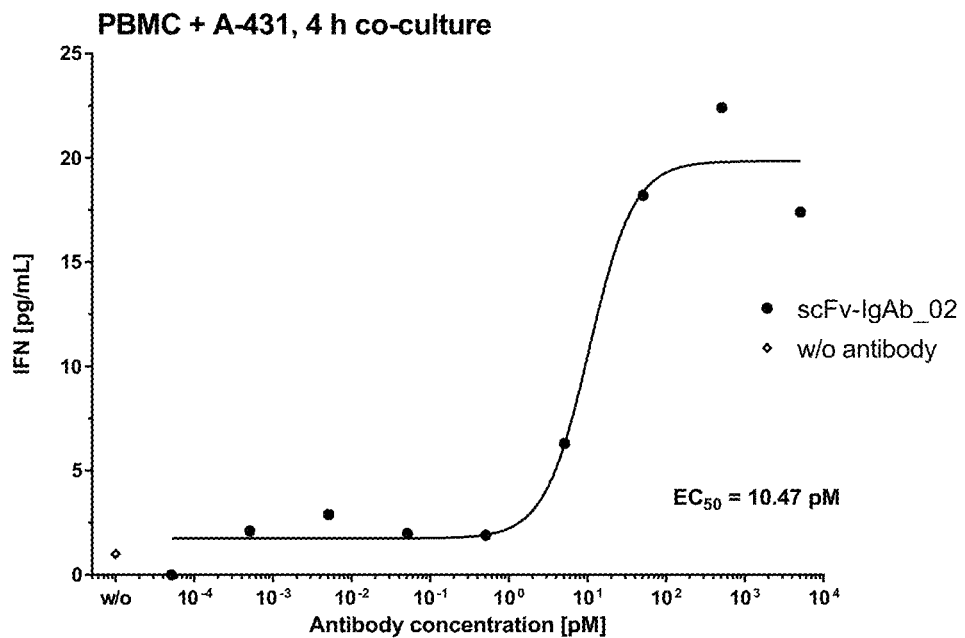
FIG. 23 shows scFv-IgAb_02-induced release of IFN-γ by PBMC upon co-culture with EGFR⁺ A-431 cells after 4 h co-culture. Background level of IFN-γ release in absence of A-431 target cells is indicated below the graph.
Figure 24:
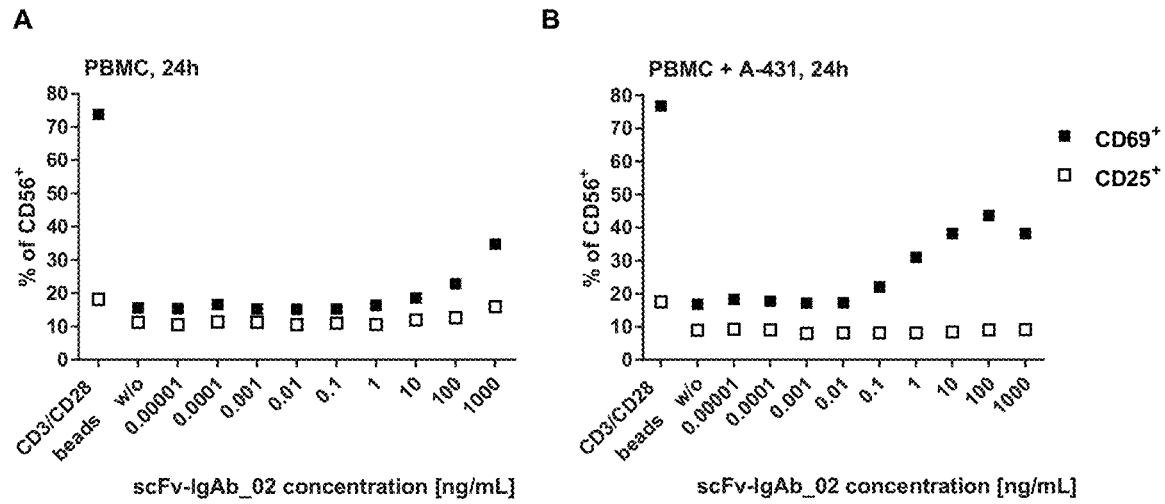
FIG. 24 shows activated NK cells after 24 h co-culture of PBMC with scFv-IgAb_02 in presence or absence of EGFR⁺ A-431. ScFv-IgAb_02 induced increase of activated CD56⁺ NK cells expressing CD69 and CD25 in cultures of PBMC (A) and PBMC+A-431 cells (B).
Figure 25:
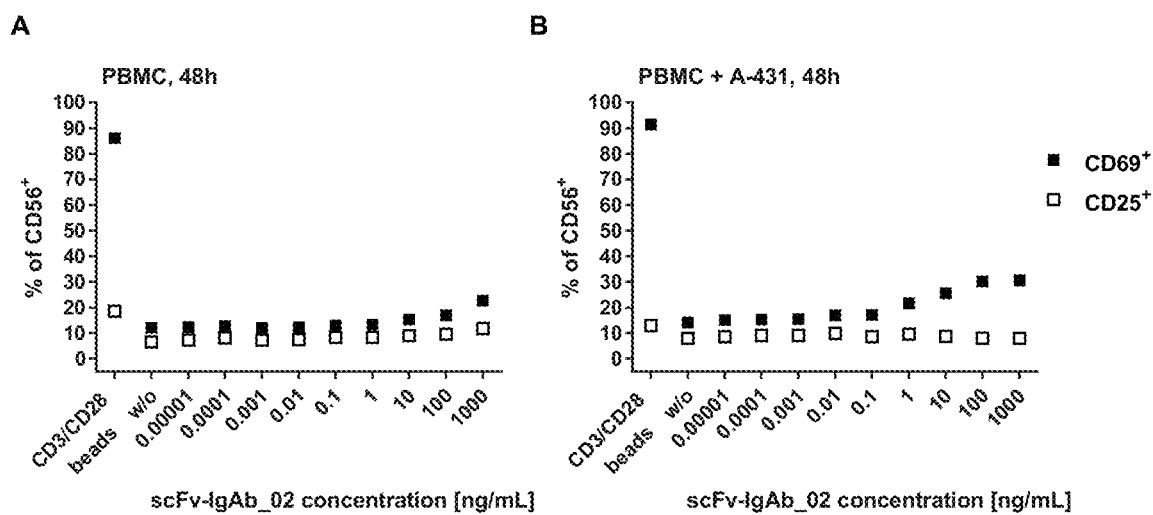
FIG. 25 shows activated NKs after 48 h co-culture of PBMC with scFv-IgAb_02 in presence or absence of EGFR⁺ A-431. ScFv-IgAb_02 induced increase of activated CD56⁺ NK cells expressing CD69 and CD25 in cultures of PBMC (A) and PBMC+A-431 cells (B).

ScFv-IgAb_02 induced secretion of TNF-α could be assessed after 4 h and 24 h respectively (Table 13; FIG. 22), while elevated levels of IFN-γ could exclusively be measured after 4 h (Table 13; FIG. 23). An antibody dose-dependent increase of $CD69^+$ NK cells could be detected after 24 h and 48 h co-culture of PBMC and A-431 cells with a maximum of 44% supporting NK cell activation in the applied assay setup (FIG. 24B, FIG. 25B). Elevated levels of $CD69^+$ NK cells could also be detected after 24 h culture in absence of A-431 cells though exclusively at high concentrations of scFv-IgAb_02. No obvious scFv-IgAb_02-induced increase of the late NK cell activation marker CD25 was detected upon co-culture of PBMC in presence of A-431 cells for 24 h and 48 h respectively.

Example 11

Pharmacodynamic In Vivo Studies (POC)

Several in vivo POC studies of scFv-IgAb_02 were conducted with prophylactic and therapeutic dosing regimen in a humanized mouse model bearing xenotransplanted human EGFR+ tumours. The model consisted of hydrodynamically IL-15-boosted NOD/Shi-scid/IL-2Rγ$^{null}$ mice (NOG), prior engrafted with cord blood-derived human $CD34^+$ hematopoietic stem cells. Tumours were engrafted by subcutaneous inoculation of $1 \times 10^6$ A-431 cells on Day 0 (D0). The model was provided by TransCure BioServices SAS, France. It was demonstrated in pre-studies to achieve reliable reconstitution with human immunological effector cells (including human NK cells) and consistent A-431 tumour take and growth. This model appears presently to be the best humanized mouse model with regard to human NK cell reconstitution (yielding in the order of $1-2 \times 10^4$ human NK cells per mL of peripheral blood).

Four studies using scFv-IgAB_02 in the above murine model are presented in more detail below.

In the prophylactic treatment settings (i.e. treatment starting at the time of tumour inoculation) a trend of reduced tumour growth by scFv-IgAB_02 treatment was observed at 5 mg/kg and significant inhibition of tumour growth from 10 mg/kg onwards. In the therapeutic settings (i.e. treatment starting when the tumour reached a volume between 50-100 mm$^3$) significant inhibition of tumour growth by scFv-IgAB_02 treatment was also seen from a dose level of 10 mg/kg onwards, demonstrating anti-tumoural efficacy of scFv-IgAB_02 in the murine model.

According to the above described examples showing in vitro studies it is concluded that scFv-IgAB_02 has a dual anti-tumoural mode of action consisting of A) induction of ADCC and/or ADCP against EGFR+ tumour cells by forcing an interaction with CD16A+ NK cells and/or macrophages B) a direct growth inhibiting effect on EGFR+ tumour cells by blocking EGFR receptor, with induction of ADCC (and/or ADCP) being the dominant anti-tumoural effect exerted by scFv-IgAB_02 (in contrast to cetuximab, where direct growth inhibition by blocking EGFR phosphorylation is dominant).

Two of the murine POC studies were conducted with an intention to delineate ADCC from direct growth inhibition by including RSV/EGFR as a reference item. RSV/EGFR in this case is a molecule containing the identical EGFR-binding region and Fc part of scFv-IgAB_02, but is devoid of the CD16A-binding moiety which is replaced by an irrelevant RSV binding domain (Respiratory-Syncytial-Virus) —thus not able to induce ADCC.

The first of the two RSV/EGFR studies showed a slightly better anti-tumoural effect of scFv-IgAB_02 than RSV/EGFR (thus pointing towards contribution of ADCC to the overall anti-tumoural efficacy in the murine A-431 tumour model). The second study, however, comparing several different dose levels of scFv-IgAB_02 and RSV/EGFR in the prophylactic and therapeutic treatment arms showed equal potency of both variants in the murine A-431 tumour model. It is therefore assumed that the overlapping pharmacodynamic effects of scFv-IgAB_02 appear to be dominated by inhibition of phosphorylation (EGFR signaling), in the reconstituted murine model, potentially due to the low number of NK cells present in this model when compared to the human situation.

Thus the humanized murine model, though providing a general POC for the anti-tumoural efficacy of scFv-IgAB_02 in vivo, is not suitable to delineate induction of ADCC against EGFR+ tumours as the dominant effector mechanism of scFv-IgAB_02.

In an initial study different bispecific EGFR/CD16 antigen-binding proteins (scFv-IgAB_02 and structural variants/controls) were compared in a prophylactic setting in A431-tumor bearing eHIS-IL15-huNOG mice. IL-15-boosted NOD/Shi-scid/IL-2Rγnull mice (NOG), engrafted with cord blood-derived CD34+ hematopoietic stem cells (HuNOG) were subcutaneously inoculation of 1×106 A431 cells on Day 0 (D0). Animals received weekly intravenous applications of scFv-IgAB_02 and Bi-scFv Fc_02 at 5 mg/kg and 10 mg/kg for four weeks (q7d×4) starting on day1. Cetuximab served as a positive control at 5 and 0.5 mg/kg using the identical dosing intervals.

Figure 26:
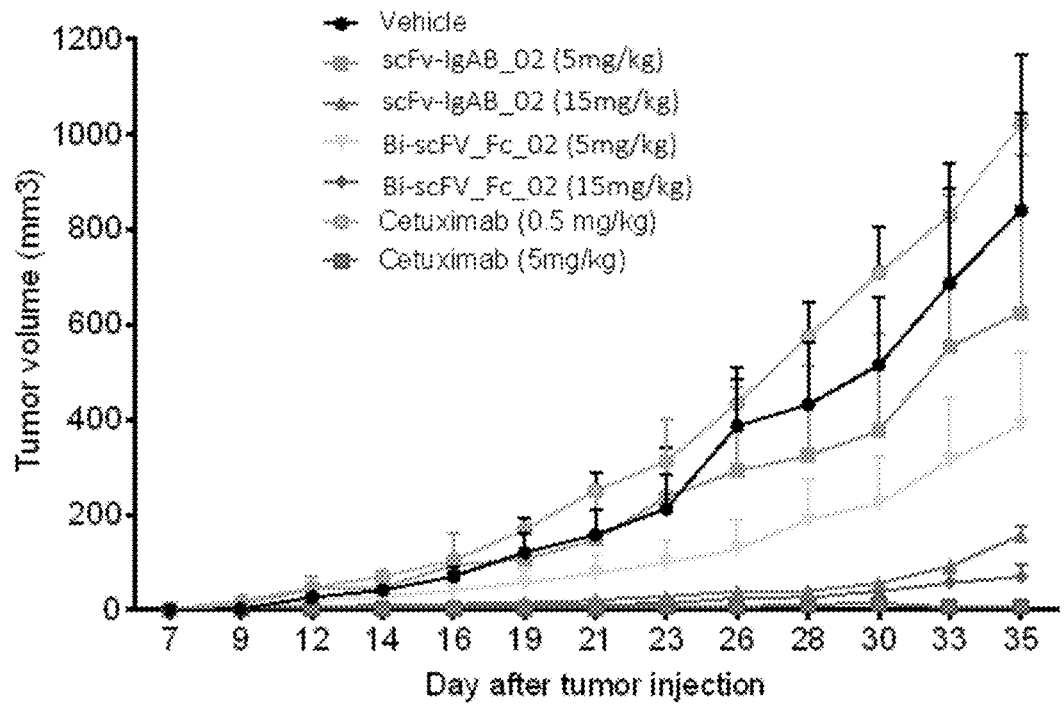
FIG. 26 shows the tumour growth from Day 7 to Day 35 in Transcure prophylactic study.

Cetuximab (5 mg/kg), scFv-IgAB_02 (15 mg/kg) and Bi-scFv Fc_02 (15 mg/kg) induced a significant delay in tumour growth compared to vehicle in all treated animals as soon as twelve days after tumour cell engraftment (FIG. 26). Low dose (5 mg/kg) of scFv-IgAB_02 and Bi-scFv Fc_02 tend to slow down the tumour growth (not significant) whereas Cetuximab (0.5 mg/kg) had no effect.

In a subsequent efficacy study scFv-IgAB_02 was tested at different dose levels in a prophylactic setting. IL15-boosted NOD/Shi-scid/IL-2Rγnull mice (NOG), engrafted with cord blood-derived CD34+ hematopoietic stem cells (HuNOG) were subcutaneously inoculated with 1×106 A431 cells on Day 0 (D0). Based on the humanization rate and the percentage of NK cells in human leukocytes, HuNOG mice were randomized into treatment groups (n=7). Animals received weekly intravenous applications of scFv-IgAB_02 at 5, 15, and 45 mg/kg; (q7d×4) starting on D1.

Figure 27:
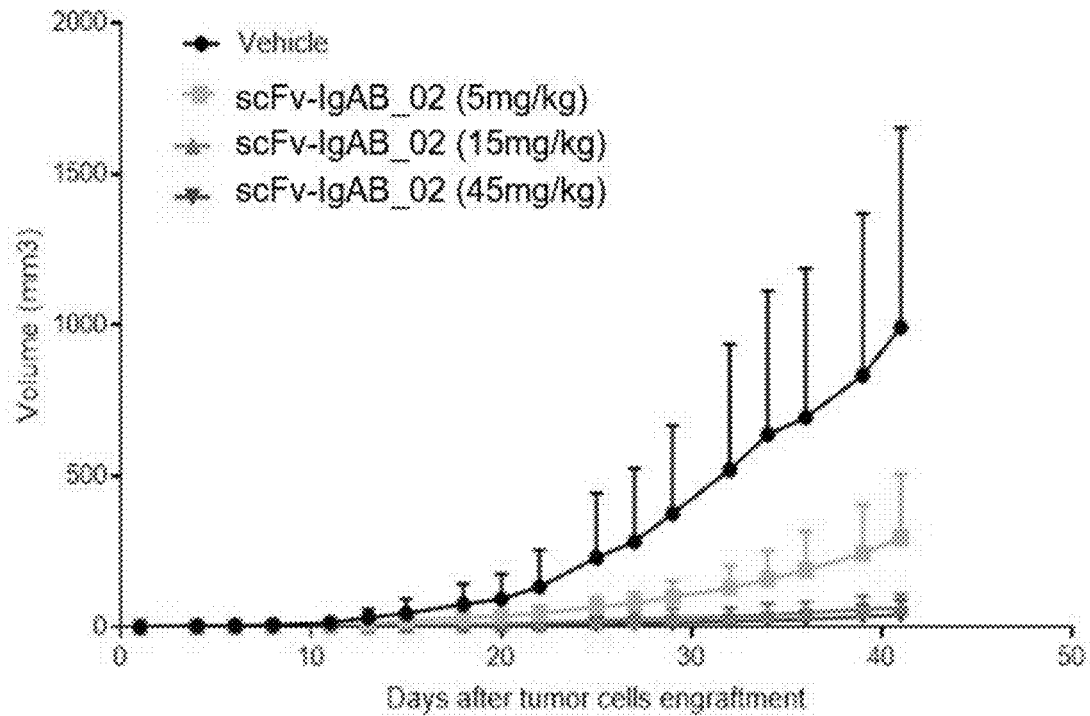
FIG. 27 shows the tumour growth in Transcure prophylactic study.

As soon as 11 days after tumour cell engraftment, a significant tumour volume reduction was observed between the vehicle group and the groups treated with scFv-IgAB_02 (15 mg/kg) and scFv-IgAB_02 (45 mg/kg). 41 days after tumour cell engraftment (at sacrifice) a weekly injection of scFv-IgAB_02 (5 mg/kg) reduced tumour volume by 70% compared to vehicle. scFv-IgAB_02 (15 and 45 mg/kg) reduced tumor volume by 95% comparison to vehicle (FIG. 27).

In summary, a trend of reduced tumour growth by scFv-IgAB_02 treatment was observed at 5 mg/kg. Significant inhibition at 15 mg/kg and 45 mg/kg was seen indicating a dose dependency.

In another Transcure study efficacy evaluation was performed in a therapeutic setting.

In parallel in the same study scFv-IgAB_02 was compared to a control construct RSV-EGFR in a prophylactic setting. RSV-EGFR is a molecule containing the EGFR-binding region of scFv-IgAB_02 and the identical Fc part, but is devoid of the CD16A-binding moiety, which is replaced by an irrelevant RSV binding domain.

IL15-boosted NOD/Shi-scid/IL-2Rγnull mice (NOG), engrafted with cord blood-derived CD34+ hematopoietic stem cells (HuNOG) were subcutaneously inoculated with 1×106 A431 cells on Day 0 (D0). Based on the humanization rate and the percentage of NK cells in human leukocytes, HuNOG mice were randomized into treatment groups (n=7).

Therapeutic Treatment:

When A-431 tumors reached a size of 50-100 mm3 on D17 animals received weekly intravenous applications of scFv-IgAB_02 at 5, 15, and 45 mg/kg; (q7d×4).

Figure 28A:
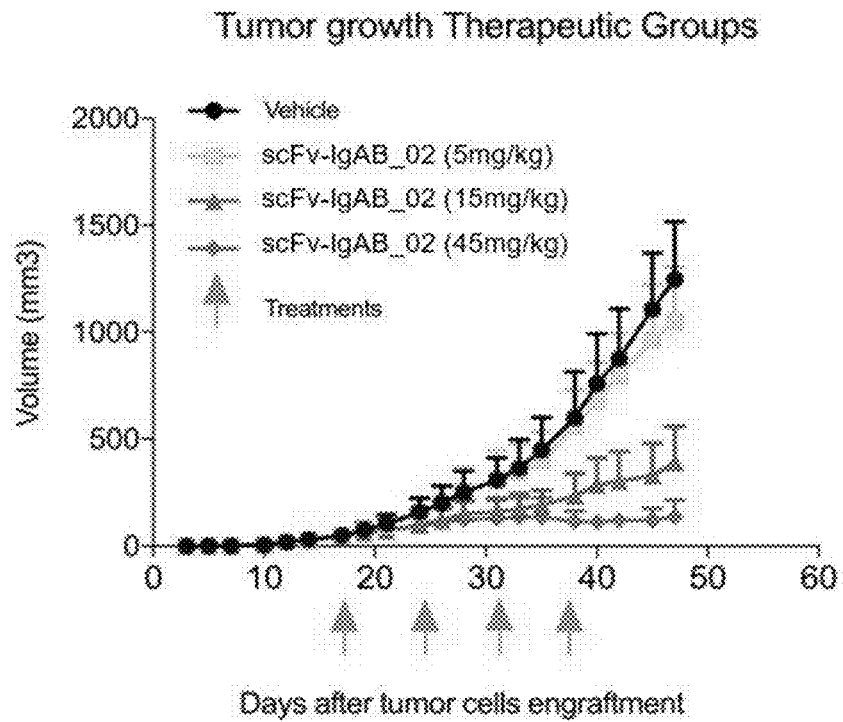
FIGS. 28A and 28B: Effect of RSV-EGFR and different scFv-IgAB_02 concentrations on A431 tumour growth in a prophylactic (FIG. 28A) and therapeutic setting (FIG. 28B). Legend: Mean±SD of the tumour growth is represented for each group. N=7-8 per therapeutic groups, N=12 per prophylactic groups.

The two highest doses of scFv-IgAB_02 (15 mg/kg and 45 mg/kg) significantly reduced A431 tumour growth by respectively 70 and 90%. scFv-IgAB_02 at 5 mg/kg had no significant effect on tumour growth (FIG. 28A).

Prophylactic Treatment:

Animals received weekly intravenous applications of scFv-IgAB_02 or RSV-EGFR at 45 mg/kg starting on D1 (q7d×4).

Figure 28B:
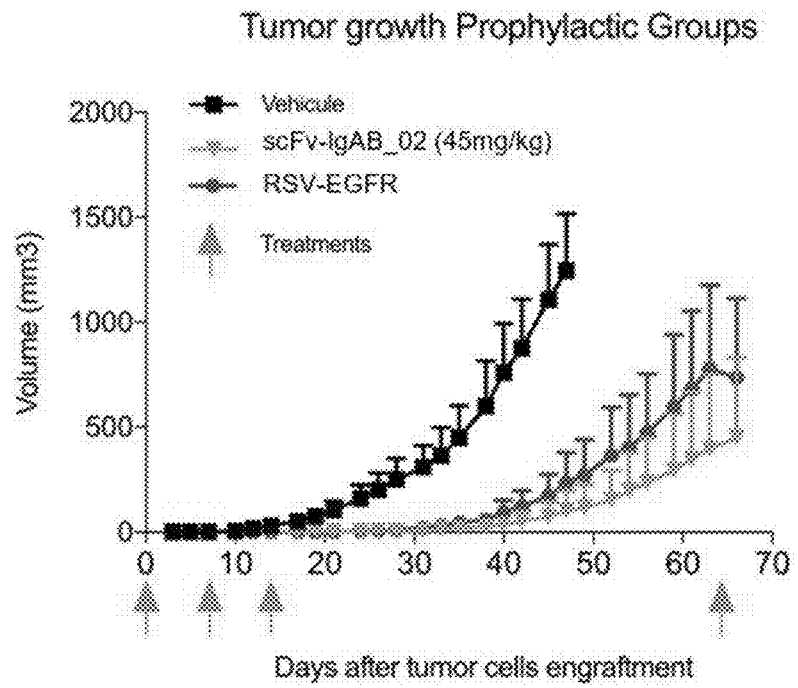

Treatment with scFv-IgAB_02 (45 mg/kg) and RSV-EGFR (45 mg/kg) completely prevented tumour growth during the first 24 days after tumour cell engraftment. Starting at D24, tumour growth in the RSV-EGFR group was faster than in the scFv-IgAB_02 group. At sacrifice, mean tumour volume reached 837 mm3 in the RSV-EGFR group but only 449 mm3 in the scFv-IgAB_02 group (FIG. 28B). This difference was statistically significant suggesting an additional pharmacodynamic effect by ADCC of scFv-IgAB_02 on top direct growth inhibiting effect on EGFR+ tumour cells by blocking EGFR phosphorylation by both constructs.

To investigate the impact/proof for existence of ADCC as mode of action in the A431 tumor model in hu-mice, prophylactic treatments were tested in the low dosage range of scFv-IgAB_02 and RSV-EGFR. Furthermore, therapeutic treatment with scFv-IgAB_02 and RSV-EGFR was compared at a single dose level.

Ninety IL15-boosted humanized mice were randomized in two arms based on their humanization rate and amount of NK cells (CD56+ cells).

Prophylactic arm: The prophylactic groups (6 mice per group) were engrafted with 1×10⁶ A431 cells on the right flank. One day after tumour cell inoculation, mice received the treatment (intravenous injection, once per week for four weeks and a last injection three days before sacrifice). Day 0 is defined as the day of tumour cell inoculation. The following treatments were performed:

Group 1: IL15-huNOG+A431+Vehicle (weekly, IV)
Group 2: IL15-huNOG+A431+scFv-IgAB_02 (1.25 mg/kg, weekly, IV)
Group 3: IL15-huNOG+A431+scFv-IgAB_02 (2.5 mg/kg, weekly, IV)
Group 4: IL15-huNOG+A431+scFv-IgAB_02 (5 mg/kg, weekly, IV)
Group 5: IL15-huNOG+A431+scFv-IgAB_02 (10 mg/kg, weekly, IV)
Group 6: IL15-huNOG+A431+RSV/EGFR (1.25 mg/kg, weekly, IV)
Group 7: IL15-huNOG+A431+RSV/EGFR (2.5 mg/kg, weekly, IV)
Group 8: IL15-huNOG+A431+RSV/EGFR (5 mg/kg, weekly, IV)
Group 9: IL15-huNOG+A431+RSV/EGFR (10 mg/kg, weekly, IV)

All mice were sacrificed 35 days after tumour cell engraftment. Flow cytometry analysis was performed on peripheral blood and tumour infiltrating cells.

Therapeutic arm: The therapeutic groups were engrafted with $1\times10^6$ A431 cells on the right flank. When the tumour reached a volume of 50-100 mm$^3$, mice were randomized based on their tumour volume, humanization rate and NK cells number and treatment was initiated. Day 0 is defined as the day of the first treatment. Group 10 animals, as well 6 additional animals in groups 11 and 12 served as satellite animals for flow cytometry analysis.

The following treatments were performed (intravenous injection, once per week for four weeks and a last injection three days before sacrifice):

Group 10: IL15-huNOG+A431+Vehicle (weekly, IV) n=6
Group 11: IL15-huNOG+A431+scFv-IgAB_02 (10 mg/kg, weekly, IV) n=15
Group 12: IL15-huNOG+A431+RSV/EGFR (10 mg/kg, weekly, IV) n=15

Satellite mice were sacrificed 3 days and 10 days after treatment initiation. Three mice from Group 11 and three from Group 12 were sacrificed at each time point. Twenty-four days after treatment initiation, three mice with the highest tumour volume from each group were sacrificed. All remaining mice from the therapeutic groups were sacrificed 30 days after treatment initiation. Flow cytometric analysis was performed on peripheral blood and tumour infiltrating cells on the satellite mice. 30 days after treatment initiation, lymphocytes were also phenotyped by flow cytometry.

Figure 29:
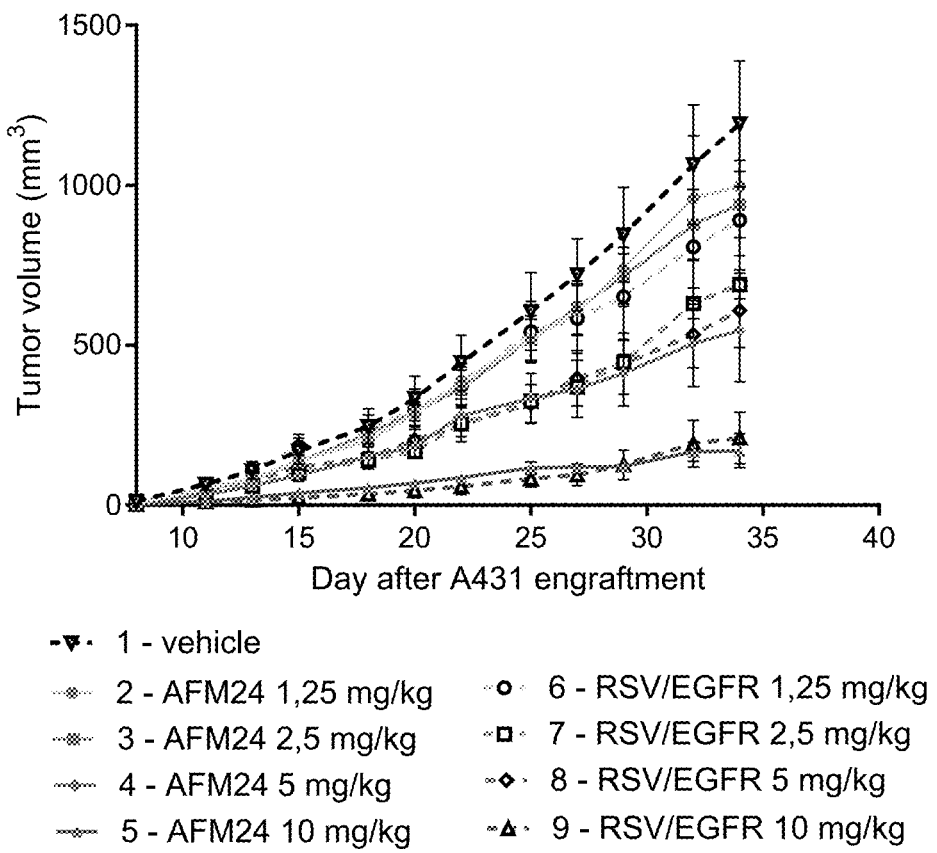
FIG. 29 shows prophylactic arm of a Transcure study. In tumor outgrowth study scFv-IgAb_02 and control antibody construct RSV/EGFR were administered as described in appended example 11.

Prophylactic treatments in the human epidermoid carcinoma A431 humanized mouse tumour model with scFv-IgAB_02 and RSV/EGFR significantly reduced tumour volume at the dose of 10 mg/kg. The lower dose (1.25, 2.5 and 5 mg/kg) did not significantly inhibit tumour growth the in comparison to the vehicle. Treatment with RSV/EGFR and treatment with scFv-IgAB_02 had similar effect on tumour growth at every dose tested (FIG. 29). The NK cell count in this humanized mouse model may be too low for a full initiation of an effective ADCC against the tumor cells.

Flow cytometry analysis on the peripheral blood of the satellite animals revealed that blood cell count remained constant over time but activation markers on NK cells (CD69 and NKp44) significantly increased after tumour cell engraftment.

Phenotype of tumour infiltrating immune cells was also investigated. In cell number, no significant difference was observed between the groups for CD45, T and NK cells. Noteworthy, the highest dose of both scFv-IgAB_02 and RSV/EGFR significantly increased the expression of CD69 and NKp44 at the surface of NK cells by comparison to the vehicle group.

Figure 30:
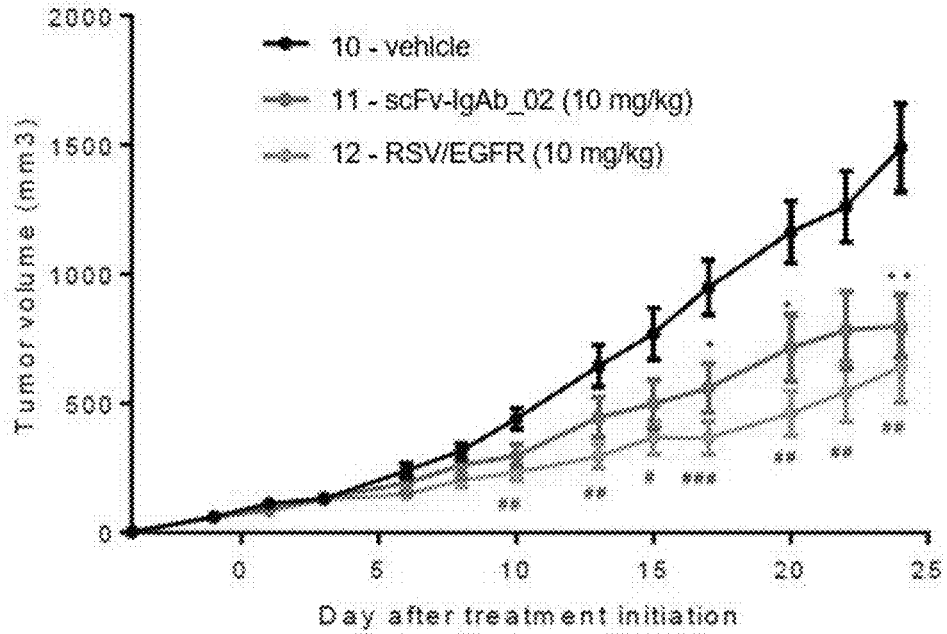
FIG. 30 shows therapeutic arm of Transcure study. A significant tumour growth reduction with 10 mg/kg treatment with scFv-IgAb_02 and control antibody construct RSV/EGFR was observed.

Therapeutic treatments with scFv-IgAB_02 and RSV/EGFR at the dose of 10 mg/kg significantly reduced tumour volume as compared with the vehicle (FIG. 30). No significant difference was observed between RSV/EGFR and scFv-IgAB_02 treatment.

Flow cytometry analysis on the peripheral blood showed that the number of CD45, NK, T cells and CD14 positive cells remained constant over time. No significant difference was observed between the groups.

In the tumor, a global increase of CD45, NK and T cells and CD14 positive cells was observed 30 days after treatment initiation with scFv-IgAB_02. Expression of activation markers tended to be higher in mice treated with scFv-IgAB_02 by comparison to the vehicle and the RSV/EGFR treated group. In the spleen, no significant difference was observed between the groups.

Example 12

Pharmacokinetics
The pharmacokinetics program of scFv-IgAB_02 encompassed
  the development of a sensitive analytical assay in cynomolgus serum matrix
  an intravenous single dose PK study in cynomolgus monkeys (three dose levels)
  PK/TK assessment from dose range finding study in cynomolgus monkeys (data still pending)
  PK/TK assessment from pivotal 28 days tox study in cynomolgus monkeys (data still pending)

Bioanalysis of Pharmacokinetic Samples from Cynomolgus Monkeys

For the bioanalysis of Pharmacokinetic samples from cynomolgus monkeys an electrochemilumi-nescence immuno-assay based on the MSD® platform was performed. The MSD® platform utilizes a similar set-up like an ELISA, with the main difference that the read out is not based on an enzymatic substrate conversion like a classical ELISA but based on an electrochemiluminescence reaction. Therefore, special microplates are used with an electrode surface that adsorbs the capture antibody. Additionally, a detector labelled with the electrochemiluminescence label called SULFO-TAG™ (Ruthenium(II)tris-bipyridine conjugated as NHS ester) is required. In presence of the MSD read buffer (contains Tripropylamine, TPA) the appropriate chemical environment for electrochemiluminescence is provided. The MSD® imager applies a voltage to the plate electrodes, causing the SULFO-Tag in close proximity to the bottom of the plate to emit light through a series of reduction and oxidation reactions. The intensity of the emitted light will be detected. The signal can be amplified by multiple excitation cycles of each label to enhance light levels and improve sensitivity. Because the stimulation mechanism (electricity) is decoupled from the signal (light), minimal background signals and high signal to background ratios are possible. The assay has a LLOQ of 5 ng/ml with excellent selectivity at the LLOQ. 14/14 individuals reveal RE %<20.

The method will be fully validated under GLP to support TK assessment in the pivotal toxicity study.

Single Dose PK in Cynomolgus Monkeys
In a Citoxlab study total of nine male cynomolgus monkeys were enrolled. Animals were allocated according to the following table into three groups receiving scFv-IgAB_02 at the dose levels of 8 mg/kg (three males), 25 mg/kg (three males) and 75 mg/kg (three males). Administration was performed by a 2-hours infusion at a rate of 5 mL/kg/h.

| Group | Number, sex and identify of animals | Dose level mg/kg | Infusion rate mL/kg/h | Concentration (mg/mL) |
|---|---|---|---|---|
| 1 | 3 males: N60601 to N60603 | 8 | 5 | 0.8 |
| 2 | 3 males: N60604 to N60606 | 25 | 5 | 2.5 |
| 3 | 3 males: N60607 to N60609 | 75 | 5 | 7.5 |

Each animal was checked for mortality and morbidity twice a day during the study. They were observed at least twice a day, for the recording of clinical signs. Particular care was taken to note any local reactions at the administration site.

Body weight was recorded twice during the pre-treatment period, then on Day-1 and at least once a week until the end of the study.

Blood was collected on the day of dosing (Day 1) at pre-dose and immediately after the end of the infusion, at 5 minutes, 0.5, 1, 4, 8, 12, 24 and 48 hours and on Days 5 (96 h), 8 (168 h), 11 (240 h), 15 (336 h) and 22 (504 h) after stop of infusion. Each animal was sampled for immunogenicity on pre-treatment and on Days 8, 15 and 22 in coincidence with the PK sample.

Bioanalysis and immunogenicity analysis were performed at Chimera Biotec. Immunogenicity result were still pending when compiling this document. The pharmacokinetic analysis was performed at Citoxlab France using non-compartmental analysis on WinNonlin® software, v6.4. The following parameters: $C_{max}$, $T_{max}$, $AUC_{0-last}$, and $AUC_{0-inf}$, $t_{1/2}$, $V_z$, CL, MRT and AUMC were determined from the measured concentrations in the analyzed samples.

On completion of the observation period, on Day 27, all animals were sedated by an intramuscular injection of ketamine hydrochloride, anesthetized by an intravenous injection of pentobarbital sodium and euthanized by exsanguination.

With regard to PK results no quantifiable amounts of scFv-IgAB_02 were found in pre-dose samples.

Based on the data obtained, the following conclusions can be made (see Table14):
- systemic exposure to the test item was achieved in all animals,
- as expected, $T_{max}$ was reached at the end of scFv-IgAB_02 infusion,
- the terminal half-life, ranged from 33.4 to 154 hours,
- based on dose-normalized $AUC_{0-t}$ values, a more than dose-proportional increase in serum test item exposure was noted over the range of administered dose levels while, when considering the dose-normalized $C_{max}$, an approximately dose-proportional increase was observed.
- A slight increase in the terminal half-life value as the dose level increased was observed, thus confirming the dose-related change in the observed systemic CL of scFv-IgAB_02.
- The terminal volume of distribution $V_z$ approximates the total plasma volume in monkey indicating that scFv-IgAB_02 is mainly located in the plasma volume
- A decrease in the terminal volume of distribution values was observed with the increase of the dose, suggesting a possible saturable mechanism of tissue distribution/internalization of the test item.

TABLE 14

Pharmacokinetic parameters of individual animals in the Citoxlab study

| Group | Animal | Dose mg/kg | $t_{1/2}$ h | $C_{max}$ µg/mL | $AUC_{0-\infty}$ h·µg/mL | $V_z$ mL/kg | Cl mL/h/kg |
|---|---|---|---|---|---|---|---|
| 1 | N60601 | 8 | 42.8 | 327 | 11388 | 43.4 | 0.703 |
| 1 | N60602 | 8 | 71.4 | 301 | 9986 | 82.5 | 0.801 |
| 1 | N60603 | 8 | 44.8 | 167 | 8728 | 59.3 | 0.917 |
| 2 | N60604 | 25 | 50.8 | 1326 | 71182 | 25.7 | 0.351 |
| 2 | N60605 | 25 | 33.4 | 1236 | 51707 | 23.3 | 0.483 |
| 2 | N60606 | 25 | 45.2 | 1322 | 69583 | 23.4 | 0.359 |
| 3 | N60607 | 75 | 83.8 | 2432 | 333372 | 27.2 | 0.225 |
| 3 | N60608 | 75 | 78.5 | 2664 | 267654 | 31.7 | 0.280 |
| 3 | N60609 | 75 | 154 | 2683 | 362583 | 46.1 | 0.207 |

Example 13

Tissue Distribution of scFv-IgAB_02 in EGFR+ Tumour Bearing Mice

The assessment of tissue distribution of scFv-IgAB_02 was performed by intravenous administration of $^{125}$I-scFv-IgAB_02 into a mouse xenograft Model with A431 cells.

scFv-IgAB_02 was radiolabelled by radioiodination using Iodogen as oxidant to a final specific activity of 2 mCi/mg. Integrity of the labelled molecule was confirmed by size-exclusion chromatography and SDS-PAGE.

Biological activity was confirmed by a RIA assay on huCD16A and a saturation binding assay on A-431 cells to determine the respective $K_D$ values ($K_D$: 0.729 nM and 6.982, respectively; data not shown here). Stability in mouse plasma was confirmed over a period of 7 days.

38 mice were xenografted subcutaneously in the right flank with 5×10$^6$ A-431 cells. At the $^{125}$I-scFv-IgAB_02 injection day, the mean tumour volume was about 289±83 mm$^3$; and corresponding to a growth period of 2 weeks after inoculation.

Tissue distribution (including tumour targeting) were assessed at 8 terminal time points: 30 min, 8, 24, 48, 72, 96, 168 and 336 hours. In addition, three animals were housed in metabolic cages up to 168 hours for urine and faeces collection allowing determination of the route of excretion and the mass balance. In parallel, a quantitative whole body autoradiography study was conducted at 48 and 336 hours post-dose.

Figure 31:
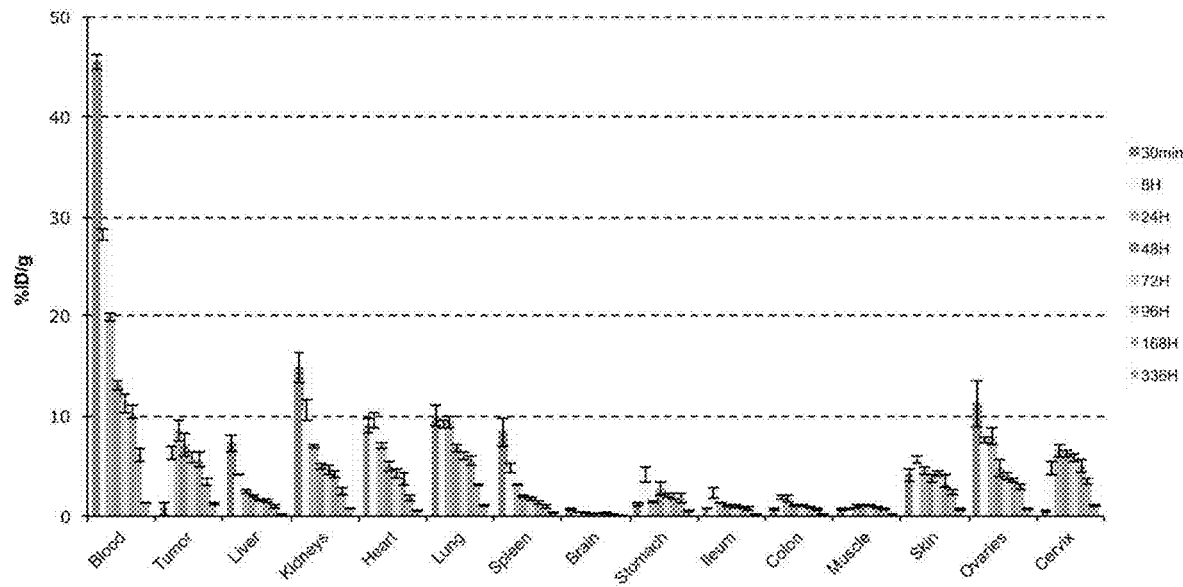
FIG. 31 shows results of tissue distribution of scFv-IgAb_02 as described in example 13. The percent of ID recovered (% ID/g) in blood and organs/tissues collected after IV injection of 125I-scFv-IgAB_02 to A431 xenograft mice

The highest concentration of radioactivity in tumour was observed between 8 and 48 hours and the maximum tumour uptake of $^{125}$I-scFv-IgAB_02 occurred 24 hours post-dose, reaching 8.56% ID/g. At the later time points, the radioactivity in tumour gradually decreased and accounted still for 5.62% ID/g at 96 hours. The radioactivity was not totally cleared from tumour at 336 hours (1.21% ID/g), indicating retention of scFv-IgAB_02 in tumour tissue (FIG. 31).

Figure 32:
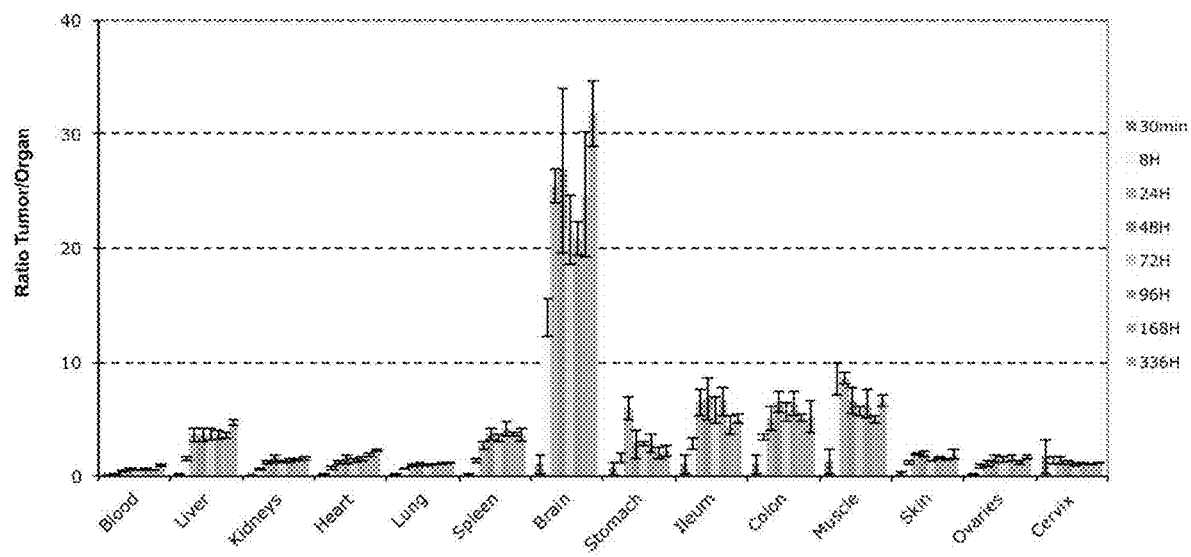
FIG. 32 shows the Tumor/Organ ratio after IV injection of $^{125}$I-scFv-IgAB_02 to A431 xenograft mice as described in example 13.

For most organs (except stomach and cervix) the tumour-to-organ ratio increased between 30 min and 24-48 hours, suggesting that the radioactivity accumulated in tumour was eliminated more slowly than that measured in organs, again indicating retention of scFv-IgAB_02 in tumour tissue (FIG. 32).

Peak radioactivity uptake was observed within the first 30 min following injection of $^{125}$I-scFv-IgAB_02 for almost all normal tissues (except for skin, cervix, muscle and digestive tract, where maximal concentration was observed at 8 and 24 hours). Then, the level of radioactivity in these tissues decreased with time without marked retention, consistent with reduction in pool blood activity.

Throughout the observation period, the highest normal organ concentration of radioactivity was found in organs involved in protein metabolism and clearing from systemic circulation such as liver, spleen and kidneys with a % ID/g of 7.25, 8.37 and 14.75, respectively, as well as in organs involved in selective accumulation of free iodine such as stomach (4.14% ID/g at 8 hours). Furthermore, high levels of radioactivity were found in lungs with 10.02% ID/g at 30 min; probably due to the presence of aggregates in the dosing solution (about 3% according to SE-HPLC analysis), as well as in ovaries and cervix with 11.22% ID/g at 30 min and 6.54% ID/g at 24 hours, respectively.

After IV administration of $^{125}$I-scFv-IgAB_02, approximately half of the injected activity was recovered in excreta at 168 hours with a cumulative urinary and faecal excretion of 43.27% and 7.40%, respectively. The radioactivity cleared via the kidney was not likely associated to scFv-IgAB_02 but should correspond to free Iodine-125 released during the dehalogenation process.

Figure 33:
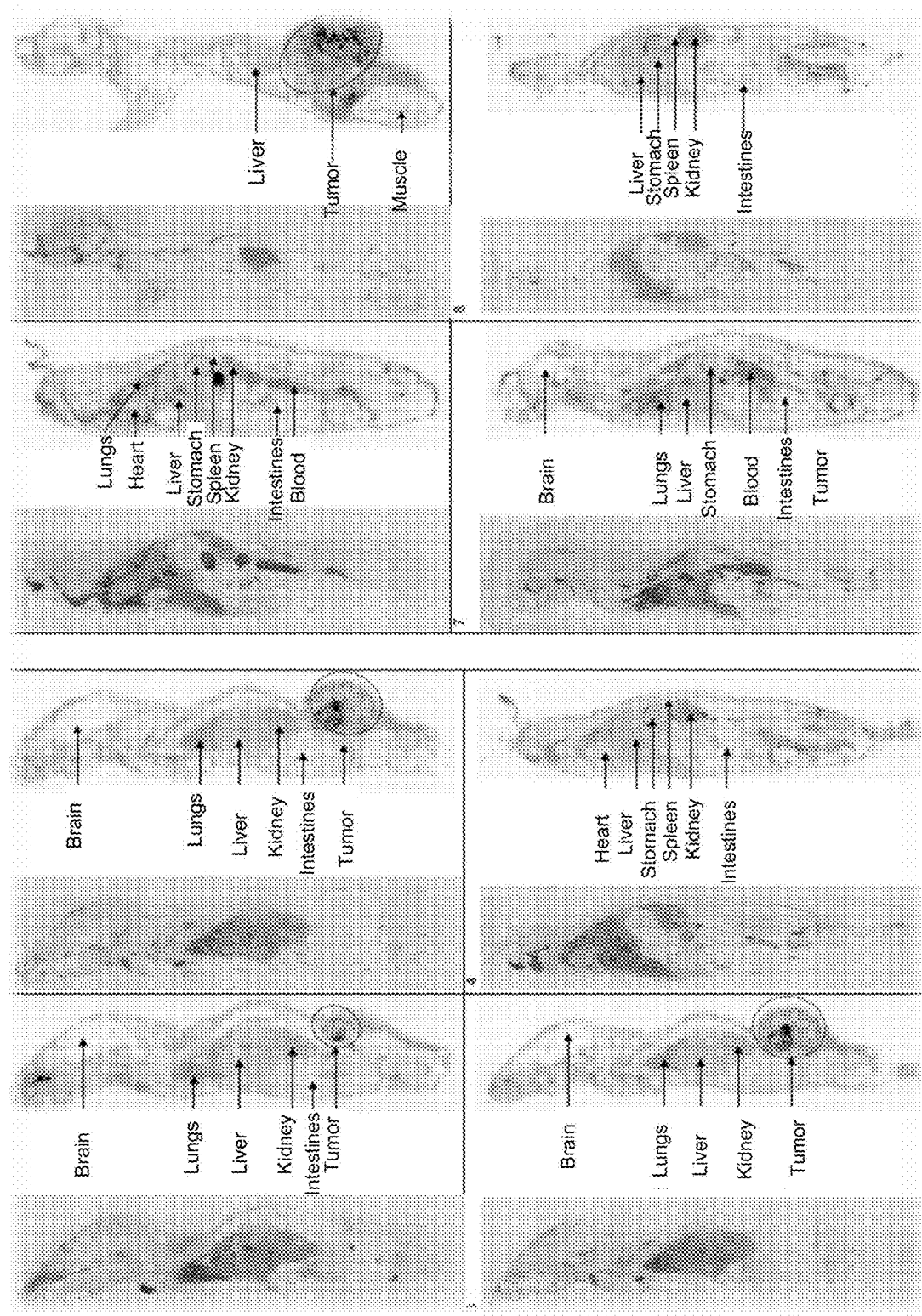
FIG. 33 shows the whole body autoradiograms of mice sacrificed at 336 hours (14 days) following IV injection of $^{125}$I-scFv-IgAB_02 as described in detail in appended example 13.

For autoradiography mice were sacrificed at 48 and 336 hours post-dose. The results of the whole body autoradiography showed an expected biodistribution pattern compared to the results obtained according to tissue dissection technique. Indeed, the radioactivity was mainly found in tumour, lungs and organs involved in metabolism and excretion mechanisms such as liver, kidneys and spleen at 48 hours post-dose. The pictures at 336 hours showed an almost complete decrease of the radioactivity in all organs/tissues while most of the remaining activity was found in the tumor (FIG. 33).

Example 14

Toxicology

Toxicology studies of bispecific EGFR/CD16 antigen-binding proteins supporting a FIM study in late-stage tumour patients were conducted in cynomolgus monkeys as a relevant species. Toxicology studies in other species were not performed.

The toxicology program of scFv-IgAB_02 conducted so far encompassed an intravenous repeated dose range finder study of 28 days duration in cynomolgus monkeys (non-GLP)

a pivotal intravenous repeated dose toxicity study of 28 days duration in cynomolgus monkeys (GLP)

For scFv-IgAB_02, a similar toxicity profile to Cetuximab can be expected due to structural similarities and a partly similar mechanism of action. However, it is important to mention that due to the reduced potential of scFv-IgAB_02 to inhibit EGFR phosphorylation, an improved side effect profile (no or decreased skin toxicity) may be expected. Nevertheless, dose levels were adapted from a 39 week study with intravenous application of Cetuximab in cynomolgus monkeys (Study 070-087, EMEA2004; Scientific discussion for the approval of Erbitux).

In the intravenous repeat dose range finder study scFv-IgAB_02 did not induce systemic or local toxicity. scFv-IgAB_02 had no effect on clinical observations, body weights, body temperature, or clinical or anatomic pathology up to the maximum tested dose level of 75 mg/kg (q7dx5). The only effects of note were a transient elevation of circulating IL-6 levels after first dose at all dose levels (within 6 h p.i.). IL-6 levels returned to normal within 24 hours after first dose. scFv-IgAB_02 did not affect the IL-2, IFN-γ, and TNF-α levels after first dose. Furthermore scFv-IgAB_02 caused a transient reduction in absolute NK cell counts (CD3−CD20−CD159+ positive) and CD69+ activated NK cells in peripheral blood at a dose ≥24 mg/kg 7 days after the first dose.

In the pivotal 28-days intravenous toxicity study of scFv-IgAB_02, the test item was well tolerated up to the maximum dose level of 75 mg/kg (q7dx5). The only test item-related findings confirmed so far were emesis in two animals at 75 mg/kg on Day 1, and an increase in WBC and especially neutrophils at 4 hours post-dose on Day 1. The transient increase in neutrophil numbers may be evoked by a transient increase of serum IL-6 levels (this is at least suggested by literature data). Some endpoints of the pivotal study are still pending when compiling this document.

Repeated Dose Intravenous Dose Range Finding Study in Cynomolgus Monkeys

The objective of the study was to determine the maximum tolerated dose of the test item, following repeated weekly IV infusion (2 h-chair infusion) to the cynomolgus monkey for 4 weeks (5 infusions in total) and a 5-week recovery phase. Ten cynomolgus monkeys of Mauritian origin (five males and five females) were allocated to dose groups as follows.

| Group Number | Group Description | Dose Level (mg/kg) | Dose Volume (mL/kg/hour) | Animals/Group Males | Animals/Group Females | Necropsy After 4 Weeks | Necropsy After 9 Weeks |
|---|---|---|---|---|---|---|---|
| 1 | Control | 0 | 5 | 1 | 1 | 1 M/1 F | — |
| 2 | Low | 8 | 5 | 1 | 1 | 1 M/1 F | — |
| 3 | Intermediate | 24 | 5 | 1 | 1 | 1 M/1 F | — |
| 4 | High | 75 | 5 | 2 | 2 | 1 M/1 F | 1 M/1 F |

F = Females;

M = Males.

Due to structural and functional similarities, dose levels and dosing regimen were chosen in strong accordance with Cetuximab toxicity assessment (EMA 2004 Scientific Discussion: WC5000291131).

Assessment of toxicity was based on clinical observations, body weights, body temperature, and clinical and anatomic pathology.

Cytokine levels of IL-2, IL-6, IL-8, TNF-α and INF-γ were determined by Multiplex technology, and a flow cytometric assessment of the lymphocyte subsets after each dose level (CD45, CD3, CD4, CD8, CD20, CD16, CD159a) was included.

Complete necropsies were performed on all animals, with a recording of macroscopic abnormalities for all tissues. Organ weights and microscopic examinations were conducted.

Blood was collected for toxicokinetic evaluation of scFv-IgAB_02 and anti-drug antibodies. Bioanalysis of toxicokinetic samples and anti-drug antibody analysis is pending.

scFv-IgAB_02 had no effect on clinical observations, body weights, body temperature, or clinical or anatomic pathology.

Figure 34:
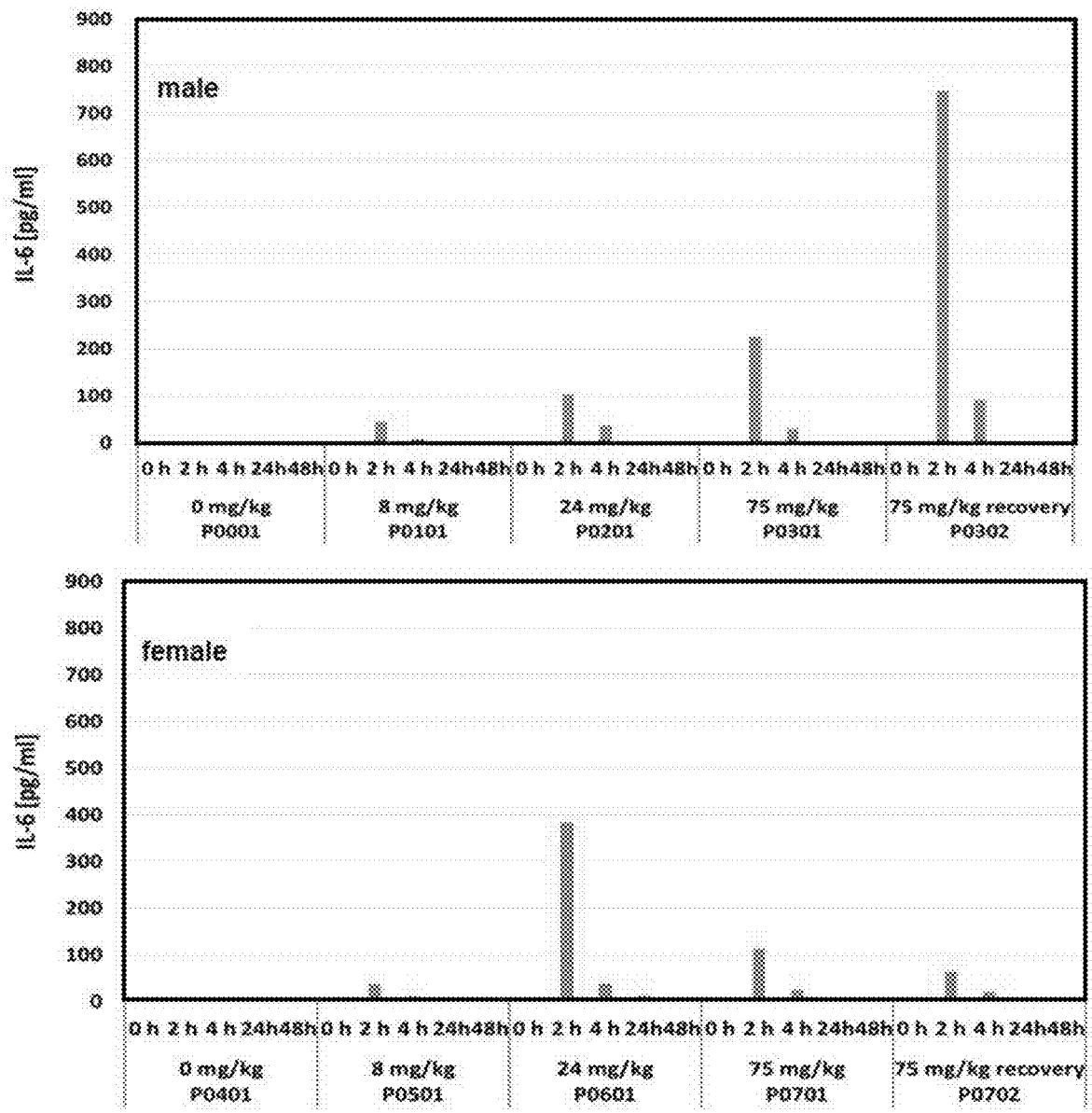
FIG. 34 shows serum IL-6 levels of individual animals observed in the toxicology study described in appended example 14.

Pharmacological action of scFv-IgAB_02 was indicated by a transient elevation of circulating IL-6 levels at all dose levels 2-4 hours after the first dose, with rapid decline of IL-6 levels after 4 h hours reverting to baseline after 24 hours (see FIG. 34).

Given the dynamic nature of NK cell homeostasis and the low group size in this study a clear assessment of scFv-IgAB_02 related effects on NK cell counts and activation status cannot be made. Almost all data were within the variability of the predose data set. A trend for a transient reduction in absolute NK cell counts (CD3$^-$ CD20$^-$CD159$^+$) and CD69$^+$ activated NK cells at a dose 24 mg/kg appeared on Day 8 which is considered scFv-IgAB_02 related because the control group was not affected.

In summary, scFv-IgAB_02 did not induce systemic or local toxicity. scFv-IgAB_02 was well tolerated up to the highest dose (75 mg/kg) when administered to cynomolgus monkeys once weekly for 28 days via IV infusion over 2 hours in the infusion chair.

Pivotal 28 Days Intravenous Toxicity Study in Cynomolgus Monkeys.

A pivotal GLP-compliant repeated dose toxicity study of four weeks duration in cynomolgus monkeys was conducted (CRO: Covance). At the time of writing this document the in-life phase of the study was completed and initial or partial results were available. However, certain final analyses of this study (e.g. histopathology, toxicokinetics) were still pending.

The objective of the study was to determine the toxicity of scFv-IgAB_02 following repeated intravenous infusion (2-h infusion, once a week) to the cynomolgus monkey for 28 days (5 infusions in total) and to assess the reversibility of effects observed, if any, during a 28 day recovery phase. The intravenous route of administration was chosen because it is the intended human therapeutic route.

Administered dose levels of scFv-IgAB_02 were 0, 8, 24, and 75 mg/kg. The study consisted of four terminal kill groups according to the table below, encompassing vehicle, medium and high dose recovery animals.

|  | Group no./sex | | | | | | | |
| --- | --- | --- | --- | --- | --- | --- | --- | --- |
|  | 1/M | 2/M | 3/M | 4/M | 1/F | 2/F | 3/F | 4/F |
| Dose Level (mg/kg/weekly) | 0 | 8 | 24 | 75 | 0 | 8 | 24 | 75 |
| Group size | 5 | 5 | 5 | 5 | 5 | 5 | 5 | 5 |
| Recovery | 2 | — | 2 | 2 | 2 | — | 2 | 2 |

During the dosing period the monkeys were observed for clinical signs, body temperature, body weight, haematology and blood chemistry, urinalysis, as well as ECG, blood pressure, and ophthalmoscopy. Furthermore, cytokine levels of IL-2, IL-6, IL-8, TNF-α and INF-γ were determined by Multiplex technology, and flow cytometric assessment of the lymphocyte subsets after each dose level (CD45, CD3, CD4, CD8, CD20, CD16, CD159a, CD14) was performed.

A special focus was put on skin toxicity (esp. delayed toxicity) since skin is major target of Cetuximab. Most prominent skin finding with Cetuximab were superficial purulent skin lesions.

After study termination the entire EMA list of tissues was collected and subjected to histopathology with an additional focus on secondary superinfections caused by erosive and ulcerative dermatitis with subsequent involvement of inner organs.

The study includes an integrated TK assessment and ADA assessment.

No preterminal mortalities occurred and no veterinarian treatment related to the test item has become necessary.

Some skin alterations occurred in single animals in Groups 1 through 4 during the study with no obvious dose dependency. These findings were considered incidental and not related to dosing with the test item.

With regard to clinical observations, two high dose males (Animals P0301 and P0305) vomited during the first dose (emesis of liquid and/or mucoid). As this was only seen in the high dose, this finding is considered test item-related.

Further clinical observations like swellings and soft faeces were considered incidental as they were infrequent, lacked a dose response, or were comparable with observations typically observed in this laboratory animal species.

Treatment with scFv-IgAB_02 up to 75 mg/kg had no effect on bodyweight development. Bodyweight development was comparable with those of controls during the dosing and recovery phases.

Treatment with scFv-IgAB_02 up to 75 mg/kg had no effect on body temperature. Significant differences in group mean body temperature between test item-dosed animals and controls were present but were considered incidental as they lacked a dose response.

No test item related ophthalmic findings were seen. Findings such as haemorrhage, brighter areas, compaction, drusen, epipapillary membrane, lesions, opacity, pigmentation or scars were seen sporadically in treated and control animals and/or occurred also in the predose phase and were comparable with observations typically noted in cynomolgus monkeys.

Treatment with scFv-IgAB_02 up to 75 mg/kg had no effect on blood pressure and respiration rate.

With regard to haematology
animals of all groups showed increased reticulocyte counts starting on Day 8 of the dosing phase. This is considered a physiological compensatory effect of the frequent blood samplings.

WBC counts, and certainly neutrophil counts were increased in animals of Group 2 to 4 on Day 1 of the dosing phase at 4 hours post-dose. The difference was not dose-dependent.

In two animals of the medium dose group (24 mg/kg) the increase was completely reversible 24 hours post-dose. For the other animals and groups, no sample was collected at 24 hours. Recovery was shown for all other groups on Day 8. However, complete recovery at 24 hours is expected in all groups.

Treatment with scFv-IgAB_02 up to 75 mg/kg had no effect on clinical chemistry, coagulation, and urine parameters.

For the time being, histopathology, TK and ADA assessment, as well as some other endpoints such as ECG analysis, immunophenotyping analysis, cytokine analysis are still pending. All preliminary macroscopic observations were consistent with spontaneous background changes commonly found in this species. However, final evaluation by the Study Pathologist is pending. The same holds for organ weights.

In summary, test item related findings confirmed so far were as follows:

Emesis in two animals at 75 mg/kg on Day 1

Increase in WBC and especially ANEU at 4 hours post-dose on Day 1

Sequence Listing

| SEQ ID NO | Sequence |
|---|---|
| 1 | VH EGER:<br>QVQLQESGPGLVKPSETLSLTCTVSGGSVSSGSYYWSWIRQPPGKGLEWIGYIYYSGSTNYNP<br>SLKSRVTISVDTSKNQFSLKLSSVTAADTAVYYCARNPISIPAFDIWGQGTMVTVSS |
| 2 | VL EGFR:<br>QPVLTQPPSVSVAPGKTARITCGGNNIGSKSVHWYQQKPGQAPVLVIYYDSDRPSGIPERFSG<br>SNSGNTATLTISRVEAGDEADYYCQVWDTSSDHVLFGGGTKLTVL |
| 3 | C-terminal sequence of CD16A:<br>SFFPPGYQ |
| 4 | CD16A:<br>GMRTEDLPKAVVFLEPQWYRVLEKDSVTLKCQGAYSPEDNSTQWFHNESLISSQASSYFIDAA<br>TVDDSGEYRCQTNLSTLSDPVQLEVHIGWLLLQAPRWVFKEEDPIHLRCHSWKNTALHKVTYL<br>QNGKGRKYFHHNSDFYIPKATLKDSGSYFCRGLFGSKNVSSETVNITITQGLAVSTISSFFPP<br>GYQ |
| 5 | HCDR1 CD16A:<br>GYTFTSYY |
| 6 | HCDR2 CD16A:<br>INPSGGST |
| 7 | HCDR3 CD16A:<br>ARGSAYYYDFADY |
| 8 | LCDR1 CD16A:<br>NIGSKN |
| 9 | LCDR2 CD16A:<br>QDN |
| 10 | LCDR3 CD16A:<br>QVWDNYSVL |
| 11 | HCDR2 CD16A-2:<br>IEPMYGST |
| 12 | VH CD16A:<br>QVQLVQSGAEVKKPGESLKVSCKASGYTFTSYYMHWVRQAPGQGLEWMGIINPSGGSTSYAQK<br>FQGRVTMTRDTSTSTVYMELSSLRSEDTAVYYCARGSAYYYDFADYWGQGTLVTVSS |
| 13 | VL CD16A:<br>SYVLTQPSSVSVAPGQTATISCGGHNIGSKNVHWYQQRPGQSPVLVIYQDNKRPSGIPERFSG<br>SNSGNTATLTISGTQAMDEADYYCQVWDNYSVLFGGGTKLTVL |
| 14 | VH CD16A-2:<br>QVQLVQSGAEVKKPGESLKVSCKASGYTFTSYYMHWVRQAPGQGLEWMGAIEPMYGSTSYAQK<br>FQGRVTMTRDTSTSTVYMELSSLRSEDTAVYYCARGSAYYYDFADYWGQGTLVTVSS |
| 15 | Human IgG1 CH1, CH2 and CH3 heavy chain constant domain:<br>ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPCPAPEFEGGPSVFLF<br>PPKPKDTLMISRTPEVTCVVVAVSHEDPEVKFNWYVDGVEVHNAKTKPREEQYNSTYRVVSVL<br>TVLHQDWLNGKEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNVFSCSVMHEAL<br>HNHYTQKSLSLSPG |

Sequence Listing

| SEQ ID NO | Sequence |
|---|---|
| 16 | Human lambda light chain constant domain:<br>GQPKAAPSVTLFPPSSEELQANKATLVCLISDFYPGAVTVAWKADSSPVKAGVETTTPSKQSN<br>NKYAASSYLSLTPEQWKSHRSYSCQVTHEGSTVEKTVAPTECS |
| 17 | Linker:<br>GGGGSGGGGS |
| 18 | Linker:<br>GGSGGSGGSGGSGGSGGS |
| 19 | Hinge:<br>EPKSCDKTHTCPPCP |
| 20 | CH2-CH3 heavy chain constant domain:<br>APEFEGGPSVFLFPPKPKDTLMISRTPEVTCVVVAVSHEDPEVKFNWYVDGVEVHNAKTKPRE<br>EQYNSTYRVVSVLTVLHQDWLNGKEYKCKVSNKALPAPIEKTISKAKGQPREPQVYTLPPSRE<br>EMTKNQVSLTCLVKGFYPSDIAVEWESNGQPENNYKTTPPVLDSDGSFFLYSKLTVDKSRWQQ<br>GNVFSCSVMHEALHNHYTQKSLSLSPG |
| 21 | HCDR1 EGFR:<br>GGSVSSGSYY |
| 22 | HCDR2 EGFR:<br>IYYSGST |
| 23 | HCDR3 EGFR:<br>ARNPISIPAFDI |
| 24 | LCDR1 EGFR:<br>NIGSKS |
| 25 | LCDR2 EGFR:<br>YDS |
| 26 | LCDR3 EGFR:<br>QVWDTSSDHVL |
| 27 | Tandem diabody with 6xHis-Tag:<br>QVQLQESGPGLVKPSETLSLTCTVSGGSVSSGSYYWSWIRQPPGKGLEWIGYIYYSGSTNYNP<br>SLKSRVTISVDTSKNQFSLKLSSVTAADTAVYYCARNPISIPAFDIWGQGTMVTVSSGGSGGS<br>GGSSYVLTQPSSVSVAPGQTATISCGGHNIGSKNVHWYQQRPGQSPVLVIYQDNKRPSGIPER<br>FSGSNSGNTATLTISGTQAMDEADYYCQVWDNYSVLFGGGTKLTVLGGSGGSQVQLVQSGAEV<br>KKPGESLKVSCKASGYTFTSYYMHWVRQAPGQGLEWMGIINPSGGSTSYAQKFQGRVTMTRDT<br>STSTVYMELSSLRSEDTAVYYCARGSAYYYDFADYWGQGTLVTVSSGGSGGSGGSQPVLTQPP<br>SVSVAPGKTARITCGGNNIGSKSVHWYQQKPGQAPVLVIYYDSDRPSGIPERFSGSNSGNTAT<br>LTISRVEAGDEADYYCQVWDTSSDHVLFGGGTKLTVLAAAGSHHHHHH |
| 28 | scFv-IgAb_02 heavy chain:<br>QVQLVQSGAEVKKPGESLKVSCKASGYTFTSYYMHWVRQAPGQGLEWMGIINPSGGSTSYAQK<br>FQGRVTMTRDTSTSTVYMELSSLRSEDTAVYYCARGSAYYYDFADYWGQGTLVTVSSASTKGP<br>SVFPLAPSSKSTSGGTAALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPEFEGGPSVFLFPPKPKD<br>TLMISRTPEVTCVVVAVSHEDPEVKFNWYVDGVEVHNAKTKPREEQYNSTYRVVSVLTVLHQD<br>WLNGKEYKCKVSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVMHEALHNHYTQ<br>KSLSLSPGGGGSGGGGSQVQLQESGPGLVKPSETLSLTCTVSGGSVSSGSYYWSWIRQPPGK<br>GLEWIGYIYYSGSTNYNPSLKSRVTISVDTSKNQFSLKLSSVTAADTAVYYCARNPISIPAFD<br>IWGQGTMVTVSSGGSGGSGGSGGSGGSGGSQPVLTQPPSVSVAPGKTARITCGGNNIGSKSVH<br>WYQQKPGQAPVLVIYYDSDRPSGIPERFSGSNSGNTATLTISRVEAGDEADYYCQVWDTSSDH<br>VLFGGGTKLTVL |
| 29 | scFv-IgAb_02 light chain:<br>SYVLTQPSSVSVAPGQTATISCGGHNIGSKNVHWYQQRPGQSPVLVIYQDNKRPSGIPERFSG<br>SNSGNTATLTISGTQAMDEADYYCQVWDNYSVLFGGGTKLTVLGQPKAAPSVTLFPPSSEELQ<br>ANKATLVCLISDFYPGAVTVAWKADSSPVKAGVETTTPSKQSNNKYAASSYLSLTPEQWKSHR<br>SYSCQVTHEGSTVEKTVAPTECS |
| 30 | Bi-scFv-Fc 02:<br>SYVLTQPSSVSVAPGQTATISCGGHNIGSKNVHWYQQRPGQSPVLVIYQDNKRPSGIPERFSG<br>SNSGNTATLTISGTQAMDEADYYCQVWDNYSVLFGGGTKLTVLGGSGGSGGSGGSGGSGGSGG<br>SQVQLVQSGAEVKKPGESLKVSCKASGYTFTSYYMHWVRQAPGQGLEWMGIINPSGGSTSYAQ<br>KFQGRVTMTRDTSTSTVYMELSSLRSEDTAVYYCARGSAYYYDFADYWGQGTLVTVSSEPKSC<br>DKTHTCPPCPAPEFEGGPSVFLFPPKPKDTLMISRTPEVTCVVVAVSHEDPEVKFNWYVDGVE |

| SEQ ID NO | Sequence |
|---|---|
| | VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSQVQLQESGPGLVKPSE
TLSLTCTVSGGSVSSGSYYWSWIRQPPGKGLEWIGYIYYSGSTNYNPSLKSRVTISVDTSKNQ
FSLKLSSVTAADTAVYYCARNPISIPAFDIWGQGTMVTVSSGGSGGSGGSGGSGGSGGSQPVL
TQPPSVSVAPGKTARITCGGNNIGSKSVHWYQQKPGQAPVLVIYYDSDRPSGIPERFSGSNSG
NTATLTISRVEAGDEADYYCQVWDTSSDHVLFGGGTKLTVL |
| 31 | VH HSA:
EVQLLESGGGLVQPGGSLRLSCAVSGIDLSNYAINWVRQAPGKGLEWIGIIWASGTTFYATWA
KGRFTISRDNSKNTVYLQMNSLRAEDTAVYYCARTVPGYSTAPYFDLWGQGTLVTVSS |
| 32 | VL HSA:
DIQMTQSPSSVSASVGDRVTITCQSSPSVWSNFLSWYQQKPGKAPKLLIYEASKLTSGVPSRF
SGSGSGTDFTLTISSLQPEDFATYYCGGGYSSISDTTFGGGTKVEIK |
| 33 | Primer:
TAATACGACTCACTATAGGG |
| 34 | Primer:
TAGAAGGCACAGTCGAGG |
| 35 | Linker:
GGSGGS |
| 36 | Linker:
GGSGGSGGS |
| 37 | Linker:
GGSGGSGGSGGSGGSGGSGGSGGS |
| 38 | HCDR1 CD16A-2:
GYTFTSYY |
| 39 | HCDR3 CD16A-2:
ARGSAYYYDFADY |
| 40 | LCDR1 CD16A-2:
NIGSKN |
| 41 | LCDR2 CD16A-2:
QDN |
| 42 | LCDR3 CD16A-2:
QVWDNYSVL |
| 43 | scFv-IgAb_02 CD16A-2 heavy chain:
QVQLVQSGAEVKKPGESLKVSCKASGYTFTSYYMHWVRQAPGQGLEWMGAIEPMYGSTSYAQK
FQGRVTMTRDTSTSTVYMELSSLRSEDTAVYYCARGSAYYYDFADYWGQGTLVTVSSASTKGP
SVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPEFEGGPSVFLFPPKPKD
TLMISRTPEVTCVVVAVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQ
KSLSLSPGGGGSGGGGSQVQLQESGPGLVKPSETLSLTCTVSGGSVSSGSYYWSWIRQPPGK
GLEWIGYIYYSGSTNYNPSLKSRVTISVDTSKNQFSLKLSSVTAADTAVYYCARNPISIPAFD
IWGQGTMVTVSSGGSGGSGGSGGSGGSGGSQPVLTQPPSVSVAPGKTARITCGGNNIGSKSVH
WYQQKPGQAPVLVIYYDSDRPSGIPERFSGSNSGNTATLTISRVEAGDEADYYCQVWDTSSDH
VLFGGGTKLTVL |
| 44 | scFv-IgAb_02 CD16A-2 light chain:
SYVLTQPPSVSVAPGQTATISCGGHNIGSKNVHWYQQRPGQSPVLVIYQDNKRPSGIPERFSG
SNSGNTATLTISGTQAMDEADYYCQVWDNYSVLFGGGTKLTVLGQPKAAPSVTLFPPSSEELQ
ANKATLVCLISDFYPGAVTVAWKADSSPVKAGVETTTPSKQSNNKYAASSYLSLTPEQWKSHR
SYSCQVTHEGSTVEKTVAPTECS |
| 45 | Bi-scFv-Fc 02 CD16A-2:
SYVLTQPPSVSVAPGQTATISCGGHNIGSKNVHWYQQRPGQSPVLVIYQDNKRPSGIPERFSG
SNSGNTATLTISGTQAMDEADYYCQVWDNYSVLFGGGTKLTVLGGSGGSGGSGGSGGSGGSGG
SQVQLVQSGAEVKKPGESLKVSCKASGYTFTSYYMHWVRQAPGQGLEWMGAIEPMYGSTSYAQ
KFQGRVTMTRDTSTSTVYMELSSLRSEDTAVYYCARGSAYYYDFADYWGQGTLVTVSSEPKSC
DKTHTCPPCPAPEFEGGPSVFLFPPKPKDTLMISRTPEVTCVVVAVSHEDPEVKFNWYVDGVE
VHNAKTKPREEQYNSTYRVVSVLTVLHQDWLNGKEYKCKVSNKALPAPIEKTISKAKGQPREP |

Sequence Listing

| SEQ ID NO | Sequence |
|---|---|
| | QVYTLPPSREEMTKNQVSLTCLVKGFYPSDIAVEWESNGQPENNYKTTPPVLDSDGSFFLYSK LTVDKSRWQQGNVFSCSVMHEALHNHYTQKSLSLSPGGGGGSGGGGSQVQLQESGPGLVKPSE TLSLTCTVSGGSVSSGSYYWSWIRQPPGKGLEWIGYIYYSGSTNYNPSLKSRVTISVDTSKNQ FSLKLSSVTAADTAVYYCARNPISIPAFDIWGQGTMVTVSSGGSGGSGGSGGSGGSGGSQPVL TQPPSVSVAPGKTARITCGGNNIGSKSVHWYQQKPGQAPVLVIYYDSDRPSGIPERFSGSNSG NTATLTISRVEAGDEADYYCQVWDTSSDHVLFGGGTKLTVL |

---

The invention claimed is:

1. An antigen-binding protein comprising an antigen-binding site for EGFR, wherein the antigen-binding site comprises a heavy chain variable domain (VH) and a light chain variable domain (VL) wherein:

(i) VH comprises a heavy chain CDR1 having the amino acid sequence set forth in SEQ ID NO:21; a heavy chain CDR2 having the amino acid sequence set forth in SEQ ID NO:22; a heavy chain CDR3 having the amino acid sequence set forth in SEQ ID NO:23 and VL comprises a light chain CDR1 having an amino acid sequence set forth in SEQ ID NO:24; a light chain CDR2 having an amino acid sequence set forth in SEQ ID NO:25; and a light chain CDR3 having an amino acid sequence set forth in SEQ ID NOs:26; or (ii) VH has the amino acid sequence set forth in SEQ ID NOs:1 and VL has the amino acid sequence set forth in SEQ ID NO:2.

2. The antigen binding protein of claim 1, wherein the antigen binding protein further comprises an antigen binding site for CD16A.

3. The antigen binding protein of claim 2, wherein the antigen binding site for CD16A comprises:

(i) a variable heavy chain domain (VH) comprising a heavy chain CDR1 having the amino acid sequence set forth in SEQ ID NO:5; a heavy chain CDR2 having the amino acid sequence set forth in SEQ ID NO:6 or 11;

a heavy chain CDR3 having the amino acid sequence set forth in SEQ ID NO:7, and a variable light chain domain (VL) comprising a light chain CDR1 having an amino acid sequence set forth in SEQ ID NO:8; a light chain CDR2 having an amino acid sequence set forth in SEQ ID NO:9; and a light chain CDR3 having an amino acid sequence set forth in SEQ ID NO:10; or (ii) a VH comprising the amino acid sequence set forth in SEQ ID NO:12 or 14 and a VL comprising the amino acid sequence set forth in SEQ ID NO:13.

4. The antigen-binding protein of claim 1, wherein the antigen-binding protein comprises at least two antigen-binding sites for EGFR.

5. The antigen-binding protein of claim 2, wherein the antigen-binding protein comprises at least two antigen-binding sites for CD16A.

6. The antigen-binding protein of claim 4, wherein the antigen-binding protein comprises at least two antigen-binding sites for CD16A.

7. The antigen-binding protein of claim 6, wherein the antigen-binding protein consists of two polypeptide chains, wherein each polypeptide chain comprises at least four variable chain domains from the group consisting of a VH specific for CD16A, a VL specific for CD16A, a VH specific for EGFR and a VL specific for EGFR.

8. The antigen-binding protein of claim 1, wherein the antigen-binding protein is a dimer comprising a first polypeptide comprising at least six variable domains and a second polypeptide comprising at least two variable domains.

9. The antigen-binding protein of claim 8, wherein the antigen-binding protein is bispecific or trispecific.

10. The antigen-binding protein of claim 9, wherein the antigen-binding protein comprises antigen-binding sites for EGFR, CD16A and human serum albumin (HSA).

11. The antigen-binding protein of claim 1, further comprising
(i) an antigen-binding site for serum albumin, or
(ii) serum albumin fused to the antigen-binding protein.

12. The antigen-binding protein of claim 3, comprising an amino acid sequence selected from the group consisting of SEQ ID NO:27, SEQ ID NO:30 and SEQ ID NO:45.

13. A method for treating or ameliorating a proliferative disease or a tumorous disease, comprising administering to a subject in need thereof the antigen-binding protein of claim 2.

14. The method of claim 13, comprising the step of administering to a subject in need thereof an antigen-binding protein, wherein the antigen-binding protein comprises a heavy chain having the amino acid sequence set forth in SEQ ID NO:28 and a light chain having the amino acid sequence set forth in SEQ ID NO:29 or a heavy chain having the amino acid sequence set forth in SEQ ID NO:43 and a light chain having the amino acid sequence set forth in SEQ ID NO:44.

15. The method of claim 13, comprising the step of administering to a subject in need thereof the antigen-binding protein of claim 12.

16. The method of claim 13, wherein the proliferative disease or tumorous disease is characterized by EGFR-positive or EGFR vIII-positive cells.

17. The method of claim 16, wherein the proliferative disease or tumorous disease is selected from the group consisting of colorectal cancer, head and neck cancer, lung cancer and glioblastoma.

* * * * *